US012331078B2

(12) United States Patent
Whitehead et al.

(10) Patent No.: US 12,331,078 B2
(45) Date of Patent: Jun. 17, 2025

(54) STABILIZING MUTANTS OF PREFUSION SARS-COV-2 (COVID-19) SPIKE PROTEIN AND IMPROVED YEAST SURFACE DISPLAY ENGINEERING PLATFORM FOR THE SAME

(71) Applicant: The Regents of the University of Colorado, a body corporate, Denver, CO (US)

(72) Inventors: Timothy Whitehead, Boulder, CO (US); Monica Kirby, Boulder, CO (US); Zachary Baumer, Boulder, CO (US); Matthew Bedewitz, Boulder, CO (US); Brian Petersen, Boulder, CO (US); Paul J. Steiner, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 133 days.

(21) Appl. No.: 17/318,719

(22) Filed: May 12, 2021

(65) Prior Publication Data

US 2021/0355170 A1    Nov. 18, 2021

Related U.S. Application Data

(60) Provisional application No. 63/062,123, filed on Aug. 6, 2020, provisional application No. 63/026,316, filed on May 18, 2020.

(51) Int. Cl.
| | |
|---|---|
| *C07K 14/005* | (2006.01) |
| *A61K 31/427* | (2006.01) |
| *C12N 15/81* | (2006.01) |
| *A61K 39/00* | (2006.01) |

(52) U.S. Cl.
CPC ............ *C07K 14/005* (2013.01); *C12N 15/81* (2013.01); *A61K 39/00* (2013.01); *C12N 2770/20022* (2013.01); *C12N 2770/20034* (2013.01)

(58) Field of Classification Search
None
See application file for complete search history.

(56) References Cited

PUBLICATIONS

GenPept accession 6VSB_A (May 7, 2020).*
Pallesen J, et al. Immunogenicity and structures of a rationally designed prefusion MERS-CoV spike antigen. Proc Natl Acad Sci U S A.Aug. 29, 2017;114(35):E7348-E7357. doi: 10.1073/pnas. 1707304114. Epub Aug. 14, 2017. PMID: 28807998; PMCID: PMC5584442.*
Bowie et al., Deciphering the Message in Protein Sequences: Tolerance to Amino Acid Substitutions, 1990, Science, vol. 247, No. 4948, pp. 1306-1310.*
GenBank QJF75438.1. Apr. 30, 2020. (Year: 2020).*

* cited by examiner

*Primary Examiner* — Agnieszka Boesen
(74) *Attorney, Agent, or Firm* — Berg Hill Greenleaf Ruscitti LLP

(57) ABSTRACT

The invention relates to one or more mutations configured to stabilize the prefusion "up" protomer trimeric Spike protein from SARS-CoV-2. The inventive technology further relates to systems, methods, and compositions to display one or more proteins on the surface of a yeast cell. Specifically, in one embodiment the invention relates to systems, methods, and compositions to display one or more Spike protein from SARS-CoV-2 on the surface of a yeast cell, and more preferably a Spike protein from SARS-CoV-2 stabilized in its prefusion conformation on the surface of a yeast cell.

13 Claims, 13 Drawing Sheets
Specification includes a Sequence Listing.

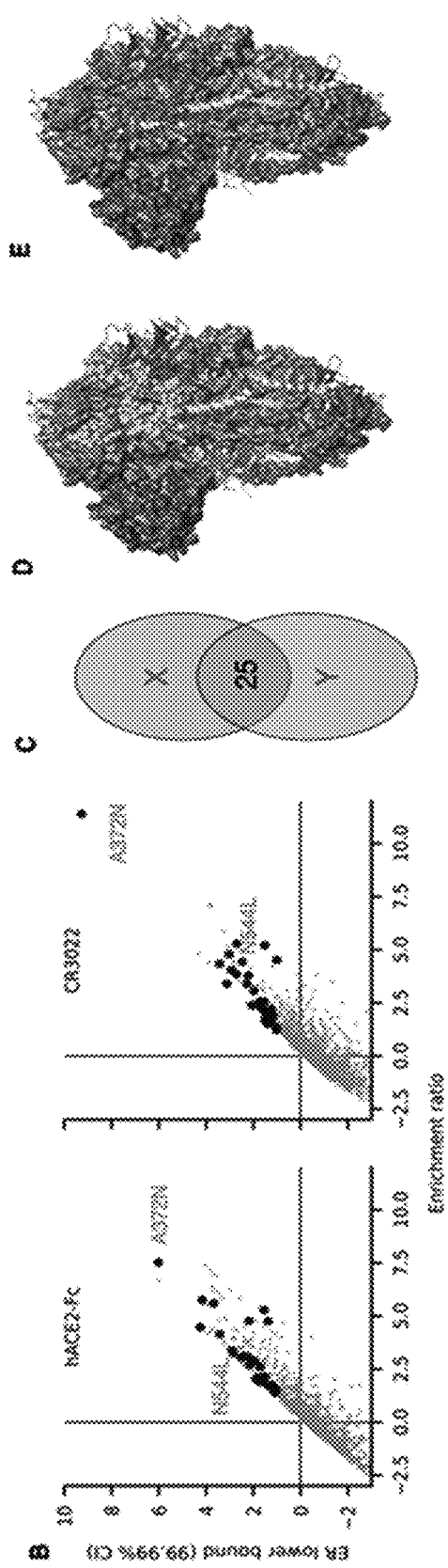
FIG. 3B-E

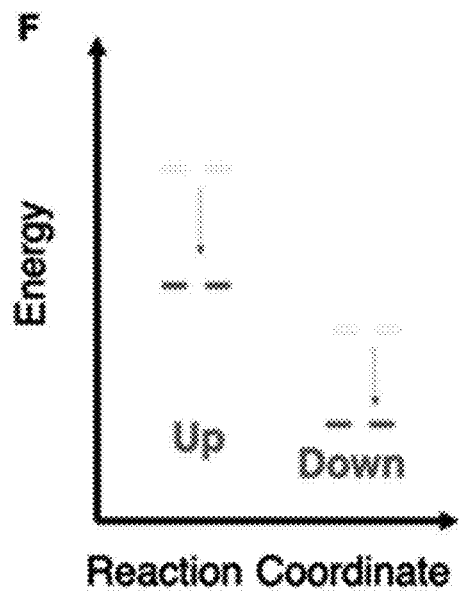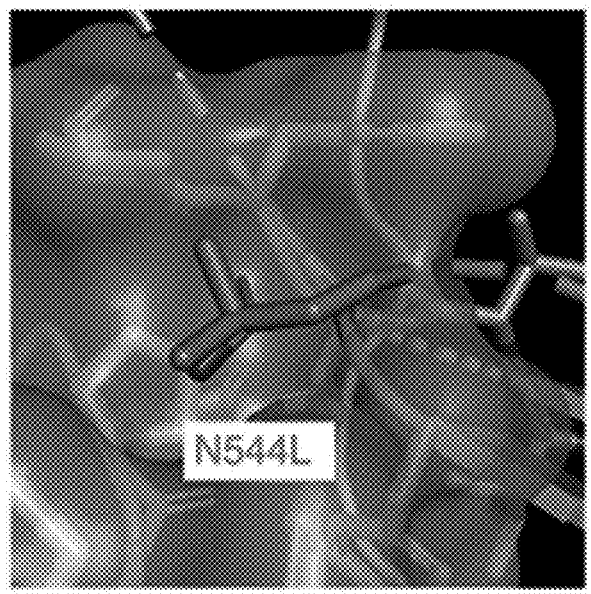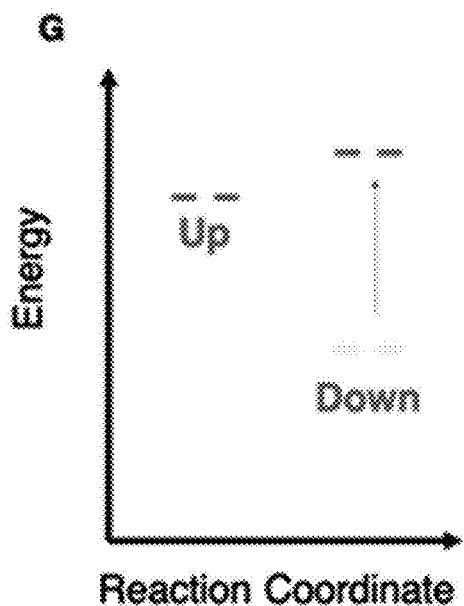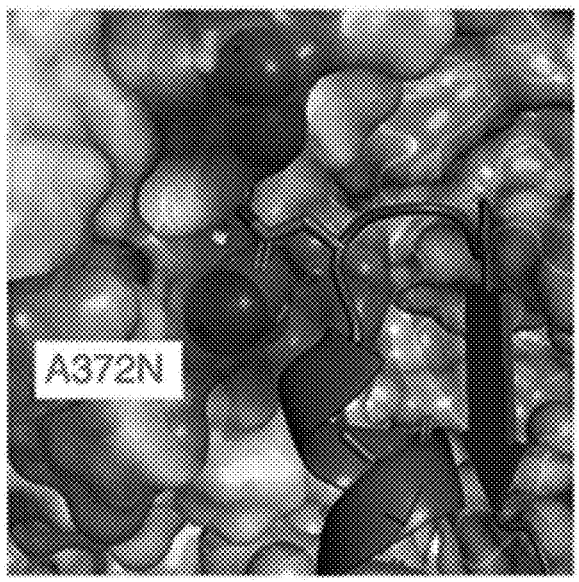
FIG. 3F-G

SEQUENCE LISTING

<160> NUMBER OF SEQ ID NOS: 55

<210> SEQ ID NO 1
<211> LENGTH: 1186
<212> TYPE: PRT

<213> ORGANISM: SARS-CoV-2 coronavirus isolate Wuhan-Hu-1

<400> SEQUENCE: 1

```
Ser Gln Cys Val Asn Leu Thr Thr Arg Thr Gln Leu Pro Pro Ala Tyr
1               5                   10                  15

Thr Asn Ser Phe Thr Arg Gly Val Tyr Tyr Pro Asp Lys Val Phe Arg
            20                  25                  30

Ser Ser Val Leu His Ser Thr Gln Asp Leu Phe Leu Pro Phe Phe Ser
        35                  40                  45

Asn Val Thr Trp Phe His Ala Ile His Val Ser Gly Thr Asn Gly Thr
    50                  55                  60

Lys Arg Phe Asp Asn Pro Val Leu Pro Phe Asn Asp Gly Val Tyr Phe
65                  70                  75                  80

Ala Ser Thr Glu Lys Ser Asn Ile Ile Arg Gly Trp Ile Phe Gly Thr
                85                  90                  95

Thr Leu Asp Ser Lys Thr Gln Ser Leu Leu Ile Val Asn Asn Ala Thr
            100                 105                 110

Asn Val Val Ile Lys Val Cys Glu Phe Gln Phe Cys Asn Asp Pro Phe
        115                 120                 125

Leu Gly Val Tyr Tyr His Lys Asn Asn Lys Ser Trp Met Glu Ser Glu
    130                 135                 140

Phe Arg Val Tyr Ser Ser Ala Asn Asn Cys Thr Phe Glu Tyr Val Ser
145                 150                 155                 160

Gln Pro Phe Leu Met Asp Leu Glu Gly Lys Gln Gly Asn Phe Lys Asn
                165                 170                 175

Leu Arg Glu Phe Val Phe Lys Asn Ile Asp Gly Tyr Phe Lys Ile Tyr
            180                 185                 190

Ser Lys His Thr Pro Ile Asn Leu Val Arg Asp Leu Pro Gln Gly Phe
        195                 200                 205

Ser Ala Leu Glu Pro Leu Val Asp Leu Pro Ile Gly Ile Asn Ile Thr
    210                 215                 220

Arg Phe Gln Thr Leu Leu Ala Leu His Arg Ser Tyr Leu Thr Pro Gly
225                 230                 235                 240

Asp Ser Ser Ser Gly Trp Thr Ala Gly Ala Ala Ala Tyr Tyr Val Gly
                245                 250                 255

Tyr Leu Gln Pro Arg Thr Phe Leu Leu Lys Tyr Asn Glu Asn Gly Thr
            260                 265                 270

Ile Thr Asp Ala Val Asp Cys Ala Leu Asp Pro Leu Ser Glu Thr Lys
        275                 280                 285

Cys Thr Leu Lys Ser Phe Thr Val Glu Lys Gly Ile Tyr Gln Thr Ser
    290                 295                 300

Asn Phe Arg Val Gln Pro Thr Glu Ser Ile Val Arg Phe Pro Asn Ile
305                 310                 315                 320

Thr Asn Leu Cys Pro Phe Gly Glu Val Phe Asn Ala Thr Arg Phe Ala
                325                 330                 335

Ser Val Tyr Ala Trp Asn Arg Lys Arg Ile Ser Asn Cys Val Ala Asp
            340                 345                 350

Tyr Ser Val Leu Tyr Asn Ser Ala Ser Phe Ser Thr Phe Lys Cys Tyr
        355                 360                 365

Gly Val Ser Pro Thr Lys Leu Asn Asp Leu Cys Phe Thr Asn Val Tyr
    370                 375                 380

Ala Asp Ser Phe Val Ile Arg Gly Asp Glu Val Arg Gln Ile Ala Pro
385                 390                 395                 400
```

-continued

Gly Gln Thr Gly Lys Ile Ala Asp Tyr Asn Tyr Lys Leu Pro Asp Asp
            405                 410                 415

Phe Thr Gly Cys Val Ile Ala Trp Asn Ser Asn Asn Leu Asp Ser Lys
        420                 425                 430

Val Gly Gly Asn Tyr Asn Tyr Leu Tyr Arg Leu Phe Arg Lys Ser Asn
        435                 440                 445

Leu Lys Pro Phe Glu Arg Asp Ile Ser Thr Glu Ile Tyr Gln Ala Gly
    450                 455                 460

Ser Thr Pro Cys Asn Gly Val Glu Gly Phe Asn Cys Tyr Phe Pro Leu
465                 470                 475                 480

Gln Ser Tyr Gly Phe Gln Pro Thr Asn Gly Val Gly Tyr Gln Pro Tyr
                485                 490                 495

Arg Val Val Val Leu Ser Phe Glu Leu Leu His Ala Pro Ala Thr Val
            500                 505                 510

Cys Gly Pro Lys Lys Ser Thr Asn Leu Val Lys Asn Lys Cys Val Asn
        515                 520                 525

Phe Asn Phe Asn Gly Leu Thr Gly Thr Gly Val Leu Thr Glu Ser Asn
    530                 535                 540

Lys Lys Phe Leu Pro Phe Gln Gln Phe Gly Arg Asp Ile Ala Asp Thr
545                 550                 555                 560

Thr Asp Ala Val Arg Asp Pro Gln Thr Leu Glu Ile Leu Asp Ile Thr
                565                 570                 575

Pro Cys Ser Phe Gly Gly Val Ser Val Ile Thr Pro Gly Thr Asn Thr
            580                 585                 590

Ser Asn Gln Val Ala Val Leu Tyr Gln Asp Val Asn Cys Thr Glu Val
        595                 600                 605

Pro Val Ala Ile His Ala Asp Gln Leu Thr Pro Thr Trp Arg Val Tyr
    610                 615                 620

Ser Thr Gly Ser Asn Val Phe Gln Thr Arg Ala Gly Cys Leu Ile Gly
625                 630                 635                 640

Ala Glu His Val Asn Asn Ser Tyr Glu Cys Asp Ile Pro Ile Gly Ala
                645                 650                 655

Gly Ile Cys Ala Ser Tyr Gln Thr Gln Thr Asn Ser Pro Gly Ser Ala
            660                 665                 670

Ser Ser Val Ala Ser Gln Ser Ile Ile Ala Tyr Thr Met Ser Leu Gly
        675                 680                 685

Ala Glu Asn Ser Val Ala Tyr Ser Asn Asn Ser Ile Ala Ile Pro Thr
    690                 695                 700

Asn Phe Thr Ile Ser Val Thr Thr Glu Ile Leu Pro Val Ser Met Thr
705                 710                 715                 720

Lys Thr Ser Val Asp Cys Thr Met Tyr Ile Cys Gly Asp Ser Thr Glu
                725                 730                 735

Cys Ser Asn Leu Leu Leu Gln Tyr Gly Ser Phe Cys Thr Gln Leu Asn
            740                 745                 750

Arg Ala Leu Thr Gly Ile Ala Val Glu Gln Asp Lys Asn Thr Gln Glu
        755                 760                 765

Val Phe Ala Gln Val Lys Gln Ile Tyr Lys Thr Pro Pro Ile Lys Asp
    770                 775                 780

Phe Gly Gly Phe Asn Phe Ser Gln Ile Leu Pro Asp Pro Ser Lys Pro
785                 790                 795                 800

Ser Lys Ser Ser Phe Ile Glu Asp Leu Leu Phe Asn Lys Val Thr Leu
                805                 810                 815

Ala Asp Ala Gly Phe Ile Lys Gln Tyr Gly Asp Cys Leu Gly Asp Ile

```
                820                 825                 830
Ala Ala Arg Asp Leu Ile Cys Ala Gln Lys Phe Asn Gly Leu Thr Val
            835                 840                 845

Leu Pro Pro Leu Leu Thr Asp Glu Met Ile Ala Gln Tyr Thr Ser Ala
850                 855                 860

Leu Leu Ala Gly Thr Ile Thr Ser Gly Trp Thr Phe Gly Ala Gly Ala
865                 870                 875                 880

Ala Leu Gln Ile Pro Phe Ala Met Gln Met Ala Tyr Arg Phe Asn Gly
            885                 890                 895

Ile Gly Val Thr Gln Asn Val Leu Tyr Glu Asn Gln Lys Leu Ile Ala
            900                 905                 910

Asn Gln Phe Asn Ser Ala Ile Gly Lys Ile Gln Asp Ser Leu Ser Ser
            915                 920                 925

Thr Ala Ser Ala Leu Gly Lys Leu Gln Asp Val Val Asn Gln Asn Ala
            930                 935                 940

Gln Ala Leu Asn Thr Leu Val Lys Gln Leu Ser Ser Asn Phe Gly Ala
945                 950                 955                 960

Ile Ser Ser Val Leu Asn Asp Ile Leu Ser Arg Leu Asp Pro Pro Glu
                965                 970                 975

Ala Glu Val Gln Ile Asp Arg Leu Ile Thr Gly Arg Leu Gln Ser Leu
            980                 985                 990

Gln Thr Tyr Val Thr Gln Gln Leu Ile Arg Ala Ala Glu Ile Arg Ala
            995                 1000                1005

Ser Ala Asn Leu Ala Ala Thr Lys Met Ser Glu Cys Val Leu Gly
            1010                1015                1020

Gln Ser Lys Arg Val Asp Phe Cys Gly Lys Gly Tyr His Leu Met
        1025                1030                1035

Ser Phe Pro Gln Ser Ala Pro His Gly Val Val Phe Leu His Val
        1040                1045                1050

Thr Tyr Val Pro Ala Gln Glu Lys Asn Phe Thr Thr Ala Pro Ala
        1055                1060                1065

Ile Cys His Asp Gly Lys Ala His Phe Pro Arg Glu Gly Val Phe
        1070                1075                1080

Val Ser Asn Gly Thr His Trp Phe Val Thr Gln Arg Asn Phe Tyr
        1085                1090                1095

Glu Pro Gln Ile Ile Thr Thr Asp Asn Thr Phe Val Ser Gly Asn
        1100                1105                1110

Cys Asp Val Val Ile Gly Ile Val Asn Asn Thr Val Tyr Asp Pro
        1115                1120                1125

Leu Gln Pro Glu Leu Asp Ser Phe Lys Glu Glu Leu Asp Lys Tyr
        1130                1135                1140

Phe Lys Asn His Thr Ser Pro Asp Val Asp Leu Gly Asp Ile Ser
        1145                1150                1155

Gly Ile Asn Ala Ser Val Val Asn Ile Gln Lys Glu Ile Asp Arg
        1160                1165                1170

Leu Asn Glu Val Ala Lys Asn Leu Asn Glu Ser Leu Ile
        1175                1180                1185
```

<210> SEQ ID NO 2
<211> LENGTH: 1273
<212> TYPE: PRT
<213> ORGANISM: SARS-CoV-2 coronavirus

<400> SEQUENCE: 2

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
```

```
            420              425              430
Val Ile Ala Trp Asn Ser Asn Leu Asp Ser Lys Val Gly Gly Asn
            435              440              445
Tyr Asn Tyr Leu Tyr Arg Leu Phe Arg Lys Ser Asn Leu Lys Pro Phe
        450              455              460
Glu Arg Asp Ile Ser Thr Glu Ile Tyr Gln Ala Gly Ser Thr Pro Cys
465              470              475              480
Asn Gly Val Glu Gly Phe Asn Cys Tyr Phe Pro Leu Gln Ser Tyr Gly
            485              490              495
Phe Gln Pro Thr Asn Gly Val Gly Tyr Gln Pro Tyr Arg Val Val Val
        500              505              510
Leu Ser Phe Glu Leu Leu His Ala Pro Ala Thr Val Cys Gly Pro Lys
    515              520              525
Lys Ser Thr Asn Leu Val Lys Asn Lys Cys Val Asn Phe Asn Phe Asn
    530              535              540
Gly Leu Thr Gly Thr Gly Val Leu Thr Glu Ser Asn Lys Lys Phe Leu
545              550              555              560
Pro Phe Gln Gln Phe Gly Arg Asp Ile Ala Asp Thr Thr Asp Ala Val
            565              570              575
Arg Asp Pro Gln Thr Leu Glu Ile Leu Asp Ile Thr Pro Cys Ser Phe
        580              585              590
Gly Gly Val Ser Val Ile Thr Pro Gly Thr Asn Thr Ser Asn Gln Val
        595              600              605
Ala Val Leu Tyr Gln Asp Val Asn Cys Thr Glu Val Pro Val Ala Ile
        610              615              620
His Ala Asp Gln Leu Thr Pro Thr Trp Arg Val Tyr Ser Thr Gly Ser
625              630              635              640
Asn Val Phe Gln Thr Arg Ala Gly Cys Leu Ile Gly Ala Glu His Val
            645              650              655
Asn Asn Ser Tyr Glu Cys Asp Ile Pro Ile Gly Ala Gly Ile Cys Ala
            660              665              670
Ser Tyr Gln Thr Gln Thr Asn Ser Pro Arg Arg Ala Arg Ser Val Ala
        675              680              685
Ser Gln Ser Ile Ile Ala Tyr Thr Met Ser Leu Gly Ala Glu Asn Ser
    690              695              700
Val Ala Tyr Ser Asn Asn Ser Ile Ala Ile Pro Thr Asn Phe Thr Ile
705              710              715              720
Ser Val Thr Thr Glu Ile Leu Pro Val Ser Met Thr Lys Thr Ser Val
            725              730              735
Asp Cys Thr Met Tyr Ile Cys Gly Asp Ser Thr Glu Cys Ser Asn Leu
            740              745              750
Leu Leu Gln Tyr Gly Ser Phe Cys Thr Gln Leu Asn Arg Ala Leu Thr
        755              760              765
Gly Ile Ala Val Glu Gln Asp Lys Asn Thr Gln Glu Val Phe Ala Gln
    770              775              780
Val Lys Gln Ile Tyr Lys Thr Pro Pro Ile Lys Asp Phe Gly Gly Phe
785              790              795              800
Asn Phe Ser Gln Ile Leu Pro Asp Pro Ser Lys Pro Ser Lys Arg Ser
            805              810              815
Phe Ile Glu Asp Leu Leu Phe Asn Lys Val Thr Leu Ala Asp Ala Gly
            820              825              830
Phe Ile Lys Gln Tyr Gly Asp Cys Leu Gly Asp Ile Ala Ala Arg Asp
        835              840              845
```

-continued

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

```
Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 3
<211> LENGTH: 1269
<212> TYPE: PRT
<213> ORGANISM: Bat coronavirus RaTG13

<400> SEQUENCE: 3

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ser
            20                  25                  30

Thr Arg Gly Val Tyr Tyr Pro Asp Lys Val Phe Arg Ser Ser Val Leu
        35                  40                  45

His Leu Thr Gln Asp Leu Phe Leu Pro Phe Ser Asn Val Thr Trp
50                  55                  60

Phe His Ala Ile His Val Ser Gly Thr Asn Gly Ile Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Pro Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Asp Ser Ile Val Arg Phe Pro Asn Ile Thr Asn Leu Cys
                325                 330                 335

Pro Phe Gly Glu Val Phe Asn Ala Thr Thr Phe Ala Ser Val Tyr Ala
            340                 345                 350
```

```
Trp Asn Arg Lys Arg Ile Ser Asn Cys Val Ala Asp Tyr Ser Val Leu
        355                 360                 365

Tyr Asn Ser Thr Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Thr Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Lys His Ile Asp Ala Lys Glu Gly Gly Asn
        435                 440                 445

Phe Asn Tyr Leu Tyr Arg Leu Phe Arg Lys Ala Asn Leu Lys Pro Phe
    450                 455                 460

Glu Arg Asp Ile Ser Thr Glu Ile Tyr Gln Ala Gly Ser Lys Pro Cys
465                 470                 475                 480

Asn Gly Gln Thr Gly Leu Asn Cys Tyr Tyr Pro Leu Tyr Arg Tyr Gly
                485                 490                 495

Phe Tyr Pro Thr Asp Gly Val Gly His Gln Pro Tyr Arg Val Val Val
            500                 505                 510

Leu Ser Phe Glu Leu Leu Asn Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Ala Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Arg Ser Val Ala Ser Gln Ser Ile
        675                 680                 685

Ile Ala Tyr Thr Met Ser Leu Gly Ala Glu Asn Ser Val Ala Tyr Ser
    690                 695                 700

Asn Asn Ser Ile Ala Ile Pro Thr Asn Phe Thr Ile Ser Val Thr Thr
705                 710                 715                 720

Glu Ile Leu Pro Val Ser Met Thr Lys Thr Ser Val Asp Cys Thr Met
                725                 730                 735

Tyr Ile Cys Gly Asp Ser Thr Glu Cys Ser Asn Leu Leu Leu Gln Tyr
            740                 745                 750

Gly Ser Phe Cys Thr Gln Leu Asn Arg Ala Leu Thr Gly Ile Ala Val
        755                 760                 765
```

```
Glu Gln Asp Lys Asn Thr Gln Glu Val Phe Ala Gln Val Lys Gln Ile
770                 775                 780

Tyr Lys Thr Pro Pro Ile Lys Asp Phe Gly Gly Phe Asn Phe Ser Gln
785                 790                 795                 800

Ile Leu Pro Asp Pro Ser Lys Pro Ser Lys Arg Ser Phe Ile Glu Asp
                805                 810                 815

Leu Leu Phe Asn Lys Val Thr Leu Ala Asp Ala Gly Phe Ile Lys Gln
                820                 825                 830

Tyr Gly Asp Cys Leu Gly Asp Ile Ala Ala Arg Asp Leu Ile Cys Ala
                835                 840                 845

Gln Lys Phe Asn Gly Leu Thr Val Leu Pro Pro Leu Leu Thr Asp Glu
850                 855                 860

Met Ile Ala Gln Tyr Thr Ser Ala Leu Leu Ala Gly Thr Ile Thr Ser
865                 870                 875                 880

Gly Trp Thr Phe Gly Ala Gly Ala Ala Leu Gln Ile Pro Phe Ala Met
                885                 890                 895

Gln Met Ala Tyr Arg Phe Asn Gly Ile Gly Val Thr Gln Asn Val Leu
                900                 905                 910

Tyr Glu Asn Gln Lys Leu Ile Ala Asn Gln Phe Asn Ser Ala Ile Gly
                915                 920                 925

Lys Ile Gln Asp Ser Leu Ser Ser Thr Ala Ser Ala Leu Gly Lys Leu
930                 935                 940

Gln Asp Val Val Asn Gln Asn Ala Gln Ala Leu Asn Thr Leu Val Lys
945                 950                 955                 960

Gln Leu Ser Ser Asn Phe Gly Ala Ile Ser Ser Val Leu Asn Asp Ile
                965                 970                 975

Leu Ser Arg Leu Asp Lys Val Glu Ala Glu Val Gln Ile Asp Arg Leu
                980                 985                 990

Ile Thr Gly Arg Leu Gln Ser Leu Gln Thr Tyr Val Thr Gln Gln Leu
                995                 1000                1005

Ile Arg Ala Ala Glu Ile Arg Ala Ser Ala Asn Leu Ala Ala Thr
                1010                1015                1020

Lys Met Ser Glu Cys Val Leu Gly Gln Ser Lys Arg Val Asp Phe
                1025                1030                1035

Cys Gly Lys Gly Tyr His Leu Met Ser Phe Pro Gln Ser Ala Pro
                1040                1045                1050

His Gly Val Val Phe Leu His Val Thr Tyr Val Pro Ala Gln Glu
                1055                1060                1065

Lys Asn Phe Thr Thr Ala Pro Ala Ile Cys His Asp Gly Lys Ala
                1070                1075                1080

His Phe Pro Arg Glu Gly Val Phe Val Ser Asn Gly Thr His Trp
                1085                1090                1095

Phe Val Thr Gln Arg Asn Phe Tyr Glu Pro Gln Ile Ile Thr Thr
                1100                1105                1110

Asp Asn Thr Phe Val Ser Gly Ser Cys Asp Val Val Ile Gly Ile
                1115                1120                1125

Val Asn Asn Thr Val Tyr Asp Pro Leu Gln Pro Glu Leu Asp Ser
                1130                1135                1140

Phe Lys Glu Glu Leu Asp Lys Tyr Phe Lys Asn His Thr Ser Pro
                1145                1150                1155

Asp Val Asp Leu Gly Asp Ile Ser Gly Ile Asn Ala Ser Val Val
                1160                1165                1170

Asn Ile Gln Lys Glu Ile Asp Arg Leu Asn Glu Val Ala Lys Asn
```

-continued

```
                1175                1180                1185
Leu Asn Glu Ser Leu Ile Asp Leu Gln Glu Leu Gly Lys Tyr Glu
        1190                1195                1200

Gln Tyr Ile Lys Trp Pro Trp Tyr Ile Trp Leu Gly Phe Ile Ala
        1205                1210                1215

Gly Leu Ile Ala Ile Ile Met Val Thr Ile Met Leu Cys Cys Met
        1220                1225                1230

Thr Ser Cys Cys Ser Cys Leu Lys Gly Cys Cys Ser Cys Gly Ser
        1235                1240                1245

Cys Cys Lys Phe Asp Glu Asp Ser Glu Pro Val Leu Lys Gly
        1250                1255                1260

Val Lys Leu His Tyr Thr
        1265

<210> SEQ ID NO 4
<211> LENGTH: 1353
<212> TYPE: PRT
<213> ORGANISM: MERS-related coronavirus

<400> SEQUENCE: 4

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser His Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270
```

```
Leu Tyr Gly Gly Asn Met Phe Gln Phe Ala Thr Leu Pro Val Tyr Asp
            275                 280                 285

Thr Ile Lys Tyr Tyr Ser Ile Ile Pro His Ser Ile Arg Ser Ile Gln
290                 295                 300

Ser Asp Arg Lys Ala Trp Ala Ala Phe Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
                340                 345                 350

Ser Phe Asp Val Glu Ser Gly Val Tyr Ser Val Ser Ser Phe Glu Ala
                355                 360                 365

Lys Pro Ser Gly Ser Val Val Glu Gln Ala Glu Gly Val Glu Cys Asp
370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
                420                 425                 430

Ile Ala Ser Asn Cys Tyr Ser Ser Leu Ile Leu Asp Tyr Phe Ser Tyr
                435                 440                 445

Pro Leu Ser Met Lys Ser Asp Leu Ser Val Ser Ser Ala Gly Pro Ile
                450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
                500                 505                 510

Glu Val Pro Gln Leu Val Asn Ala Asn Gln Tyr Ser Pro Cys Val Ser
                515                 520                 525

Ile Val Pro Ser Thr Val Trp Glu Asp Gly Asp Tyr Tyr Arg Lys Gln
                530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
                595                 600                 605

Tyr Gly Val Ser Gly Arg Gly Val Phe Gln Asn Cys Thr Ala Val Gly
                610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
                675                 680                 685

Tyr Ser Arg Ser Thr Arg Ser Met Leu Lys Arg Arg Asp Ser Thr Tyr
```

-continued

```
            690             695             700
Gly Pro Leu Gln Thr Pro Val Gly Cys Val Leu Gly Leu Val Asn Ser
705                 710             715                 720

Ser Leu Phe Val Glu Asp Cys Lys Leu Pro Leu Gly Gln Ser Leu Cys
            725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
            755                 760             765

Gln Val Asp Gln Leu Asn Ser Ser Tyr Phe Lys Leu Ser Ile Pro Thr
            770             775             780

Asn Phe Ser Phe Gly Val Thr Gln Glu Tyr Ile Gln Thr Thr Ile Gln
785             790             795                 800

Lys Val Thr Val Asp Cys Lys Gln Tyr Val Cys Asn Gly Phe Gln Lys
                805             810                 815

Cys Glu Gln Leu Leu Arg Glu Tyr Gly Gln Phe Cys Ser Lys Ile Asn
            820             825             830

Gln Ala Leu His Gly Ala Asn Leu Arg Gln Asp Asp Ser Val Arg Asn
            835             840             845

Leu Phe Ala Ser Val Lys Ser Ser Gln Ser Ser Pro Ile Ile Pro Gly
            850             855             860

Phe Gly Gly Asp Phe Asn Leu Thr Leu Leu Glu Pro Val Ser Ile Ser
865             870             875             880

Thr Gly Ser Arg Ser Ala Arg Ser Ala Ile Glu Asp Leu Leu Phe Asp
                885             890             895

Lys Val Thr Ile Ala Asp Pro Gly Tyr Met Gln Gly Tyr Asp Asp Cys
            900             905             910

Met Gln Gln Gly Pro Ala Ser Ala Arg Asp Leu Ile Cys Ala Gln Tyr
            915             920             925

Val Ala Gly Tyr Lys Val Leu Pro Pro Leu Met Asp Val Asn Met Glu
            930             935             940

Ala Ala Tyr Thr Ser Ser Leu Leu Gly Ser Ile Ala Gly Val Gly Trp
945             950             955             960

Thr Ala Gly Leu Ser Ser Phe Ala Ala Ile Pro Phe Ala Gln Ser Ile
                965             970             975

Phe Tyr Arg Leu Asn Gly Val Gly Ile Thr Gln Gln Val Leu Ser Glu
            980             985             990

Asn Gln Lys Leu Ile Ala Asn Lys Phe Asn Gln Ala Leu Gly Ala Met
            995             1000            1005

Gln Thr Gly Phe Thr Thr Thr Asn Glu Ala Phe Arg Lys Val Gln
    1010            1015            1020

Asp Ala Val Asn Asn Asn Ala Gln Ala Leu Ser Lys Leu Ala Ser
    1025            1030            1035

Glu Leu Ser Asn Thr Phe Gly Ala Ile Ser Ala Ser Ile Gly Asp
    1040            1045            1050

Ile Ile Gln Arg Leu Asp Val Leu Glu Gln Asp Ala Gln Ile Asp
    1055            1060            1065

Arg Leu Ile Asn Gly Arg Leu Thr Thr Leu Asn Ala Phe Val Ala
    1070            1075            1080

Gln Gln Leu Val Arg Ser Glu Ser Ala Ala Leu Ser Ala Gln Leu
    1085            1090            1095

Ala Lys Asp Lys Val Asn Glu Cys Val Lys Ala Gln Ser Lys Arg
    1100            1105            1110
```

Ser Gly Phe Cys Gly Gln Gly Thr His Ile Val Ser Phe Val Val
1115                1120                1125

Asn Ala Pro Asn Gly Leu Tyr Phe Met His Val Gly Tyr Tyr Pro
1130                1135                1140

Ser Asn His Ile Glu Val Val Ser Ala Tyr Gly Leu Cys Asp Ala
1145                1150                1155

Ala Asn Pro Thr Asn Cys Ile Ala Pro Val Asn Gly Tyr Phe Ile
1160                1165                1170

Lys Thr Asn Asn Thr Arg Ile Val Asp Glu Trp Ser Tyr Thr Gly
1175                1180                1185

Ser Ser Phe Tyr Ala Pro Glu Pro Ile Thr Ser Leu Asn Thr Lys
1190                1195                1200

Tyr Val Ala Pro Gln Val Thr Tyr Gln Asn Ile Ser Thr Asn Leu
1205                1210                1215

Pro Pro Pro Leu Leu Gly Asn Ser Thr Gly Ile Asp Phe Gln Asp
1220                1225                1230

Glu Leu Asp Glu Phe Phe Lys Asn Val Ser Thr Ser Ile Pro Asn
1235                1240                1245

Phe Gly Ser Leu Thr Gln Ile Asn Thr Thr Leu Leu Asp Leu Thr
1250                1255                1260

Tyr Glu Met Leu Ser Leu Gln Gln Val Val Lys Ala Leu Asn Glu
1265                1270                1275

Ser Tyr Ile Asp Leu Lys Glu Leu Gly Asn Tyr Thr Tyr Tyr Asn
1280                1285                1290

Lys Trp Pro Trp Tyr Ile Trp Leu Gly Phe Ile Ala Gly Leu Val
1295                1300                1305

Ala Leu Ala Leu Cys Val Phe Phe Ile Leu Cys Cys Thr Gly Cys
1310                1315                1320

Gly Thr Asn Cys Met Gly Lys Leu Lys Cys Asn Arg Cys Cys Asp
1325                1330                1335

Arg Tyr Glu Glu Tyr Asp Leu Glu Pro His Lys Val His Val His
1340                1345                1350

<210> SEQ ID NO 5
<211> LENGTH: 24
<212> TYPE: DNA
<213> ORGANISM: Artificial
<220> FEATURE:
<223> OTHER INFORMATION: MBK-175 KanR-fwd

<400> SEQUENCE: 5
caataatatt gaaaaggaa gagt                                              24

<210> SEQ ID NO 6
<211> LENGTH: 24
<212> TYPE: DNA
<213> ORGANISM: Artificial
<220> FEATURE:
<223> OTHER INFORMATION: MBK-176 KanR-rev

<400> SEQUENCE: 6
atgagtaaac ttggtctgac agtt                                             24

<210> SEQ ID NO 7
<211> LENGTH: 24
<212> TYPE: DNA
<213> ORGANISM: Artificial
<220> FEATURE:

<223> OTHER INFORMATION: MBK-177 A-pUC19-fwd

<400> SEQUENCE: 7
aactgtcaga ccaagtttac tcat                                        24

<210> SEQ ID NO 8
<211> LENGTH: 24
<212> TYPE: DNA
<213> ORGANISM: Artificial
<220> FEATURE:
<223> OTHER INFORMATION: MBK-178 A-pUC19-rev

<400> SEQUENCE: 8
actcttcctt tttcaatatt attg                                        24

<210> SEQ ID NO 9
<211> LENGTH: 47
<212> TYPE: DNA
<213> ORGANISM: Artificial
<220> FEATURE:
<223> OTHER INFORMATION: MBK-180 DS-tile1-fwd

<400> SEQUENCE: 9
gttcagagtt ctacagtccg acgatcacac gtggtgttta ttaccct               47

<210> SEQ ID NO 10
<211> LENGTH: 45
<212> TYPE: DNA
<213> ORGANISM: Artificial
<220> FEATURE:
<223> OTHER INFORMATION: MBK-181 DS-tile1-rev

<400> SEQUENCE: 10
ccttggcacc cgagaattcc acataagaaa aggctgagag acata                 45

<210> SEQ ID NO 11
<211> LENGTH: 47
<212> TYPE: DNA
<213> ORGANISM: Artificial
<220> FEATURE:
<223> OTHER INFORMATION: MBK-301 DS-tile2-fwd

<400> SEQUENCE: 11
gttcagagtt ctacagtccg acgatcctta gggaatttgt gtttaag               47

<210> SEQ ID NO 12
<211> LENGTH: 42
<212> TYPE: DNA
<213> ORGANISM: Artificial
<220> FEATURE:
<223> OTHER INFORMATION: MBK-302 DS-tile2-rev

<400> SEQUENCE: 12
ccttggcacc cgagaattcc aaacttcacc aaaagggcac aa                    42

<210> SEQ ID NO 13
<211> LENGTH: 47
<212> TYPE: DNA
<213> ORGANISM: Artificial
<220> FEATURE:
<223> OTHER INFORMATION: MBK-303DS-tile3-fwd

<400> SEQUENCE: 13
gttcagagtt ctacagtccg acgatcagga agagaatcag caactgt               47

```
<210> SEQ ID NO 14
<211> LENGTH: 43
<212> TYPE: DNA
<213> ORGANISM: Artificial
<220> FEATURE:
<223> OTHER INFORMATION: MBK-304 DS-tile3-rev

<400> SEQUENCE: 14
ccttggcacc cgagaattcc aatgattgta aaggaaagta aca            43

<210> SEQ ID NO 15
<211> LENGTH: 51
<212> TYPE: DNA
<213> ORGANISM: Artificial
<220> FEATURE:
<223> OTHER INFORMATION: MBK-305 DS-tile4-fwd

<400> SEQUENCE: 15
gttcagagtt ctacagtccg acgatcagta gtagtacttt cttttgaact t        51

<210> SEQ ID NO 16
<211> LENGTH: 44
<212> TYPE: DNA
<213> ORGANISM: Artificial
<220> FEATURE:
<223> OTHER INFORMATION: MBK-306 DS-tile4-rev

<400> SEQUENCE: 16
ccttggcacc cgagaattcc aggtgtaatg tcaagaatct caag           44

<210> SEQ ID NO 17
<211> LENGTH: 47
<212> TYPE: DNA
<213> ORGANISM: Artificial
<220> FEATURE:
<223> OTHER INFORMATION: MBK-307 DS-tile5-fwd

<400> SEQUENCE: 17
gttcagagtt ctacagtccg acgatcgact cactttcttc cacagca          47

<210> SEQ ID NO 18
<211> LENGTH: 42
<212> TYPE: DNA
<213> ORGANISM: Artificial
<220> FEATURE:
<223> OTHER INFORMATION: MBK-308 DS-tile5-rev

<400> SEQUENCE: 18
ccttggcacc cgagaattcc aagctctgat ttctgcagct ct             42

<210> SEQ ID NO 19
<211> LENGTH: 34
<212> TYPE: DNA
<213> ORGANISM: Artificial
<220> FEATURE:
<223> OTHER INFORMATION: PJS-P2192 pETCON-NK-BsaI-C-term-fwd

<400> SEQUENCE: 19
tgttatggag cgggtctcag ggggcggatc cgaa                 34

<210> SEQ ID NO 20
<211> LENGTH: 34
<212> TYPE: DNA
<213> ORGANISM: Artificial
<220> FEATURE:
<223> OTHER INFORMATION: PJS-P2193 pETCON-NK-BsaI-C-term-rev
```

```
<400> SEQUENCE: 20
acgttcagtg atggtctcta ctagcctgca gagc                          34

<210> SEQ ID NO 21
<211> LENGTH: 40
<212> TYPE: DNA
<213> ORGANISM: Artificial
<220> FEATURE:
<223> OTHER INFORMATION: PJS-P2194pETCON-NK-BsaI-N-term-fwd

<400> SEQUENCE: 21
tgttatggag cgggtctcac aggaactgac aactatatgc                    40

<210> SEQ ID NO 22
<211> LENGTH: 45
<212> TYPE: DNA
<213> ORGANISM: Artificial
<220> FEATURE:
<223> OTHER INFORMATION: PJS-P2195 pETCON-NK-BsaI-N-term-rev

<400> SEQUENCE: 22
acgttcagtg atggtctctg aaaatattga aaaacagcga agtaa              45

<210> SEQ ID NO 23
<211> LENGTH: 34
<212> TYPE: DNA
<213> ORGANISM: Artificial
<220> FEATURE:
<223> OTHER INFORMATION: PJS-P2206 S-1-fwd

<400> SEQUENCE: 23
accgtcctca gcgaattcgc caccatgttc gtct                          34

<210> SEQ ID NO 24
<211> LENGTH: 33
<212> TYPE: DNA
<213> ORGANISM: Artificial
<220> FEATURE:
<223> OTHER INFORMATION: PJS-P2207 S-1-rev

<400> SEQUENCE: 24
gctagaggct gacccgggag agtttgtctg ggt                           33

<210> SEQ ID NO 25
<211> LENGTH: 33
<212> TYPE: DNA
<213> ORGANISM: Artificial
<220> FEATURE:
<223> OTHER INFORMATION: PJS-P2208 S-2-fwd

<400> SEQUENCE: 25
ctcccgggtc agcctctagc gtggcctccc agt                           33

<210> SEQ ID NO 26
<211> LENGTH: 31
<212> TYPE: DNA
<213> ORGANISM: Artificial
<220> FEATURE:
<223> OTHER INFORMATION: PJS-P2209 S-2-rev

<400> SEQUENCE: 26
ataaagctgc tcttagaagg cttggatgga t                             31

<210> SEQ ID NO 27
<211> LENGTH: 31
```

```
<212> TYPE: DNA
<213> ORGANISM: Artificial
<220> FEATURE:
<223> OTHER INFORMATION: PJS-P2210 S-3-fwd

<400> SEQUENCE: 27
gccttctaag agcagcttta tcgaggacct g                          31

<210> SEQ ID NO 28
<211> LENGTH: 27
<212> TYPE: DNA
<213> ORGANISM: Artificial
<220> FEATURE:
<223> OTHER INFORMATION: PJS-P2211 S-3-rev

<400> SEQUENCE: 28
ctgcctctgg agggtccagc cggctca                               27

<210> SEQ ID NO 29
<211> LENGTH: 27
<212> TYPE: DNA
<213> ORGANISM: Artificial
<220> FEATURE:
<223> OTHER INFORMATION: PJS-P2212 S-4-fwd

<400> SEQUENCE: 29
gctggaccct ccagaggcag aggtgca                               27

<210> SEQ ID NO 30
<211> LENGTH: 28
<212> TYPE: DNA
<213> ORGANISM: Artificial
<220> FEATURE:
<223> OTHER INFORMATION: PJS-P2213 S-4-rev

<400> SEQUENCE: 30
aagcggccgc tgggccactt gatgtact                              28

<210> SEQ ID NO 31
<211> LENGTH: 24
<212> TYPE: DNA
<213> ORGANISM: Artificial
<220> FEATURE:
<223> OTHER INFORMATION: PJS-P2214 vec-fwd

<400> SEQUENCE: 31
gtgttacaac caattaacca attc                                  24

<210> SEQ ID NO 32
<211> LENGTH: 34
<212> TYPE: DNA
<213> ORGANISM: Artificial
<220> FEATURE:
<223> OTHER INFORMATION: PJS-P2215 vec-rev

<400> SEQUENCE: 32
gcgaattcgc tgaggacggt tatccacaga atca                       34

<210> SEQ ID NO 33
<211> LENGTH: 59
<212> TYPE: DNA
<213> ORGANISM: Artificial
<220> FEATURE:
<223> OTHER INFORMATION: PJS-P2221 S-K41NAAC

<400> SEQUENCE: 33
```
cttcaccaga ggcgtgtact atcctgacaa cgtgtttaga agctccgtgc tgcactcta    59

<210> SEQ ID NO 34
<211> LENGTH: 59
<212> TYPE: DNA
<213> ORGANISM: Artificial
<220> FEATURE:
<223> OTHER INFORMATION: PJS-P2222 S-K41P-CCC

<400> SEQUENCE: 34
cttcaccaga ggcgtgtact atcctgaccc cgtgtttaga agctccgtgc tgcactcta    59

<210> SEQ ID NO 35
<211> LENGTH: 59
<212> TYPE: DNA
<213> ORGANISM: Artificial
<220> FEATURE:
<223> OTHER INFORMATION: PJS-P2223 S-K41S-AGC

<400> SEQUENCE: 35
cttcaccaga ggcgtgtact atcctgacag cgtgtttaga agctccgtgc tgcactcta    59

<210> SEQ ID NO 36
<211> LENGTH: 59
<212> TYPE: DNA
<213> ORGANISM: Artificial
<220> FEATURE:
<223> OTHER INFORMATION: PJS-P2224 S-Q115H-CAC

<400> SEQUENCE: 36
ctttggcacc acactggact ccaagacaca ctctctgctg atcgtgaaca atgccacca    59

<210> SEQ ID NO 37
<211> LENGTH: 92
<212> TYPE: DNA
<213> ORGANISM: Artificial
<220> FEATURE:
<223> OTHER INFORMATION: PJS-P2225 S-Q115H-CAC-V126F-TTC

<400> SEQUENCE: 37
ctttggcacc acactggact ccaagacaca ctctctgctg atcgtgaaca atgccaccaa   60
cttcgtcatc aaggtgtgcg agttccagtt tt                                 92

<210> SEQ ID NO 38
<211> LENGTH: 59
<212> TYPE: DNA
<213> ORGANISM: Artificial
<220> FEATURE:
<223> OTHER INFORMATION: PJS-P2226 S-V126F-TTC

<400> SEQUENCE: 38
tctgctgatc gtgaacaatg ccaccaactt cgtcatcaag gtgtgcgagt tccagtttt    59

<210> SEQ ID NO 39
<211> LENGTH: 59
<212> TYPE: DNA
<213> ORGANISM: Artificial
<220> FEATURE:
<223> OTHER INFORMATION: PJS-P2227 S-C166A-GCC

<400> SEQUENCE: 39
gtttagagtg tattctagcg ccaacaacgc cacatttgag tacgtgagcc agcctttcc    59

<210> SEQ ID NO 40
<211> LENGTH: 59

```
<212> TYPE: DNA
<213> ORGANISM: Artificial
<220> FEATURE:
<223> OTHER INFORMATION: PJS-P2228 S-T167F-TTC

<400> SEQUENCE: 40
tagagtgtat tctagcgcca acaactgctt ctttgagtac gtgagccagc ctttcctga      59

<210> SEQ ID NO 41
<211> LENGTH: 59
<212> TYPE: DNA
<213> ORGANISM: Artificial
<220> FEATURE:
<223> OTHER INFORMATION: PJS-P2229 S-F168Q-CAG

<400> SEQUENCE: 41
agtgtattct agcgccaaca actgcacaca ggagtacgtg agccagcctt tcctgatgg      59

<210> SEQ ID NO 42
<211> LENGTH: 59
<212> TYPE: DNA
<213> ORGANISM: Artificial
<220> FEATURE:
<223> OTHER INFORMATION: PJS-P2230 S-P230F-TTC

<400> SEQUENCE: 42
cagcgccctg gagcccctgg tggatctgtt catcggcatc aacatcaccc ggtttcaga      59

<210> SEQ ID NO 43
<211> LENGTH: 59
<212> TYPE: DNA
<213> ORGANISM: Artificial
<220> FEATURE:
<223> OTHER INFORMATION: PJS-P2231 S-Q314Y-TAC

<400> SEQUENCE: 43
gtcctttacc gtggagaagg gcatctatta cacatccaat ttcagggtgc agccaaccg      59

<210> SEQ ID NO 44
<211> LENGTH: 59
<212> TYPE: DNA
<213> ORGANISM: Artificial
<220> FEATURE:
<223> OTHER INFORMATION: PJS-P2232 S-V407M-ATG

<400> SEQUENCE: 44
cgattctttc gtgatcaggg gcgacgagat gcgccagatc gccccggcc agacaggca      59

<210> SEQ ID NO 45
<211> LENGTH: 59
<212> TYPE: DNA
<213> ORGANISM: Artificial
<220> FEATURE:
<223> OTHER INFORMATION: PJS-P2233 S-A411I-ATC

<400> SEQUENCE: 45
gatcaggggc gacgaggtgc gccagatcat ccccggccag acaggcaaga tcgcagact      59

<210> SEQ ID NO 46
<211> LENGTH: 59
<212> TYPE: DNA
<213> ORGANISM: Artificial
<220> FEATURE:
<223> OTHER INFORMATION: PJS-P2234 S-A522T-ACC

<400> SEQUENCE: 46
```
gctgagcttt gagctgctgc acgccccaac cacagtgtgc ggccccaaga agtccacca    59

<210> SEQ ID NO 47
<211> LENGTH: 55
<212> TYPE: DNA
<213> ORGANISM: Artificial
<220> FEATURE:
<223> OTHER INFORMATION: PJS-P2235 S-K528F-TTC

<400> SEQUENCE: 47
gcacgcccca gcaacagtgt gcggccectt caagtccacc aatctggtga agaac    55

<210> SEQ ID NO 48
<211> LENGTH: 59
<212> TYPE: DNA
<213> ORGANISM: Artificial
<220> FEATURE:
<223> OTHER INFORMATION: JS-P2236 S-F543M-ATG

<400> SEQUENCE: 48
ggtgaagaac aagtgcgtga acttcaacat gaacggcctg accggcacag gcgtgctga    59

<210> SEQ ID NO 49
<211> LENGTH: 52
<212> TYPE: DNA
<213> ORGANISM: Artificial
<220> FEATURE:
<223> OTHER INFORMATION: PJS-P2237 S-N544I-ATC

<400> SEQUENCE: 49
aagtgcgtga acttcaactt catcggcctg accggcacag gcgtgctgac cg    52

<210> SEQ ID NO 50
<211> LENGTH: 59
<212> TYPE: DNA
<213> ORGANISM: Artificial
<220> FEATURE:
<223> OTHER INFORMATION: PJS-P2238 S-F565A-GCC

<400> SEQUENCE: 50
caacaagaag ttcctgccat ttcagcaggc cggcagggac atcgcagata ccacagacg    59

<210> SEQ ID NO 51
<211> LENGTH: 59
<212> TYPE: DNA
<213> ORGANISM: Artificial
<220> FEATURE:
<223> OTHER INFORMATION: PJS-P2239 S-P579T-ACC

<400> SEQUENCE: 51
cgcagatacc acagacgccg tgcgcgacac ccagaccctg gagatcctgg acatcacac    59

<210> SEQ ID NO 52
<211> LENGTH: 59
<212> TYPE: DNA
<213> ORGANISM: Artificial
<220> FEATURE:
<223> OTHER INFORMATION: PJS-P2240 S-Q580F-TTC

<400> SEQUENCE: 52
agataccaca gacgccgtgc gcgacccatt caccctggag atcctggaca tcacaccct    59

<210> SEQ ID NO 53
<211> LENGTH: 59
<212> TYPE: DNA
<213> ORGANISM: Artificial

```
<220> FEATURE:
<223> OTHER INFORMATION: PJS-P2241 S-I973N-AAC

<400> SEQUENCE: 53
gaagcagctg agcagcaact tcggcgccaa ctctagcgtg ctgaatgaca tcctgagcc      59

<210> SEQ ID NO 54
<211> LENGTH: 59
<212> TYPE: DNA
<213> ORGANISM: Artificial
<220> FEATURE:
<223> OTHER INFORMATION: PJS-P2242 S-L984R-AGA

<400> SEQUENCE: 54
tagcgtgctg aatgacatcc tgagccggag agaccctcca gaggcagagg tgcagatcg      59

<210> SEQ ID NO 55
<211> LENGTH: 4
<212> TYPE: PRT
<213> ORGANISM: Artificial Sequence
<220> FEATURE:
<223> OTHER INFORMATION: GSAS Mutation

<400> SEQUENCE: 55

Gly Ser Ala Ser
1
```

STABILIZING MUTANTS OF PREFUSION SARS-COV-2 (COVID-19) SPIKE PROTEIN AND IMPROVED YEAST SURFACE DISPLAY ENGINEERING PLATFORM FOR THE SAME

CROSS-REFERENCE TO RELATED APPLICATIONS

This application claims the benefit of and priority to U.S. Provisional Application No. 63/026,316 filed May 18, 2020, and U.S. Provisional Application No. 63/062,123 filed Aug. 6, 2020. The entire specifications and figures of the above-referenced applications are hereby incorporated, in their entirety, by reference.

GOVERNMENT INTEREST

This invention was made with government support under grant number AI141452 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 12, 2021, is named "90245-00532-Sequence-Listing-AF.txt" and is 52.5 Kbytes in size.

TECHNICAL FIELD

The inventive technology relates to modified viral fusion proteins having enhanced stability characteristics that may be useful for vaccine formulation, serological diagnostic testing, and enhancement of expression titers.

BACKGROUND

Figure 1:
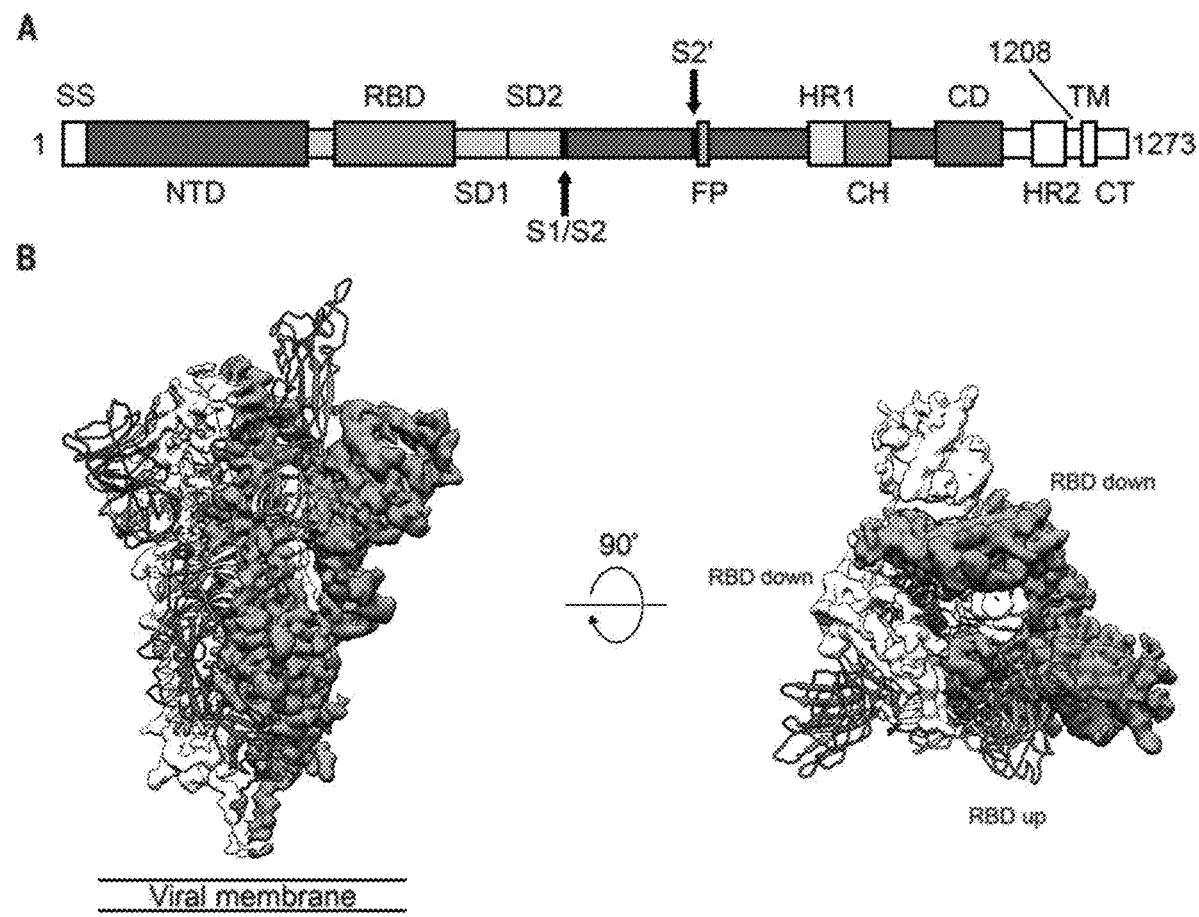
Figure 2:
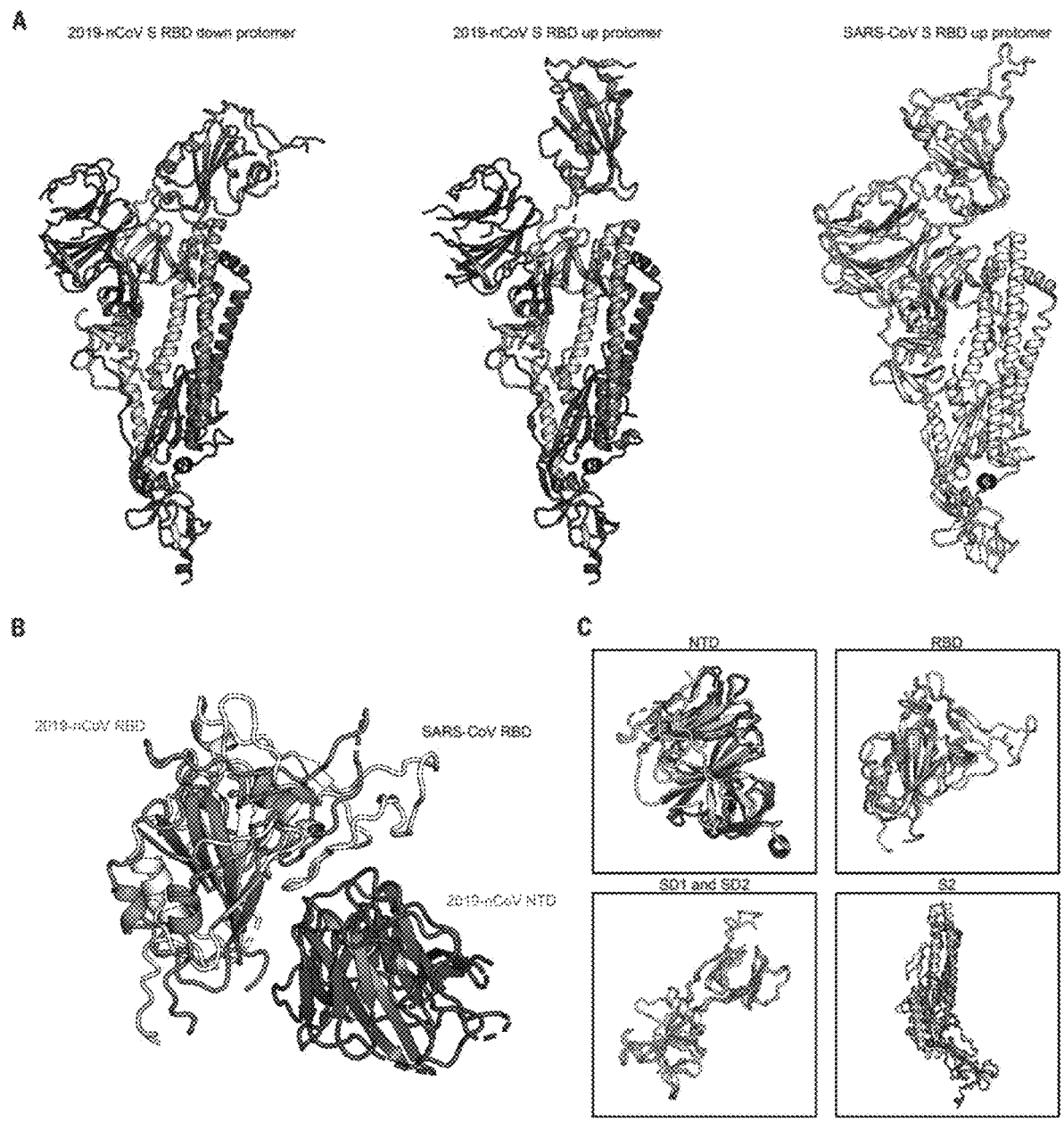

Severe acute respiratory syndrome coronavirus 2 (SARS-CoV-2) is the fifth known circulating human coronavirus and, to date, has caused hundreds of thousands of deaths worldwide. A major antigenic determinant of SARS-CoV-2 is the Spike(S) protein (referred to herein as "Spike," "S protein," or "Spike protein") which is a type I viral fusion protein. A furin cleavage site separates each S subunit and after cleavage the subunits are noncovalently associated in the prefusion metastable structure. The $S_1$ subunit binds to angiotensin-converting enzyme 2 (ACE2) via its receptor binding domain (RBD), while the $S_2$ subunit is critical for the fusion of the viral and host cell membranes. As shown in FIGS. 1-2, prefusion state the RBD of each S monomer transitions between an 'up' conformation able to bind ACE2 and a 'down' conformation in which binding to ACE2 and other potent neutralizing antibodies are sterically blocked. As can be appreciated, the conformational structure of the viral immunogen can be essential for vaccine efficacy. Notably, the majority of identified SARS-CoV-2 neutralizing antibodies (nAbs) target the RBD and many selectively recognize the 'up' S conformation. This conformational selectivity suggests that engineered spike proteins that preferentially adopt the 'up' conformation would make valuable reagents for vaccination and serological diagnosis. We therefore aimed to identify mutations that further stabilize the SARS-CoV-2 spike protein in its 'up' prefusion conformation. For example, recent phase I clinical trials of RSV show effective neutralizing antibody titers only for an engineered immunogen comprising three mutations that lock in the prefusion state of the RSF fusion protein F. Similarly, preclinical work on the related coronavirus MERS show that two proline mutations in the CH domain (P987-988) stabilized the prefusion state in an 'up' conformation. In fact, one exemplary RNA SARS-CoV-2 vaccine currently in Phase I clinical trials utilizes similar stabilizing P987-988 mutations. Other common mutations include modulation of the protease cleavage site between S1 & S2. Even with these mutations, cryo-EM structures with the proline mutations show only 20-35% of the protomers engaged in the 'up' conformation.

Stabilization of the prefusion state can also be essential to improve expression yields in recombinant hosts. The expression yields of the Spike construct are typically in the 0.5-20 mg/L scale among different laboratories in mammalian suspension culture, which is about 10-1,000-fold worse than for well expressing proteins. Engineered prefusion Spike protein is currently being used as an antigenic reagent for serological diagnostics to estimate community seroprevalence. However, there is not enough biomanufacturing capacity in the world to produce enough Spike protein for the billions of diagnostic tests required for population-wide weekly testing. As such, there exists a need to identify additional mutations which could further stabilize the 'up' prefusion conformation of Spike. Such novel stabilizing mutations may further improve expression yields in recombinant systems. This is important, as most engineering platforms for viral proteins involve low-throughput 96 well screens or mammalian cell display, which is also time-intensive. However, yeast surface display is an alternative eukaryotic display system where a protein of interest may be displayed from the surface via fusion to the cell mating protein Aga2p. For example, a large custom library of Spike protein variants can be transformed into *Saccharomyces cerevisiae* and screened by fluorescence activated cell sorting (FACS). Advantages of yeast screening are the high-throughput nature and the relatively fast time for screening. Yeast display systems are generally known in the art and have been used for stabilizing proteins. As generally described in by Wittrup et al., U.S. Pat. Nos. 6,699,658 and 6,696,251, Rakestraw et al., PCT/US2008/003978; all of which are incorporated herein by reference. However, type I viral fusion proteins have not been demonstrated to successfully display on the yeast surface, most likely because the growth and induction medium are not optimized to maintain viral proteins in their prefusion conformations. As such, there also exists a need to develop systems, methods and growth and induction medium compositions to facilitate the use of type I viral fusion proteins in yeast-based expression systems.

SUMMARY OF THE INVENTION

The present invention relates to one or more novel type I viral fusion protein fragments or variants thereof, having one or more stabilizing mutations suitable for use as vaccines against infections with coronaviruses, such as MERS or SARS-CoV-2.

Another aspect of the present invention relates to compositions comprising the one or more novel type I viral fusion proteins, or a fragment or variant thereof, having one or more stabilizing mutations for the preparation of a pharmaceutical composition, especially a vaccine, e.g. for use in the prophylaxis or treatment of viral infections, and preferably infection by a coronavirus such as MERS or SARS-CoV-2. Another aspect of the present invention relates to one or more novel type I viral fusion proteins, or a fragment or variant thereof, having one or more stabilizing mutations suitable for use in nucleic-acid vaccines against infections with coronaviruses, such as MERS or SARS-CoV-2. Another aspect of the present invention relates to compositions comprising the one or more nucleic acids encoding a novel type I viral fusion protein having one or more stabilizing mutations for the preparation of a pharmaceutical composition, especially a vaccine, e.g. for use in the prophylaxis or treatment of viral infections, and preferably infection by a coronavirus such as MERS or SARS-CoV-2.

Another aspect of the present invention relates to one or more novel type I viral fusion proteins, or a fragment or variant thereof, having one or more stabilizing mutations suitable for use in an RNA vaccines against infections with coronaviruses, such as MERS or SARS-CoV-2, and preferably a non-self-replicating RNA vaccine. Another aspect of the present invention relates to compositions comprising the one or more RNAs encoding a novel type I viral fusion protein having one or more stabilizing mutations for the preparation of a pharmaceutical composition, especially a vaccine, e.g. for use in the prophylaxis or treatment of viral infections, and preferably infection by a coronavirus such as MERS or SARS-CoV-2. Another aspect of the present invention relates to one or more novel type I viral fusion proteins, or a fragment or variant thereof, having one or more stabilizing mutations suitable for use in an RNA vaccines against infections with coronaviruses, such as MERS or SARS-CoV-2, and preferably a self-replicating RNA vaccine.

Another aspect of the present invention relates to compositions comprising the one or more self-replicating RNAs encoding a novel type I viral fusion protein as well as other features that may allow self-replication inside a target host cell. For example, in one aspect a self-replicating RNA vaccine of the invention may encode a novel type I viral fusion protein (among other antigenic peptides in the case of a multi-valent vaccine) as well as a 5' cap, a 5' untranslated region, a 3' untranslated region and a Poly-A and/or Poly-C tail region.

Another aspect of the invention includes methods of preventing and/or treating a viral infection by administering a therapeutically effective amount of one or more compositions of the invention to a subject in need thereof, and preferably one or more of the vaccine compositions described herein. Another aspect of the invention further relates to systems and methods of producing and screening one or more novel type I viral fusion proteins, or fragments or variants thereof, having one or more stabilizing mutations. Another aspect of the invention further relates to systems and methods of increasing expression titers of one or more novel type I viral fusion proteins, or fragments or variants thereof, having one or more stabilizing mutations in recombinant, or even cell free protein expression systems. Another aspect of the invention further relates to systems and methods of displaying one or more novel type I viral fusion proteins, or fragments or variants thereof, on the surface of a yeast cell, such as *S. cerevisiae* or *P. Pastoris* and the like. Certain aspects of this invention may further include novel growth and induction medium compositions to facilitate the use of type I viral fusion proteins, or a fragments or variants thereof, in yeast-based surface display and expression systems.

Another aspect of the invention relates to systems, methods, and compositions for the design and use of one or more novel type I viral fusion proteins, or fragments or variants thereof, having one or more stabilizing mutations suitable for use in molecular diagnostic tests, and preferably diagnostic tests configured to identify to viral pathogens, such as coronaviruses, and preferably as MERS or SARS-CoV-2. Another aspect of the invention relates to one or more novel stabilized Spike proteins, or fragments or variants thereof, having one or more stabilizing mutations suitable for use as vaccines against infections with coronaviruses, such as MERS or SARS-CoV-2. As used herein, the term "stabilized," or "stabilizing mutation" with reference to a proteins, and in particular a type I viral fusion protein such as the Spike protein from SARS-CoV-2 as compared to the relative unfolded state of the protein, is understood to mean that the mutation may tend to stabilize the protein in the prefusion 'up' conformation compared to a wild-type version of the same.

Another aspect of the invention relates to one or more novel stabilized Spike proteins, or fragments or variants thereof, having one or more mutations that stabilize SARS-CoV-2 Spike in the prefusion 'up' conformation. Another aspect of the present invention relates to nucleic acid compositions encoding one or more novel stabilized Spike proteins suitable for use as vaccines against infections with coronaviruses, such as MERS or SARS-CoV-2. Additionally, the present invention relates to nucleic acid compositions encoding one or more novel stabilized Spike proteins from SARS-CoV-2 for the preparation of a pharmaceutical composition, especially a vaccine, e.g. for use in the prophylaxis or treatment of coronavirus infections, such as MERS or SARS-CoV-2. Another aspect of the present invention relates to one or more novel stabilized Spike proteins, or fragments or variants thereof, having one or more stabilizing mutations suitable for use in nucleic-acid vaccines against infections with coronaviruses, such as MERS or SARS-CoV-2. Another aspect of the present invention relates to compositions comprising the one or more nucleic acids encoding a novel stabilized Spike proteins, or fragments or variants thereof having one or more stabilizing mutations for the preparation of a pharmaceutical composition, especially a vaccine, e.g. for use in the prophylaxis or treatment of viral infections, and preferably infection by a coronavirus such as MERS or SARS-CoV-2.

Another aspect of the present invention relates to one or more novel stabilized Spike proteins, or fragments or variants thereof, having one or more stabilizing mutations suitable for use in an RNA vaccine against infections with coronaviruses, such as MERS or SARS-CoV-2, and preferably a non-self-replicating RNA vaccine. Another aspect of the present invention relates to compositions comprising the one or more RNAs encoding novel stabilized Spike proteins, or fragments or variants thereof, having one or more stabilizing mutations for the preparation of a pharmaceutical composition, especially a vaccine, e.g., for use in the prophylaxis or treatment of viral infections, and preferably infection by a coronavirus such as MERS or SARS-CoV-2. Another aspect of the present invention relates to one or more novel stabilized Spike proteins, or a fragment or variant thereof, having one or more stabilizing mutations suitable for use in an RNA vaccine against infections with coronaviruses, such as MERS or SARS-CoV-2, and preferably a self-replicating RNA vaccine. Another aspect of the present invention relates to compositions comprising the one or more self-replicating RNAs encoding novel stabilized Spike proteins, or fragments or variants thereof, as well as other features that may allow self-replication inside a target host cell. For example, in one aspect a self-replicating RNA vaccine of the invention may encode novel stabilized Spike proteins, or fragments or variants thereof (among other antigenic peptides in the case of a multi-valent vaccine) as well as a 5' cap, a 5' untranslated region, a 3' untranslated region and a Poly-A and/or Poly-C tail region.

Another aspect of the invention includes methods of preventing and/or treating a viral infection by administering a therapeutically effective amount of one or more compositions of the invention to a subject in need thereof, and preferably one or more of the vaccine compositions described herein. Another aspect of the invention further relates to systems and methods of producing and screening one or more novel stabilized Spike proteins, or fragments or variants thereof, having one or more stabilizing mutations. Another aspect of the invention further relates to systems and methods of increasing expression titers of one or more novel stabilized Spike proteins, or fragments or variants thereof, having one or more stabilizing mutations in recombinant, or even cell free protein expression systems. Another aspect of the invention further relates to systems and methods of displaying one or more novel stabilized Spike proteins, or fragments or variants thereof, on the surface of a yeast cell, such as S. cerevisiae or P. Pastoris and the like. Certain aspects of this invention may further include, novel growth and induction medium compositions to facilitate the use of stabilized Spike proteins, or fragments or variants thereof, in yeast-based surface display and expression systems.

Another aspect of the invention relates to systems, methods, and compositions for the design and use of one or more novel stabilized Spike proteins, or fragments or variants thereof, having one or more stabilizing mutations suitable for use in molecular diagnostic tests, and preferably diagnostic tests configured to identify to viral pathogens, such as coronaviruses, and preferably as MERS or SARS-CoV-2. Another aspect of the invention relates to nucleic acid compositions, including both DNA and RNA nucleic acids, encoding novel stabilized Spike proteins, or fragments or variants thereof, wherein said Spike protein is derived from a coronavirus, and preferably a MERS or SARS-CoV-2 coronavirus. Another aspect of the invention relates to nucleic acid compositions encoding novel stabilized Spike proteins, or fragments or variants thereof, according to SEQ ID NOs: 1-3, and further include one or more mutations at the positions identified in Table 1A below. Another aspect of the invention relates to nucleic acid compositions encoding novel stabilized Spike proteins, or fragments or variants thereof, according to SEQ ID NOs: 1-3, and further including one or more mutations identified in Table 1 below. Another aspect of the invention relates to nucleic acid compositions encoding novel stabilized Spike proteins, or fragments or variants thereof, according to SEQ ID NOs: 1-3, and further include one or more mutations identified in Table 1 below, and further including variants wherein the mutated residue is replaced with an acceptable or compatible amino acid residue, wherein said acceptable or compatible amino acid residue also stabilizes the Spike protein in the prefusion 'up' configuration.

Additional aspects of the inventive technology will become apparent from the specification, figures and claims below.

BRIEF DESCRIPTION OF THE FIGURES

FIG. 1. (A) Schematic of 2019-nCoV S primary structure colored by domain. (SS, signal sequence; S2', S2' protease cleavage site; FP, fusion peptide; HR1, heptad repeat 1; CH, central helix; CD, connector domain; HR2, heptad repeat 2; TM, transmembrane domain; CT, cytoplasmic tail. Arrows denote protease cleavage sites). (B) Side and top views of the prefusion structure of the SARS-CoV-2 S protein with a single RBD in the up conformation. The two RBD down protomers are shown as cryo-EM density in either white or gray and the RBD up protomer is shown in ribbons colored corresponding to the schematic in (A).

FIG. 2. (A) Single protomer of 2019-nCoV (SARS-CoV-2) S with the RBD in the down conformation (left) is shown in ribbons colored according to FIG. 1. A protomer of 2019-nCoV (SARS-CoV-2) S in the RBD up conformation is shown (center) next to a protomer of SARS-CoV S in the RBD up conformation (right), displayed as ribbons and colored white (PDB ID: 6CRZ). (B) RBDs of 2019-nCoV (SARS-CoV-2) and SARS-CoV aligned based on the position of the adjacent NTD from the neighboring protomer. The 2019-nCoV (SARS-CoV-2) RBD is colored green and the SARS-CoV RBD is colored white. The 2019-nCoV (SARS-CoV-2) NTD is colored blue. (C) Structural domains from 2019-nCoV (SARS-CoV-2) S have been aligned to their counterparts from SARS-CoV S as follows: NTD (top left), RBD (top right), SD1 and SD2 (bottom left), and S2 (bottom right).

FIG. 3. (A) Spike ectodomain schematic with labeled and colored boundaries. NTD: N-terminal domain, RBD: receptor-binding domain, RBM: receptor-binding motif, SD1: subdomain 1, SD2: subdomain 2, $S_1/S_2$: furin cleavage site, $S_2'$: $S_2'$ cleavage site, HR1: heptad repeat 1, CH: central helix, CD: connector domain, HR2: heptad repeat 2. (B) Volcano plots used to identify the hits for both hACE2-Fc and CR3022 with hits that are shared. (C) Venn diagram comparing the hits found for hACE2-Fc and CR3022 with 25 being shared. (D) Prefusion spike trimer shown with domains colored as they are in A. RBD is shown in the up conformation and along with SD1 and SD2 is shown on the same spike monomer. The NTD and $S_2$ subunits are shown on a neighboring monomer. Oligo pool mutated residues are represented as spheres. (E) Identical spike prefusion structure show in D but with the 25 hits shown as spheres instead of showing all oligo pool mutations. (F) Reaction coordinate and interaction of variant N544L in the spike ectodomain showing this mutation globally stabilizes the prefusion spike protein. (G) Reaction coordinate and interaction of identified hit A372N in the spike ectodomain which destabilizes the down protomer.

FIG. 4. Overview of yeast display constructs used in screening S ectodomain libraries.

FIG. 5. pH time course experiments for yeast display induction medium SGCAA and M37G. Three biological replicates (circles, squares, triangles) of *S. cerevisiae* EBY100 pS_Ecto_Nterm were induced in M37G or SGCAA. The pH of each culture was monitored for approximately 24 hours. Lines are guides for the eye. Error bars for each biological replicate are shown as 1 s.d. for 3 technical replicates.

FIG. 6. Yeast surface display optimization for wildtype SARS-CoV-2 spike ectodomain. FITC signal (RFU), FITC signal to noise ratio, as well as PE signal (RFU) and PE signal to noise ratio for both ACE2-Fc and CR3022 are shown for biological replicates of spike ectodomain are shown for with differing media, induction temperatures, and orientation of Spike relative to Aga2p. Libraries were screened using the condition highlighted in yellow.

FIG. 7. Overview of oligo pool mutagenesis performed on fragmented spike plasmids and subsequent assembly of the pUC19-S-ecto-Nterm library.

FIG. 8. Location of next generation sequencing performed on the S ectodomain. Each tile can be covered using 250 bp paired end Illumina sequencing.

Figure 9:
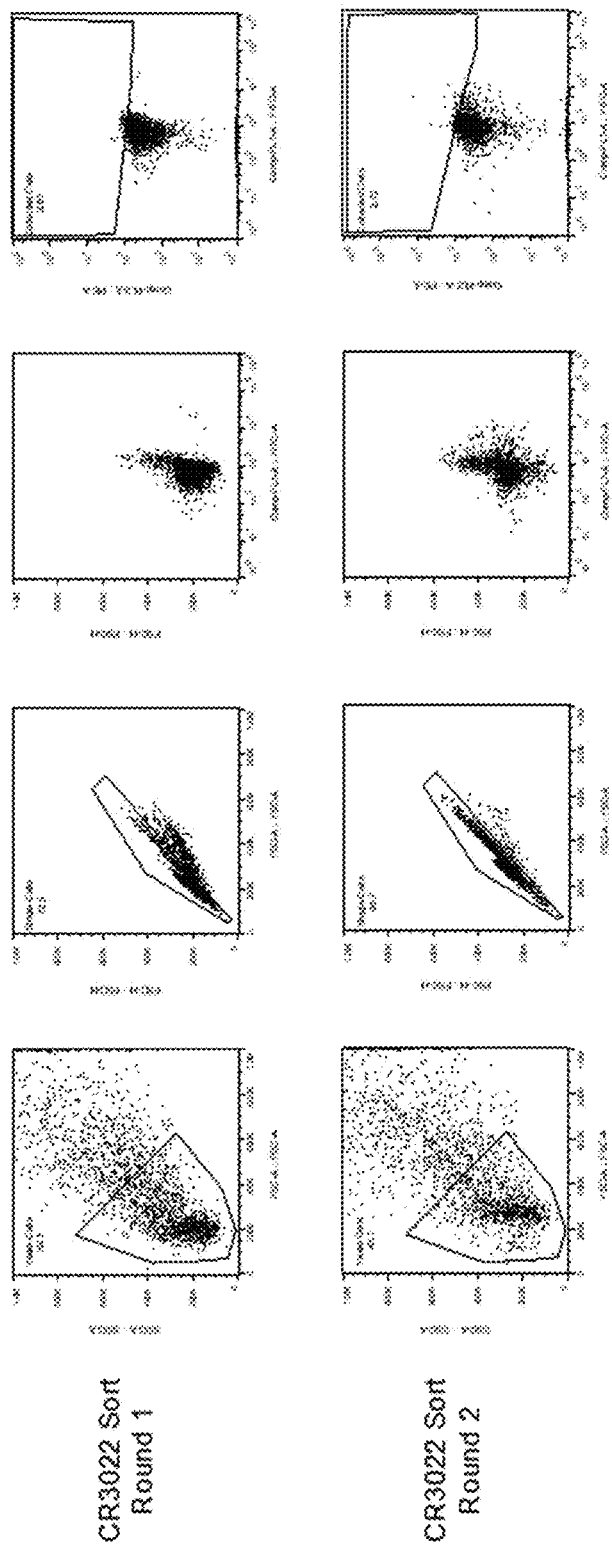

FIG. 9. Sample cytograms for library sorts with CR3022. Cytograms for the first and second round of sorting of S ectodomain N-term libraries labeled with 500 nM biotinylated CR3022. The gates used for sorting the library with CR3022 are shown above. Two gates were set to capture individual yeast cells. A third gate (rightmost panel) was set to collect the top 1% of cells displaying full-length S ectodomain using an anti-cmyc FITC and bound to biotinylated CR3022 using streptavidin-phyoerythrin (PE).

Figure 10:
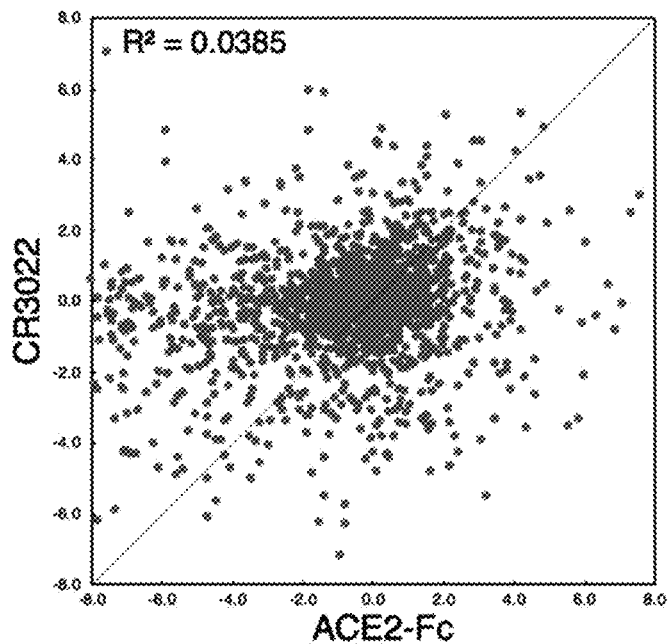
Figure 10:
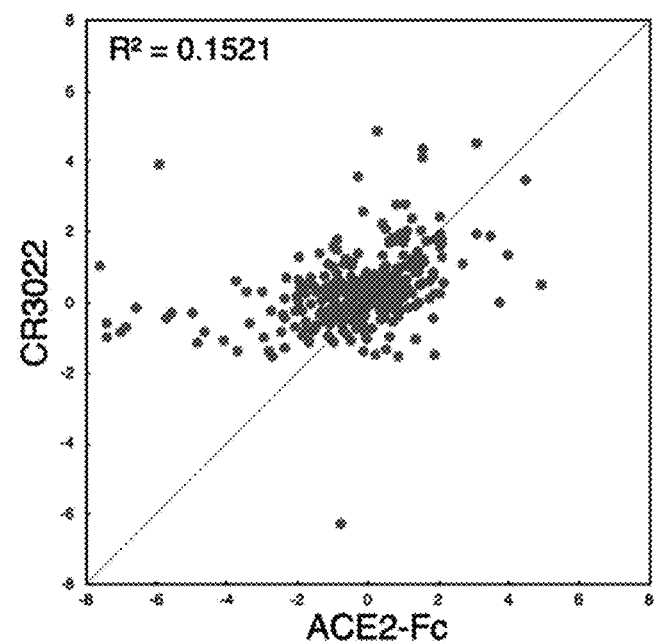

FIG. 10. Correlations between normalized enrichment values for ACE2-Fc and CR3022. Axis labels correspond to normalized enrichment values for a given binding protein. R2 values shown in upper left-hand corner. The R2 correlation improves to 0.15 for tile 4 which contains the overwhelming majority of the gain of function mutations. Dashed line y=x is included for reference.

Figure 11:
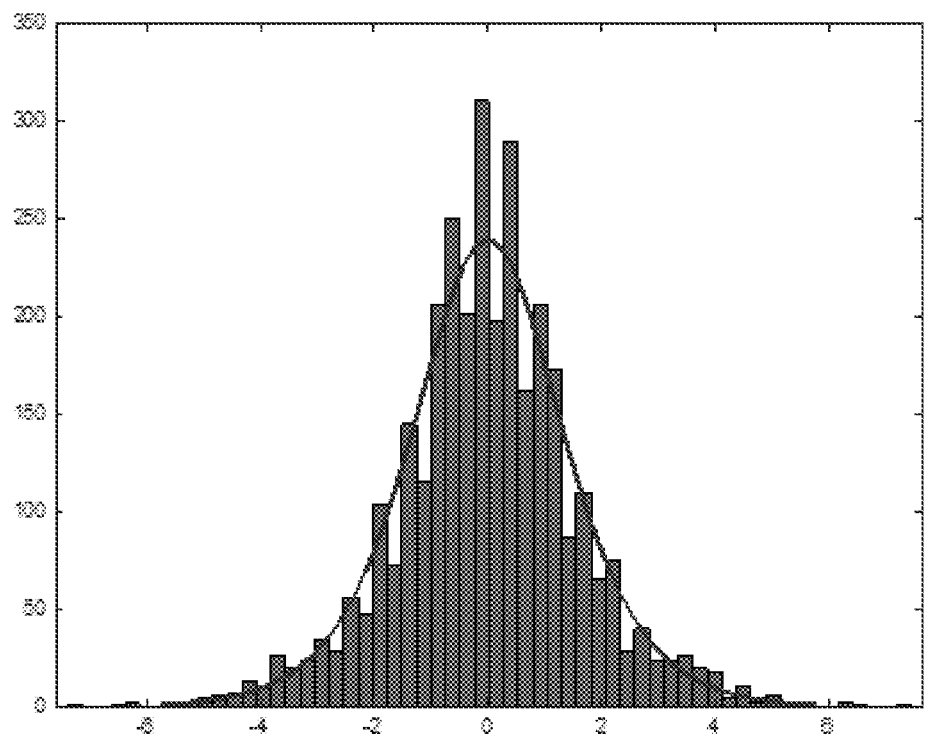

FIG. 11. The logistic function of the diagram has the following parameters: mu=0 sigma=0.875509

Figure 12:
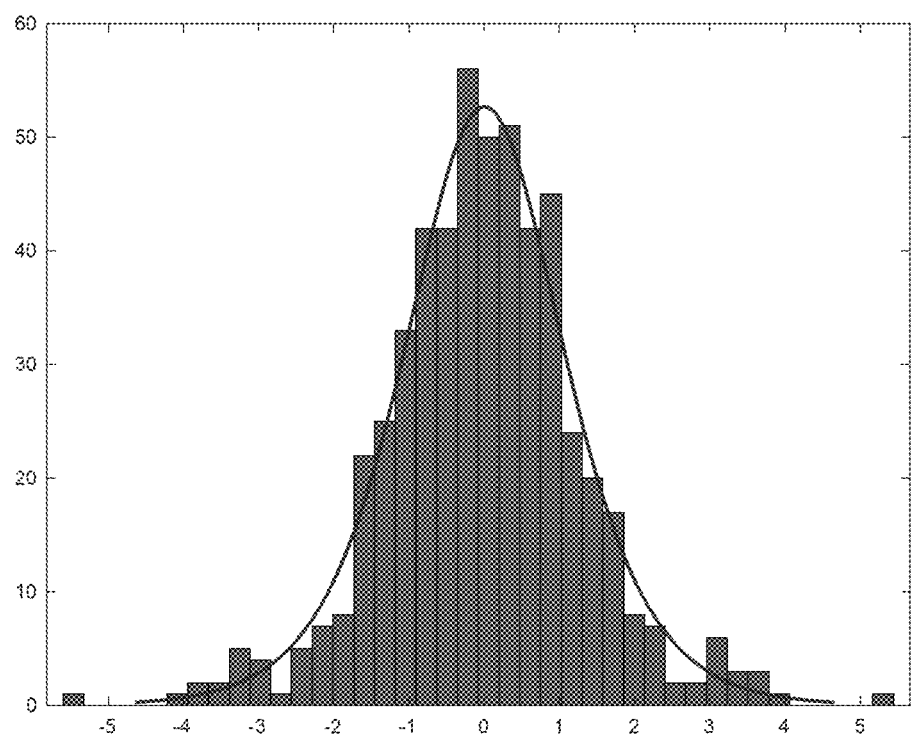

FIG. 12. The logistic function of the diagram has the following parameters: mu=0 sigma=0.704308

DETAILED DESCRIPTION OF THE INVENTION

The inventive technology described herein includes one or more mutations that stabilize SARS-Cov-2 Spike in the prefusion 'up' conformation. As detailed herein, these stabilizing mutations, identified in Table 1 below, were identified computationally and screened using a novel pipeline involving yeast surface display and deep sequencing. As used herein, the terms "SARS-Cov-2", "SARS-Cov-2 coronavirus" or "COVID-19" relate to positive-sense, single-stranded RNA viruses of the genus β-coronavirus, which typically cause a condition referred to as "Severe acute respiratory syndrome" or "SARS". As used herein, the terms "Middle East respiratory syndrome coronavirus", "MERS coronavirus" or "MERS-CoV" relate to positive-sense, single-stranded RNA viruses of the genus β-coronavirus (lineage C), which typically cause a condition referred to as "Middle East respiratory syndrome" or "MERS". According to a preferred embodiment, the novel stabilized Spike proteins according to the invention include the antigenic peptide of a Spike protein of a SARS coronavirus, and preferably a SARS-CoV-2, as described herein, or a fragment or variant thereof. In specific embodiments, SARS-CoV-2 Spike protein according to SEQ ID NOs: 1-3 is modified in such a way that the prototypical prefusion conformation is stabilized. Stabilization of the prefusion conformation is preferably obtained by introducing one or more stabilization mutations identified at a residue position identified in Table 1A. In a preferred embodiment, stabilization of the prefusion conformation is preferably obtained by introducing one or more stabilization mutations identified in Table 1. Specifically, stabilized Spike proteins are obtained in a way that the amino acid residue at one or more of the positions identified in Table 1A, is exchanged with a different amino acid. So, for example, in one embodiment the Cysteine (C) reside at position 166 of the Spike protein is exchanged with an Alanine (A) and is identified herein as stabilizing mutation C166A. According to one preferred embodiment, the stabilization mutations identified in Table 1 may be, in some embodiments, complementary to additional stabilization mutations. For example, the amino acid sequence according to SEQ ID NO: 1 includes two additional complementary stabilization mutations, specifically two consecutive proline substitutions at residues 987 and 988 in the full length Spike protein according to SEQ ID NO: 2. For example, the amino acid sequence according to SEQ ID NO: 1 includes an additional stabilization mutation, specifically a substitution according to SEQ ID NO: 55 at residues 682-685 of the furin cleavage site of the full length Spike protein according to SEQ ID NO: 2.

As described herein, mutation notations are numbered with respect to their positions within the amino acid sequence of a wild-type version of a Spike protein, for example as provided in the amino acid sequence according to SEQ ID NO: 2. As a result, in this example the amino acid sequence according to SEQ ID NO: 1 encoding the Initial Spike Ectodomain, the first amino acid in said sequence is initially numbered as residue 13, such that exemplary mutation C166A would occur at reside 166 as compared to the wildtype amino acid sequence. For the avoidance of doubt, if the mutation C166A were identified in SEQ ID NO: 1, and the first residue were identified as residue number 1, then the mutation would alternatively be referred to as C154A—the two being equivalent. As such, all mutations reference with respect to SEQ ID NOs: 1 and/or 2, may be equivalently positioned regardless of the specific residue referenced herein.

The inventive technology described herein includes one or more nucleic acids encoding a SARS-CoV-2 Spike protein having one or more stabilizing mutations that stabilize the peptide in the prefusion 'up' conformation. According to a preferred embodiment, the nucleic acid compositions encoding one or more novel stabilized Spike proteins include DNA sequence encoding the antigenic peptide of a Spike protein of a SARS coronavirus, and preferably a SARS-CoV-2, as described herein, or a fragment or variant thereof. In specific embodiments, the DNA compositions of the invention encode a SARS-CoV-2 Spike protein according to amino acid sequences identified in SEQ ID NOs: 1-3, wherein the encoded amino acid sequence is modified in such a way that the prototypical prefusion conformation is stabilized. Stabilization of the prefusion conformation is preferably obtained by modifying the DNA coding sequence to encode one or more stabilization mutations identified at a residue position identified in Table 1A. In a preferred embodiment, the DNA coding sequences may be modified to encode one or more stabilization mutations identified in Table 1 below. According to another preferred embodiment, the nucleic acid compositions encoding one or more novel stabilized Spike proteins include an RNA sequence encoding the antigenic peptide of a Spike protein of a SARS coronavirus, and preferably a SARS-CoV-2, as described herein, or a fragment or variant thereof. In specific embodiments, the RNA compositions of the invention encode a SARS-CoV-2 Spike protein according to amino acid sequences identified in SEQ ID NOs: 1-3, wherein the encoded amino acid sequence is modified in such a way that the prototypical prefusion conformation is stabilized. Stabilization of the prefusion conformation is preferably obtained by modifying the DNA coding sequence to encode one or more RNAs, or directly generating a RNA, that when translated may generate stabilization mutations identified at a residue position identified in Table 1A. In a preferred embodiment, the RNA sequences may be modified to encode one or more stabilization mutations identified in Table 1 below.

The nucleic acid compositions encoding one or more novel stabilized Spike proteins of a SARS coronavirus, and preferably a SARS-CoV-2, or fragments or variants thereof, may further be operably linked to a promoter generating an expression vector for producing a stabilized Spike protein. According to a preferred embodiment, the one or more expression vectors encoding a novel stabilized Spike proteins according to SEQ ID NOs: 1-3, or a fragment or variant thereof may be operably linked to a promoter, and further include one or more mutations at the positions identified in Table 1A below. In another embodiment, the one or more expression vectors encoding novel stabilized Spike proteins according to SEQ ID NOs: 1-3, or fragments or variants thereof, may further include one or more mutations identified in Table 1 below. In one preferred embodiment, an expression vector may be configured to heterologously express a stabilized Spike protein in a recombinant system. In one preferred embodiment, an expression vector may be configured to heterologously express a stabilized Spike protein in a yeast expression system. In another preferred embodiment, an expression vector may be configured to heterologously express a stabilized Spike protein in a human subject. In another preferred embodiment, an expression vector may be configured to heterologously express a stabilized Spike protein in a cell-free expression system.

Notably, in these embodiments, the expression vectors, and nucleic acid sequences generally described herein, may be codon optimized for expression in a target host, such as a human subject, or a yeast-based expression system for example. In addition, the expression vectors, and nucleic acid sequences generally described herein, may be configured with promoters configured to drive expression in a target system, such a yeast specific promoter that may drive expression of a stabilized Spike proteins in a yeast expression system, or a bacterial specific promoter that may drive expression of a stabilized Spike proteins in a bacterial expression system and the like. Additional embodiments of the invention include systems, methods and compositions for the heterologous expression and presentation of one or more type I viral fusion proteins on the surface of a yeast cell. In this embodiment, yeast expression vector may be configured to express type I viral fusion protein, such as a Spike protein from SARS-CoV-2 (SEQ ID NO: 1-3) or MERS (SEQ ID NO: 4), may be fused with an Aga2p peptide. Notably, in traditional yeast display systems, the protein of interest is C-terminally fused with Aga2p, in the following general configuration:

Promoter-AGA2P Signal Peptide-AGA2 Protein-
Protein of Interest-Epitope Tag-Terminator In the novel yeast display system described herein, an expression vector may be configured to express the protein of interest, in this case the stabilized type I viral fusion protein, to be C-terminally fused with a Aga2p signal peptide and N-terminally fused with Aga2p, having the following general configuration:

Promoter-AGA2P Signal Peptide-Type I Viral Fusion
Protein-AGA2P protein-Epitope tag-Terminator In this configuration, the type I fusion protein may be heterologously expressed in a yeast cell and through the action of the Aga2p peptide and signal sequence, incorporated into the cell wall and displayed on the surface of the yeast cell. Additional embodiments of the invention include systems, methods and compositions for the heterologous expression and presentation of one or more stabilized Spike proteins on the surface of a yeast cell. In this embodiment, a yeast expression vector may be configured to express a Spike protein according to SEQ ID NOs: 1-3, one or more stabilizing mutations at the positions identified in Table 1A, and/or one or more stabilizing mutations identified in Table 1. The yeast expression vector may be further configured to express the stabilized Spike protein being fused to a signal peptide and protein, and more specifically, the stabilized Spike protein, to be C-terminally fused with a Aga2p signal peptide and N-terminally fused with Aga2p, having the following general configuration:

Promoter (GAL1)-Aga2p Signal Peptide-Stabilized Spike
Protein-Aga2p protein-Epitope tag-Terminator In this configuration, the stabilized Spike protein may be heterologously expressed in a yeast cell and through the action of the Aga2p peptide and signal sequence, incorporated into the cell wall and displayed on the surface of the yeast cell. In this embodiment, a stabilized Spike protein may be displayed on the surface of the yeast cell in the prefusion 'up' configuration, which, as noted above allows the Spike to bind to ACE2, as opposed to the 'down' configuration which prevents binding to ACE2 sterically blocks neutralizing antibodies. In this configuration, the stabilized Spike protein may be used to produce and isolate Spike proteins, as well as development of more effective neutralizing antibodies specifically directed to the Spike in the 'up' configuration, among other diagnostic and molecular assays, such as serological testing, known in the field. As noted above, type I viral fusion proteins like Spike protein from SARS-CoV-2 have not been demonstrated to successfully display on yeast surface, most likely because the growth and induction medium are not optimized to maintain viral proteins in their prefusion conformations. To address this, certain embodiments of the invention further include systems, methods, and growth and induction medium compositions to facilitate the use of type I viral fusion proteins yeast-based expression systems.

According to one preferred embodiment, the inventive technology includes a novel yeast surface media composition including one or more of the following components:
a quantity of a sugar to promote yeast growth, and preferably dextrose;
a quantity a sugar to promote yeast induction, and preferably galactose;
a quantity of a nitrogen base, and preferably ammonium sulfate
a quantity of amino acids and/or small peptides, and preferably casamino acids;
a quantity of one or more acids, and preferably citric acid and/or phosphoric acid;
a quantity of buffer, and preferably MES buffer; and
a quantity of one or more pH adjustor to bring the solution to a pH of 7, and preferably NaOH and/or KOH.

According to another preferred embodiment, the inventive technology includes a novel yeast surface media composition including one or more of the following components, in the following exemplary quantities:
20 g/L dextrose or galactose;
6.7 g/L yeast nitrogen base with ammonium sulfate (Sigma Y0626);
5 g/L casamino acids (Bacto 223120, Technical grade);
50 mM citric acid;
50 mM phosphoric acid;
80 mM MES; and
Adjusted to pH 7 with 90% NaOH/10% KOH solution.

Naturally, such quantities and ratios are exemplary only to one or more preferred embodiments of the invention generally.

The present invention provides a nucleic acid, such as a DNA or RNA, comprising at least one coding region encoding one or more polypeptides comprising or consisting of an antigenic peptide or protein derived from SARS-CoV-2, or a fragment or variant thereof as described herein. In a preferred embodiment, the present invention provides an mRNA encoding stabilized Spike protein derived from SARS-CoV-2, or a fragment or variant thereof as described herein. Accordingly, in one embodiment the invention comprises an antigenic Spike protein peptide derived from SARS-CoV-2 having one or more stabilizing mutations according to Table 1, wherein the stabilizing mutations are configured stabilize Spike in the prefusion 'up' conformation. Accordingly, in one embodiment the invention comprises an antigenic Spike protein peptide derived from SARS-CoV-2 having one or more stabilizing mutations at a position according to Table 1A, wherein mutations at the stabilizing mutation positions are configured stabilize Spike in the prefusion 'up' conformation.

Accordingly, the antigenic peptide of the invention comprises at least one amino acid sequence according to SEQ ID NOs: 1-4, wherein the respective amino acid sequences according to SEQ ID NOs: 1-4 are modified by including at least one stabilizing mutation at a residue position identified in Table 1A, or a fragment or variant thereof. Accordingly, the nucleic acid of the invention comprises at least one coding region comprising or consisting of a DNA sequence encoding an amino acid sequence according to SEQ ID NOs: 1-4, wherein the respective amino acid sequences according to SEQ ID NOs: 1-4 are modified by including at least one stabilizing mutation identified in Table 1, or a fragment or variant thereof. Accordingly, the mRNA of the invention comprises at least one coding region comprising or consisting of an RNA sequence encoding an amino acid sequence according to SEQ ID NOs: 1-4, wherein the respective amino acid sequences according to SEQ ID NOs: 1-4 are modified by including at least one stabilizing mutation at a residue position identified in Table 1A, or a fragment or variant thereof.

Accordingly, the antigenic peptide of the invention comprises at least one amino acid sequence according to SEQ ID NOs: 1-4, wherein the respective amino acid sequences according to SEQ ID NOs: 1-4 are modified by including at least one stabilizing mutation identified in Table 1, or a fragment or variant thereof. Accordingly, the nucleic acid of the invention comprises at least one coding region comprising or consisting of a DNA sequence encoding an amino acid sequence according to SEQ ID NOs: 1-4, wherein the respective amino acid sequences according to SEQ ID NOs: 1-4 are modified by including at least one stabilizing mutation identified in Table 1, or a fragment or variant thereof. Accordingly, the mRNA of the invention comprises at least one coding region comprising or consisting of an RNA sequence encoding an amino acid sequence according to SEQ ID NOs: 1-4, wherein the respective amino acid sequences according to SEQ ID NOs: 1-4 are modified by including at least one stabilizing mutation identified in Table 1, or a fragment or variant thereof.

One preferred aspect of the inventive technology includes a novel vaccine for the SARS-CoV-2 coronavirus. In one preferred aspect, the inventive technology includes a novel amino acid or mRNA sequence comprising a coding region, encoding at least one stabilized Spike protein from SARS-CoV-2 coronavirus or a fragment or variant thereof. In one embodiment, the vaccine of the invention may be a protein, DNA, or RNA based vaccine. Further, the vaccine of the invention may be mono-valent, or multi-valent such that the stabilized Spike protein from SARS-CoV-2 coronavirus or a fragment or variant thereof may be co-expressed with one or more antigenic peptides. In a preferred embodiment, the novel vaccine may include a multi-valent vaccine configured to include one or more components, such as a stabilized Spike protein that may elicit a broad immune response in a subject, as well as complementary portions that may be configured to provide a specific antigenic response to the COVID-19 response through the production of specific neutralizing antibodies. For example, major capsid proteins have been established as the broad vaccine target for HPV, flavivirus and picornaviruses. Previous clinical and preclinical development of SARS and MERS vaccines confirm the high potential of coronavirus S1 subunit as a viable vaccine target. S1 includes the receptor-binding domain (RBD) that through its receptor-binding motif (RBM) binds (human) cell receptors and mediates human cell infection. Preclinical animal studies have demonstrated that MERS and SARS CoV S vaccines induce S-specific neutralizing antibodies that play a key role in preventing infection. The importance of S-neutralizing antibodies is further confirmed by animal studies with monoclonal antibodies or nanobodies targeting MERS or SARS CoV S protein. Moreover, nucleic-based MERS-CoV S1 and SARS-CoV S1 vaccines have been shown to induce humoral and cellular immune responses including neutralizing antibodies and protect against infection in diverse animal models.

In a preferred embodiment, the nucleic acid vaccine composition according to the invention comprises at least one DNA or RNA coding region encoding at least one antigenic peptide or protein comprising or consisting of a Spike protein from a coronavirus, or a fragment or variant thereof, which comprises or consists of an amino acid sequence selected from any one of the amino acid sequences according to SEQ ID NO: 1-4, or a fragment or variant of any one of these amino acid sequences. More preferably, the at least one encoded antigenic peptide or protein comprises or consists of an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with any one of the amino acid sequences according to SEQ ID NO: 1-4. In this embodiment, the Spike protein may preferably be a stabilized Spike protein having one or more mutations that stabilize Spike in the prefusion 'up' conformation. In a preferred embodiment, the nucleic acid vaccine according to the invention comprises at least one DNA or RNA coding region encoding at least one antigenic peptide or protein comprising or consisting of a stabilized SARS-CoV-2 coronavirus Spike protein, or a fragment or variant thereof, which comprises or consists of an amino acid sequence selected from any one of the amino acid sequences according to SEQ ID NO: 1-3 having one or more stabilizing mutations that stabilize Spike in the prefusion 'up' conformation, or a fragment or variant of any one of these amino acid sequences. More preferably, the at least one encoded antigenic peptide or protein comprises or consists of an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with any one of the amino acid sequences according to SEQ ID NO: 1-3.

In a preferred embodiment, the amino acid vaccine composition according to the invention comprises at least one DNA or RNA coding region encoding at least one antigenic peptide or protein comprising or consisting of a Spike protein from a coronavirus, or a fragment or variant thereof, which comprises or consists of an amino acid sequence selected from any one of the amino acid sequences according to SEQ ID NO: 1-4, or a fragment or variant of any one of these amino acid sequences. More preferably, the at least one encoded antigenic peptide or protein comprises or consists of an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with any one of the amino acid sequences according to SEQ ID NO: 1-4. In this embodiment, the Spike protein may preferably be a stabilized Spike protein having one or more mutations that stabilize Spike in the prefusion 'up' conformation.

In a preferred embodiment the invention may include a novel COVID-19 vaccine incorporating a stabilized Spike protein. In one embodiment, the vaccine may be a DNA-based vaccine, a protein-based vaccine, or an RNA vaccine, such as a self-replicating mRNA vaccine. In this preferred embodiment, the COVID-19 vaccine of the invention may include at least:

a 5' cap;
a 5' untranslated region (UTR);
a Spike protein from SARS-CoV-2 according to SEQ ID NOs: 1-3, having at least one stabilizing mutation according to Table 1, or at least one stabilizing mutation at a position according to Table 1A;
optionally one or more additional antigenic peptides, and preferably from SARS-CoV-2;
a 3' untranslated region (UTR); and
polyA and/or comprises a poly-C tail;
or a fragment or variant of any of the above.

In further embodiments, the present invention provides a composition comprising the nucleic acid or peptide-based COVID-19 vaccine of the invention, and at least one pharmaceutically acceptable carrier. A "vaccine" is typically understood to be a prophylactic or therapeutic material providing at least one epitope of an antigen, preferably an immunogen. "Providing at least one epitope" means, for example, that the vaccine comprises the epitope (or antigen comprising or providing said epitope) or that the vaccine comprises a molecule that, e.g., encodes the epitope or an antigen comprising or providing the epitope. The antigen preferably stimulates the adaptive immune system to provide an adaptive immune response. The (pharmaceutical) composition or vaccine provided herein may further comprise at least one pharmaceutically acceptable excipient, adjuvant, or further component (e.g. additives, auxiliary substances, and the like). In preferred embodiments, the (pharmaceutical) composition or vaccine according to the invention comprises a plurality or more than one of the inventive stabilized Spike proteins configured to be in their prefusion "up" configuration as described herein.

In a preferred embodiment of the composition according to the invention, at least one mRNA encoding a stabilized Spike protein according to the invention, and preferably a COVID-19 mRNA vaccine incorporating a stabilized Spike protein, is complexed with one or more cationic or polycationic compounds, preferably with cationic or polycationic polymers, cationic or polycationic peptides or proteins, e.g. protamine, cationic or polycationic polysaccharides and/or cationic or polycationic lipids. According to a preferred embodiment, the at least one mRNA of the composition according to the present invention, and preferably a COVID-19 mRNA vaccine incorporating a stabilized Spike protein, may be complexed with lipids to form one or more liposomes, lipoplexes, or lipid nanoparticles. Therefore, in one embodiment, the inventive composition comprises liposomes, lipoplexes, and/or lipid nanoparticles comprising the at least one mRNA. In this context, the terms "complexed" or "associated" refer to the essentially stable combination of said mRNA with one or more of the aforementioned compounds into larger complexes or assemblies without covalent binding. According to some preferred embodiments, the mRNA, optionally comprised by the (pharmaceutical) composition or vaccine, is complexed or associated with lipids (in particular cationic and/or neutral lipids) to form one or more liposomes, lipoplexes, lipid nanoparticles or nanoliposomes.

Preferably, lipid nanoparticles (LNPs) comprise: (a) at least one mRNA, and preferably a COVID-19 mRNA vaccine having a stabilized Spike protein, optionally comprised by the (pharmaceutical) composition or vaccine as defined herein, (b) a cationic lipid, (c) an aggregation reducing agent (such as polyethylene glycol (PEG) lipid or PEG-modified lipid), (d) optionally a non-cationic lipid (such as a neutral lipid), and (e) optionally, a sterol. In the context of the present invention, the term "lipid nanoparticle", also referred to as "LNP", is not restricted to any particular morphology, and includes any morphology generated when a cationic lipid and optionally one or more further lipids are combined, e.g. in an aqueous environment and/or in the presence of an RNA. For example, a liposome, a lipid complex, a lipoplex, an emulsion, a micelle, a lipidic nanocapsule, a nanosuspension and the like are within the scope of a lipid nanoparticle (LNP). In some embodiments, LNPs comprise, in addition to the at least one mRNA, and preferably a COVID-19 mRNA vaccine incorporating a stabilized Spike protein, optionally comprised by the (pharmaceutical) composition or vaccine as defined herein, (i) at least one cationic lipid; (ii) a neutral lipid; (iii) a sterol, e.g., cholesterol; and (iv) a PEG-lipid, in a molar ratio of about 20-60% cationic lipid: 5-25% neutral lipid: 25-55% sterol; 0.5-15% PEG-lipid.

In some embodiments, the inventive mRNA, and preferably a COVID-19 mRNA vaccine having a stabilized Spike protein, optionally comprised by the (pharmaceutical) composition or vaccine, may be formulated in an aminoalcohol lipidoid. Aminoalcohol lipidoids which may be used in the present invention may be prepared by the methods described in U.S. Pat. No. 8,450,298, herein incorporated by reference in its entirety. LNPs may include any cationic lipid suitable for forming a lipid nanoparticle. Preferably, the cationic lipid carries a net positive charge at about physiological pH. The cationic lipid may be an amino lipid. As used herein, the term "amino lipid" is meant to include those lipids having one or two fatty acid or fatty alkyl chains and an amino head group (including an alkylamino or dialkylamino group) that may be protonated to form a cationic lipid at physiological pH.

The cationic lipid may be, for example, N,N-dioleyl-N,N-dimethylammonium chloride (DODAC), N,N-distearyl-N,N-dimethylammonium bromide (DDAB), 1,2-dioleoyltrimethyl ammonium propane chloride (DOTAP) (also known as N-(2,3-dioleoyloxy) propyl)-N,N,N-trimethylammonium chloride and 1,2-Dioleyloxy-3-trimethylaminopropane chloride salt), N-(1-(2,3-dioleyloxy) propyl)-N,N,N-trimethylammonium chloride (DOTMA), N,N-dimethyl-2,3-dioleyloxy) propylamine (DODMA), 1,2-DiLinoleyloxy- N,N-dimethylaminopropane. (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Ci), 1,2-Dilinoleoyi-3-trimethylaminopropane chloride salt (DLin-TAP.CI), 1,2-Dilinoleyloxy-3-(N-methylpiperazino) propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DM A), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta [d][1,3]dioxol-5-amine, (6Z,9Z,28Z,31Z)-heptatriaconta-6,9,28,31-tetraen-19-yl 4-(dimethylamino) butanoate (MC3), 1,1'-(2-(4-(2-((2-(bis(2-hydroxydodecyl)amino)ethyl) (2-hydroxydodecyl)amino)ethyl) piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin--DMA), (6Z,9Z,28Z,31Z)-heptatriaconta-6,9,28,31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31Z)-heptatriaconta-6,9,28,31-tetraen-19-yloxy)-N,N-dimethylbutan-1-amine (MC4 Ether), or any combination of any of the foregoing. Other cationic lipids include, but are not limited to, N,N-distearyl-N,N-dimethylammonium bromide (DDAB), 3P-(N-(N',N'-dimethylaminoethane)-carbamoyl) cholesterol (DC-Choi), N-(1-(2,3-dioleyloxy) propyl)-N-2-(sperminecarboxamido) ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). Other suitable (cationic) lipids are disclosed in WO2009/086558, WO2009/127060, WO2010/048536, WO2010/054406, WO2010/088537, WO2010/129709, WO2011/153493, US2011/0256175, US2012/0128760, US2012/0027803, and U.S. Pat. No. 8,158,601. In that context, the disclosures of WO2009/086558, WO2009/127060, WO2010/048536, WO2010/054406, WO2010/088537, WO2010/129709, WO2011/153493, US2011/0256175, US2012/0128760, US2012/0027803, and U.S. Pat. No. 8,158,601 are incorporated herewith by reference. In some aspects the lipid may be selected from the group consisting of 98N12-5, C12-200, and ckk-E12.

The cationic lipid may also be an amino lipid. Suitable amino lipids include those having alternative fatty acid groups and other dialkylamino groups, including those in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid. Representative amino lipids include, but are not limited to, 1,2-dilinoleyoxy-3-(dimethylamino) acetoxypropane (DLin-DAC), 1,2-dilinoleyoxy-3morpholinopropane (DLin-MA), 1,2-dilinoleoyl-3-dimethylaminopropane (DLinDAP), 1,2-dilinoleylthio-3-dimethylaminopropane (DLin-S-D A), 1-linoleoyl-2-linoleyloxy-3dimethylaminopropane (DLin-2-DMAP), 1,2-dilinoleyloxy-3-trimethylaminopropane chloride salt (DLin-TMA.CI), 1,2-dilinoleoyl-3-trimethylaminopropane chloride salt (DLin-TAP.CI), 1,2-dilinoleyloxy-3-(N-methylpiperazino) propane (DLin-MPZ), 3-(N,Ndilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA), 2,2-dilinoleyl-4-(2-dimethylaminoethyl)-[1,3]-dioxolane (DLin-KC2-DMA); dilinoleyl-methyl-4-dimethylaminobutyrate (DLin-MC3-DMA); C3 (US20100324120).

In some embodiments, amino or cationic lipids have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention. In some embodiments, the protonatable lipids have a pKa of the protonatable group in the range of about 4 to about 11, e.g., a pKa of about 5 to about 7. LNPs can include two or more cationic lipids. The cationic lipids can be selected to contribute different advantageous properties. For example, cationic lipids that differ in properties such as amine pKa, chemical stability, half-life in circulation, half-life in tissue, net accumulation in tissue, or toxicity can be used in the LNP. In particular, the cationic lipids can be chosen so that the properties of the mixed-LNP are more desirable than the properties of a single-LNP of individual lipids.

In some embodiments, the cationic lipid is present in a ratio of from about 20 mol % to about 70 or 75 mol % or from about 45 to about 65 mol % or about 20, 25, 30, 35, 40, 45, 50, 55, 60, 65, or about 70 mol % of the total lipid present in the LNP. In further embodiments, the LNPs comprise from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle). In some embodiments, the ratio of cationic lipid to nucleic acid is from about 3 to about 15, such as from about 5 to about 13 or from about 7 to about 11. The amount of the permanently cationic lipid or lipidoid may be selected taking the amount of the nucleic acid cargo into account. In one embodiment, these amounts are selected such as to result in an N/P ratio of the nanoparticle(s) or of the composition in the range from about 0.1 to about 20. In this context, the N/P ratio is defined as the mole ratio of the nitrogen atoms ("N") of the basic nitrogen-containing groups of the lipid or lipidoid to the phosphate groups ("P") of the RNA which is used as cargo. The N/P ratio may be calculated on the basis that, for example, 1pg RNA typically contains about 3 nmol phosphate residues, provided that the RNA exhibits a statistical distribution of bases. The "N"-value of the lipid or lipidoid may be calculated on the basis of its molecular weight and the relative content of permanently cationic and—if present—cationisable groups.

In certain embodiments, the LNP comprises one or more additional lipids which stabilize the formation of particles during their formation.

In some embodiments, non-cationic may be used. The non-cationic lipid can be a neutral lipid, an anionic lipid, or an amphipathic lipid. Neutral lipids, when present, can be any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., LNP size and stability of the LNP in the bloodstream. Preferably, the neutral lipid is a lipid having two acyl groups (e.g., diacylphosphatidylcholine and diacylphosphatidylethanolamine). In some embodiments, the neutral lipids contain saturated fatty acids with carbon chain lengths in the range of CIO to C20. In other embodiments, neutral lipids with mono or diunsaturated fatty acids with carbon chain lengths in the range of CIO to C20 are used. Additionally, neutral lipids having mixtures of saturated and unsaturated fatty acid chains can be used. Suitable neutral lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), dimyristoyl phosphatidylcholine (DMPC), distearoyl-phosphatidyl-ethanolamine (DSPE), SM, 16-0-monomethyl PE, 16-O-dimethyl PE, 18-1—trans PE, 1-stearoyl-2-oleoyl-phosphatidyethanolamine (SOPE), cholesterol, or a mixture thereof. Anionic lipids suitable for use in LNPs include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids. In one embodiment, the neutral lipid is 1,2-distearoyl-sn-glycero-3phosphocholine (DSPC).

In some embodiments, the LNPs comprise a neutral lipid selected from DSPC, DPPC, DMPC, DOPC, POPC, DOPE and SM. In various embodiments, the molar ratio of the cationic lipid to the neutral lipid ranges from about 2:1 to about 8:1. Amphipathic lipids refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, paimitoyloleoyl phosphatdylcholine, ^phosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and beta-acyloxyacids, can also be used.

In some embodiments, the non-cationic lipid is present in a ratio of from about 5 mol % to about 90 mol %, about 5 mol % to about 10 mol %, about 5, 10, 15, 20, 25, 30, 35, 40, 45, 50, 55, 60, 65, 70, 75, 80, 85, or about 90 mol % of the total lipid present in the LNP. In some embodiments, LNPs comprise from about 0% to about 15 or 45% on a molar basis of neutral lipid, e.g., from about 3 to about 12% or from about 5 to about 10%. For instance, LNPs may include about 15%, about 10%, about 7.5%, or about 7.1% of neutral lipid on a molar basis (based upon 100% total moles of lipid in the LNP).

In some embodiments, a sterol may be used. The sterol is preferably cholesterol. The sterol can be present in a ratio of about 10 mol % to about 60 mol % or about 25 mol % to about 40 mol % of the LNP. In some embodiments, the sterol is present in a ratio of about 10, 15, 20, 25, 30, 35, 40, 45, 50, 55, or about 60 mol % of the total lipid present in the LNP. In other embodiments, LNPs comprise from about 5% to about 50% on a molar basis of the sterol, e.g., about 15% to about 45%, about 20% to about 40%, about 48%, about 40%, about 38.5%, about 35%, about 34.4%, about 31.5% or about 31% on a molar basis (based upon 100% total moles of lipid in the LNP).

In some embodiments, an aggregation reducing agent may be employed. The aggregation reducing agent can be a lipid capable of reducing aggregation. Examples of such lipids include, but are not limited to, polyethylene glycol (PEG)-modified lipids, monosialoganglioside Gml, and polyamide oligomers (PAO) such as those described in U.S. Pat. No. 6,320,017, which is incorporated by reference in its entirety. Other compounds with uncharged, hydrophilic, steric-barrier moieties, which prevent aggregation during formulation, like PEG, Gml or ATTA, can also be coupled to lipids. ATTA-lipids are described, e.g., in U.S. Pat. No. 6,320,017, and PEG-lipid conjugates are described, e.g., in U.S. Pat. Nos. 5,820,873, 5,534,499, 5,885,613, US20150376115A1 and WO2015/199952, each of which is incorporated by reference in its entirety.

The aggregation reducing agent may be, for example, selected from a polyethyleneglycol (PEG)-lipid including, without limitation, a PEG-diacylglycerol (DAG), a PEG-dialkylglycerol, a PEG-dialkyloxypropyl (DAA), a PEG-phospholipid, a PEG-ceramide (Cer), or a mixture thereof (such as PEG-Cer14 or PEG-Cer20). The PEG-DAA conjugate may be, for example, a PEG-dilauryloxypropyl (C12), a PEG-dimyristyloxypropyl (C14), a PEG-dipalmityloxypropyl (C16), or a PEG-distearyloxypropyl (C18). Other pegylated-lipids include, but are not limited to, polyethylene glycol-didimyristoyl glycerol (C14-PEG or PEG-C14, where PEG has an average molecular weight of 2000 Da) (PEG-DMG); (R)-2,3-bis(octadecyloxy) propyl-1-(methoxy polyethylene glycol) 2000) propylcarbamate) (PEG-DSG); PEG-carbamoyl-1,2-dimyristyloxypropylamine, in which PEG has an average molecular weight of 2000 Da (PEG-cDMA); N-Acetylgalactosamine-((R)-2,3-bis(octadecyloxy) propyl-1-(methoxy polyethylene glycol) 2000) propylcarbamate)) (GalNAc-PEG-DSG); mPEG (mw2000)-diastearoylphosphatidyl-ethanolamine (PEG-DSPE); and polyethylene glycol dipalmitoylglycerol (PEG-DPG). In some embodiments, the aggregation reducing agent is PEG-DMG. In other embodiments, the aggregation reducing agent is PEG-c-DMA.

In various embodiments, the molar ratio of the cationic lipid to the PEGylated lipid ranges from about 100:1 to about 25:1. In a preferred embodiment, the composition of LNPs may be influenced by, inter alia, the selection of the cationic lipid component, the degree of cationic lipid saturation, the nature of the PEGylation, the ratio of all components and biophysical parameters such as its size. In one example by Semple et al. (Semple et al. Nature Biotech. 201028:172-176; herein incorporated by reference in its entirety), the LNP composition was composed of 57.1% cationic lipid, 7.1% dipalmitoylphosphatidylcholine, 34.3% cholesterol, and 1.4% PEG-c-DMA (Basha et al. Mol Ther. 2011 19:2186-2200; herein incorporated by reference in its entirety).

In some embodiments, LNPs may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA may range from about 5:1 to about 20:1, from about 10:1 to about 25:1, from about 15:1 to about 30:1 and/or at least 30:1. The average molecular weight of the PEG moiety in the PEG-modified lipids can range from about 500 to about 8,000 Daltons (e.g., from about 1,000 to about 4,000 Daltons). In one preferred embodiment, the average molecular weight of the PEG moiety is about 2,000 Daltons.

The concentration of the aggregation reducing agent may range from about 0.1 to about 15 mol %, per 100% total moles of lipid in the LNP. In some embodiments, LNPs include less than about 3, 2, or 1 mole percent of PEG or PEG-modified lipid, based on the total moles of lipid in the LNP. In further embodiments, LNPs comprise from about 0.1% to about 20% of the PEG-modified lipid on a molar basis, e.g., about 0.5 to about 10%, about 0.5 to about 5%, about 10%, about 5%, about 3.5%, about 3%, about 2.5%, about 2%, about 1.5%, about 1%, about 0.5%, or about 0.3% on a molar basis (based on 100% total moles of lipids in the LNP). Different LNPs having varied molar ratios of cationic lipid, non-cationic (or neutral) lipid, sterol (e.g., cholesterol), and aggregation reducing agent (such as a PEG-modified lipid) on a molar basis (based upon the total moles of lipid in the lipid nanoparticles).

The total amount of nucleic acid, particularly the one or more RNAs in the lipid nanoparticles varies and may be defined depending on the e.g. RNA to total lipid w/w ratio. In one embodiment of the invention the RNA to total lipid ratio is less than 0.06 w/w, preferably between 0.03 w/w and 0.04 w/w.

In some embodiments, the inventive mRNAs encoding a stabilized Spike protein, optionally comprised by (pharmaceutical) compositions or vaccines are formulated as liposomes. Cationic lipid-based liposomes are able to complex with negatively charged nucleic acids (e.g. mRNAs) via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the nucleic acid is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9:1833-1843).

Liposomes typically consist of a lipid bilayer that can be composed of cationic, anionic, or neutral (phospho) lipids and cholesterol, which encloses an aqueous core. Both the lipid bilayer and the aqueous space can incorporate hydrophobic or hydrophilic compounds, respectively. Liposomes may have one or more lipid membranes. Liposomes can be single-layered, referred to as unilamellar, or multi-layered, referred to as multilamellar. Liposome characteristics and behavior in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are typically present as spherical vesicles and can range in size from 20 nm to a few microns. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are herein incorporated by reference in its entirety. The inventive mRNA, optionally comprised by the (pharmaceutical) composition or vaccine, may be encapsulated by the liposome and/or it may be contained in an aqueous core which may then be encapsulated by the liposome (see International Pub. Nos. WO2012/031046, WO2012/031043, WO2012/030901 and WO2012/006378 and US Patent Publication No. US20130189351, US20130195969 and US20130202684; the contents of each of which are herein incorporated by reference in their entirety).

In some embodiments, the inventive mRNA, and preferably a COVID-19 mRNA vaccine having a stabilized Spike protein, optionally comprised by the (pharmaceutical) composition or vaccine, may be formulated in liposomes such as, but not limited to, DiLa2 liposomes (Marina Biotech, Bothell, WA), SMARTICLES® (Marina Biotech, Bothell, WA), neutral DOPC (1,2-dioleoyl-sn-glycero-3-phosphocholine) based liposomes (e.g., siRNA delivery for (Landen et al. Cancer Biology & Therapy 2006 5(12)1708-1713); herein incorporated by reference in its entirety) and hyaluronan-coated liposomes (Quiet Therapeutics, Israel).

In some embodiments, the inventive mRNA, and preferably a COVID-19 mRNA vaccine having a stabilized Spike protein, optionally comprised by the (pharmaceutical) composition or vaccine, is formulated in the form of lipoplexes, i.e. cationic lipid bilayers sandwiched between nucleic acid (e.g. mRNA) layers. Cationic lipids, such as DOTAP, (1,2-dioleoyl-3-trimethylammonium-propane) and DOTMA (N-

[1-(2,3-dioleoyloxy) propyl]-N,N,N-trimethyl-ammonium methyl sulfate) can form complexes or lipoplexes with negatively charged nucleic acids to form nanoparticles by electrostatic interaction, providing high in vitro transfection efficiency.

In some embodiments, the inventive mRNA, and preferably a COVID-19 mRNA vaccine having a stabilized Spike protein, optionally comprised by the (pharmaceutical) composition or vaccine as defined herein, is formulated in the form of nanoliposomes, preferably neutral lipid-based nanoliposomes such as 1,2-dioleoyl-sn-glycero-3-phosphatidylcholine (DOPC)-based nanoliposomes (Adv Drug Deliv Rev. 2014 February; 66:110-116.). In some embodiments, the inventive mRNA, and preferably a COVID-19 mRNA vaccine having a stabilized Spike protein, optionally comprised by the (pharmaceutical) composition or vaccine as defined herein, is provided in the form of an emulsion. In some embodiment, said mRNA is formulated in a cationic oil-in-water emulsion, wherein the emulsion particle comprises an oil core and a cationic lipid which can interact with said mRNA, anchoring the molecule to the emulsion particle (see International Pub. No. WO2012/006380; herein incorporated by reference in its entirety). In some embodiments, said mRNA is formulated in a water-in-oil emulsion comprising a continuous hydrophobic phase in which the hydrophilic phase is dispersed. As a non-limiting example, the emulsion may be made by the methods described in International Publication No. WO2010/87791, the contents of which are herein incorporated by reference in its entirety.

In a preferred embodiment, the composition according to the invention comprises at least one peptide, DNA, or mRNA according to the invention, and preferably a COVID-19 mRNA vaccine having a stabilized Spike protein, that is formulated together with a cationic or polycationic compound and/or with a polymeric carrier. Accordingly, in a further embodiment of the invention, it is preferred that the mRNA as defined herein or any other nucleic acid comprised in the inventive (pharmaceutical) composition or vaccine is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of mRNA or nucleic acid to cationic or polycationic compound and/or with a polymeric carrier; or optionally in a nitrogen/phosphate (N/P) ratio of mRNA or nucleic acid to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9. More preferably, the N/P ratio of the at least one mRNA to the one or more polycations is in the range of about 0.1 to 10, including a range of about 0.3 to 4, of about 0.5 to 2, of about 0.7 to 2 and of about 0.7 to 1.5.

Therein, the COVID-19 vaccine having a stabilized Spike protein, as defined herein or any other nucleic acid comprised in the (pharmaceutical) composition or vaccine according to the invention can also be associated with a vehicle, transfection or complexation agent for increasing the transfection efficiency and/or the immunostimulatory properties of the mRNA according to the invention or of optionally comprised further included nucleic acids.

Cationic or polycationic compounds, being particularly preferred agents in this context include protamine, nucleolin, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, plsl, FGF, Lactoferrin, Transportan, Buforin-2, Bac715-24, SynB, SynB(l), pVEC, hCT-derived peptides, SAP, or histones. More preferably, the mRNA according to the invention is complexed with one or more polycations, preferably with protamine or oligofectamine, most preferably with protamine. In this context protamine is particularly preferred. Additionally, preferred cationic or polycationic proteins or peptides may be selected from the following proteins or peptides having the following total formula (III):

Particularly preferred cationic peptides in this context are identified in the disclosure of WO2009/030481 which is incorporated herewith by reference.

Preferred cationic or polycationic proteins or peptides may be derived from the patent application WO2009/030481 or WO2011/026641, the disclosure of WO2009/030481 and WO2011/026641 relating thereto are incorporated herewith by reference. Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy) propyl)]-N,N,N-trimethylammonium chloride, DMRIE, di-C14-amidine, DOTIM, SAINT, DC-Choi, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio) propane, DC-6-14:0,0-ditetradecanoyl-N-(a-trimethylammonioacetyl) diethanolamine chloride, CLIP1: rac-[(2,3-dioctadecyloxypropyl) (2-hydroxyethyl)]-dimethylammonium chloride, CLIP6: rac-[2 (2,3-dihexadecyloxypropyl-oxymethyloxy)ethyl] trimethylammonium, CLIP9: rac-[2 (2,3-dihexadecyloxypropyl-oxysuccinyloxy)ethyl]-trimethylammonium, oligofectamine, or cationic or polycationic polymers, e.g. modified polyaminoacids, such as β-amino-acid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAA based dendrimers, etc., polyimine(s), such as PEI: poly(ethyleneimine), poly(propyleneimine), etc., polyaliylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. 15 selected from a cationic polymer as mentioned above) and of one or more hydrophilic or hydrophobic blocks (e.g. polyethyleneglycole); etc.

According to a preferred embodiment, the composition of the present invention comprises the stabilized Spike protein compositions, as defined herein, and preferably a COVID-19 mRNA vaccine having a stabilized Spike protein, and a polymeric carrier. A polymeric carrier used according to the invention might be a polymeric carrier formed by disulfide-crosslinked cationic components. The disulfide-crosslinked cationic components may be the same or different from each other. The polymeric carrier can also contain further components. It is also particularly preferred that the polymeric carrier used according to the present invention comprises mixtures of cationic peptides, proteins or polymers and optionally further components as defined herein, which are crosslinked by disulfide bonds as described herein. In this context, the disclosure of WO2012/013326 is incorporated herewith by reference.

In this context, the cationic components, which form basis for the polymeric carrier by disulfide-cross linkage, are typically selected from any suitable cationic or polycationic peptide, protein or polymer suitable for this purpose, particular any cationic or polycationic peptide, protein or polymer capable of complexing the mRNA as defined herein or a further nucleic acid comprised in the composition, and thereby preferably condensing the mRNA or the nucleic acid. The cationic or polycationic peptide, protein, or polymer, is preferably a linear molecule, however, branched cationic or polycationic peptides, proteins or polymers may also be used. Every disulfide-crosslinking cationic or polycationic protein, peptide or polymer of the polymeric carrier, which may be used to complex the mRNA according to the invention or any further nucleic acid comprised in the (pharmaceutical) composition or vaccine of the present invention contains at least one —SH moiety, most preferably at least one cysteine residue or any further chemical group exhibiting an —SH moiety, capable of forming a disulfide linkage upon condensation with at least one further cationic or polycationic protein, peptide or polymer as cationic component of the polymeric carrier as mentioned herein.

As defined above, the polymeric carrier, which may be used to complex the stabilized Spike protein vaccine of the present invention, and preferably a COVID-19 mRNA vaccine having a stabilized Spike protein, or any further nucleic acid comprised in the (pharmaceutical) composition or vaccine according to the invention may be formed by disulfide-crosslinked cationic (or polycationic) components. Preferably, such cationic or polycationic peptides or proteins or polymers of the polymeric carrier, which comprise or are additionally modified to comprise at least one-SH moiety, are selected from, proteins, peptides and polymers as defined herein for complexation agent.

According to another embodiment, the (pharmaceutical) composition or vaccine according to the invention may comprise an adjuvant, which is preferably added in order to enhance the immunostimulatory properties of the composition. In this context, an adjuvant may be understood as any compound, which is suitable to support administration and delivery of the composition according to the invention. Furthermore, such an adjuvant may, without being bound thereto, initiate or increase an immune response of the innate immune system, i.e. a nonspecific immune response. In other words, when administered, the composition according to the invention typically initiates an adaptive immune response due to an antigen as defined herein or a fragment or variant thereof, which is encoded by the at least one coding sequence of the inventive mRNA contained in the composition of the present invention. Additionally, the composition according to the invention may generate an (supportive) innate immune response due to addition of an adjuvant as defined herein to the composition according to the invention.

Such an adjuvant may be selected from any adjuvant known to a skilled person and suitable for the present case, i.e. supporting the induction of an immune response in a mammal. Preferably, the adjuvant may be selected from the group consisting of, without being limited thereto, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-Al-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(bl-4)-N-acetylmuramyl-L-alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT oral adjuvant (*E. coli* labile enterotoxin-protoxin); microspheres and microparticles of any composition; MF59™; (squalane-water emulsion); MONTANIDE ISA 51TM (purified incomplete Freund's adjuvant); MONTANIDE ISA 720TM (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (B-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, AL); STIMULON™ (QS-21); Quil-A (Quil-A saponin); S-28463 (4-amino-otec-dimethyl-2-ethoxymethyl-1H-imidazo[4,5 c] quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19, 23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1J-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, I FA, F59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, P M, Inulin; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide. Particularly preferred, an adjuvant may be selected from adjuvants, which support induction of a Th1-immune response or maturation of naive T-cells, such as GM-CSF, IL-12, IFNy, any immunostimulatory nucleic acid as defined above, preferably an immunostimulatory RNA, CpG DNA, etc. In a further preferred embodiment it is also possible that the inventive composition contains besides the antigen-providing DNA, protein, or mRNA further components which are selected from the group comprising: further antigens (e.g. in the form of a peptide or protein) or further antigen-encoding nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

Suitable adjuvants may also be selected from cationic or polycationic compounds wherein the adjuvant is preferably prepared upon complexing the compositions according to the invention with the cationic or polycationic compound. Associating or complexing the mRNA of the composition with cationic or polycationic compounds as defined herein preferably provides adjuvant properties and confers a stabilizing effect to the mRNA of the composition. In particular, such preferred cationic or polycationic compounds are selected from cationic or polycationic peptides or proteins, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pisl, FGF, Lactoferrin, Transportan, Buforin-2, Bac715-24, SynB, SynB(1), pVEC, hCT-derived peptides, SAP, protamine, spermine, spermidine, or histones. Further preferred cationic or polycationic compounds may include cationic polysaccharides, for example chitosan, polybrene, cationic polymers, e.g. polyethyleneimine (PEI), cationic lipids, e.g. DOTMA: [1-(2,3-sioleyloxy) propyl)]-N,N,N-trimethylammonium chloride, DMRIE, di-C14-amidine, DOTIM, SAINT, DC-Choi, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio) propane, DC-6-14:0,0-ditetradecanoyl-N-(a-trimethylammonioacetyl) diethanolamine chloride, CLIP1: rac-[(2,3-dioctadecyloxypropyl) (2-hydroxyethyl)]-dimethylammonium chloride, CLIP6: rac-[2 (2,3-dihexadecyloxypropyl-oxymethyloxy)ethyl]-trimethylammonium, CLIP9: rac-[2 (2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., blockpolymers consisting of a combination of one or more cationic blocks (e.g. selected of a cationic polymer as mentioned above) and of one or more hydrophilic- or hydrophobic blocks (e.g polyethyleneglycole); etc.

Additionally, preferred cationic or polycationic proteins or peptides, which can be used as an adjuvant by complexing the DNA, protein, or preferably mRNA of the composition according to the invention, The ratio of the mRNA to the cationic or polycationic compound in the adjuvant component may be calculated on the basis of the nitrogen/phosphate ratio (N/P-ratio) of the entire mRNA complex, i.e. the ratio of positively charged (nitrogen) atoms of the cationic or polycationic compound to the negatively charged phosphate atoms of the nucleic acids. For example, lpg of RNA typically contains about 3 nmol phosphate residues, provided the RNA exhibits a statistical distribution of bases. Additionally, lpg of peptide typically contains about x nmol nitrogen residues, dependent on the molecular weight and the number of basic amino acids. When exemplarily calculated for (Arg)9 (molecular weight 1424 g/mol, 9 nitrogen atoms), lpg (Arg)9 contains about 700 pmol (Arg)9 and thus 700×9-6300 pmol basic amino acids=6.3 nmol nitrogen atoms. For a mass ratio of about 1:1 RNA/(Arg)9 an N/P ratio of about 2 can be calculated. When exemplarily calculated for protamine (molecular weight about 4250 g/mol, 21 nitrogen atoms, when protamine from salmon is used) with a mass ratio of about 2:1 with 2 pg RNA, 6 nmol phosphate are to be calculated for the RNA; lpg protamine contains about 235 pmol protamine molecules and thus 235×21=4935 pmol basic nitrogen atoms=4.9 nmol nitrogen atoms. For a mass ratio of about 2:1 RNA/protamine an N/P ratio of about 0.81 can be calculated. For a mass ratio of about 8:1 RNA/protamine an N/P ratio of about 0.2 can be calculated. In the context of the present invention, an N/P-ratio is preferably in the range of about 0.1-10, preferably in a range of about 0.3-4 and most preferably in a range of about 0.5-2 or 0.7-2 regarding the ratio of RNA: peptide in the complex, and most preferably in the range of about 0.7-1.5. In a preferred embodiment, the composition of the present invention is obtained in two separate steps in order to obtain both, an efficient immunostimulatory effect and efficient translation of the mRNA according to the invention. Therein, a so called "adjuvant component" is prepared by complexing—in a first step—an mRNA as defined herein of the adjuvant component with a cationic or polycationic compound in a specific ratio to form a stable complex. In this context, it is important, that no free cationic or polycationic compound or only a negligibly small amount remains in the adjuvant component after complexing the mRNA. Accordingly, the ratio of the mRNA and the cationic or polycationic compound in the adjuvant component is typically selected in a range that the mRNA is entirely complexed and no free cationic or polycationic compound or only a negligible small amount remains in the composition. Preferably the ratio of the adjuvant component, i.e. the ratio of the mRNA to the cationic or polycationic compound is selected from a range of about 6:1 (w/w) to about 0,25:1 (w/w), more preferably from about 5:1 (w/w) to about 0,5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w).

According to a preferred embodiment, the stabilized Spike protein vaccine of the invention, and preferably a COVID-19 mRNA vaccine having a stabilized Spike protein, is added in a second step to the complexed mRNA of the adjuvant component in order to form the (immunostimulatory) composition of the invention. Therein, the mRNA of the composition according to the invention is added as free mRNA, which is not complexed by other compounds. Prior to addition, the free mRNA is not complexed and will preferably not undergo any detectable or significant complexation reaction upon the addition of the adjuvant component. This is due to the strong binding of the cationic or polycationic compound to the above described mRNA according to the invention comprised in the adjuvant component. In other words, when the mRNA comprising at least one coding region as defined herein is added to the "adjuvant component", preferably no free or substantially no free cationic or polycationic compound is present, which could form a complex with the free mRNA. Accordingly, an efficient translation of the mRNA of the composition is possible in vivo. Therein, the free mRNA, may occur as a mono-, di-, or multicistronic mRNA, i.e. an mRNA which carries the coding sequences of one or more proteins. Such coding sequences in di-, or even multicistronic mRNA may be separated by at least one IRES sequence, e.g. as defined herein. In a particularly preferred embodiment, the free mRNA as defined herein, which is comprised in the composition of the present invention, may be identical or different to the RNA as defined herein, which is comprised in the adjuvant component of the composition, depending on the specific requirements of therapy. Even more preferably, the free RNA, which is comprised in the composition according to the invention, is identical to the RNA of the adjuvant component of the inventive composition.

In a particularly preferred embodiment, the composition according to the invention comprises the mRNA of the invention, and preferably a COVID-19 mRNA vaccine having a stabilized Spike protein, which encodes a plurality of antigenic peptide or proteins as defined herein and wherein said mRNAs are optionally present in the composition partially as free mRNA and partially as complexed mRNA. Preferably, the mRNA as defined herein is complexed as described above and the same mRNA is then added as free mRNA, wherein preferably the compound, which is used for complexing the mRNA is not present in free form in the composition at the moment of addition of the free mRNA component.

The ratio of the first component (i.e. the adjuvant component comprising or consisting of the mRNA as defined herein complexed with a cationic or polycationic compound) and the second component (i.e. the free mRNA as defined herein) may be selected in the inventive composition according to the specific requirements of a particular therapy. Typically, the ratio of the mRNA in the adjuvant component and the at least one free mRNA (mRNA in the adjuvant component: free mRNA) of the composition according to the invention is selected such that a significant stimulation of the innate immune system is elicited due to the adjuvant component. In parallel, the ratio is selected such that a significant amount of the free mRNA can be provided in vivo leading to an efficient translation and concentration of the expressed protein in vivo, e.g. the at least one antigenic peptide or protein as defined herein. Preferably the ratio of the mRNA in the adjuvant component: free mRNA in the inventive composition is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of mRNA in the adjuvant component: free mRNA in the inventive composition is selected from a ratio of about 1:1 (w/w).

Additionally, or alternatively, the ratio of the first component (i.e. the adjuvant component comprising or consisting of the DNA, peptide, or preferably mRNA complexed with a cationic or polycationic compound) and the second component (i.e. the free mRNA) may be calculated on the basis of the nitrogen/phosphate ratio (N/P-ratio) of the entire mRNA complex. In the context of the present invention, an N/P-ratio is preferably in the range of about 0.1-10, preferably in a range of about 0.3-4 and most preferably in a range of about 0.5-2 or 0.7-2 regarding the ratio of mRNA: peptide in the complex, and most preferably in the range of about 0.7-1.5. Additionally or alternatively, the ratio of the first component (i.e. the adjuvant component comprising or consisting of the mRNA complexed with a cationic or polycationic compound) and the second component (i.e. the free mRNA) may also be selected in the composition according to the invention on the basis of the molar ratio of both mRNAs to each other, i.e. the mRNA of the adjuvant component, being complexed with a cationic or polycationic compound and the free mRNA of the second component. Typically, the molar ratio of the mRNA of the adjuvant component to the free mRNA of the second component may be selected such, that the molar ratio suffices the above (w/w) and/or N/P-definitions. More preferably, the molar ratio of the mRNA of the adjuvant component to the free mRNA of the second component may be selected e.g. from a molar ratio of about 0.001:1, 0.01:1, 0.1:1, 0.2:1, 0.3:1, 0.4:1, 0.5:1, 0.6:1, 0.7:1, 0.8:1, 0.9:1, 1:1, 1:0.9, 1:0.8, 1:0.7, 1:0.6, 1:0.5, 1:0.4, 1:0.3, 1:0.2, 1:0.1, 1:0.01, 1:0.001, etc. or from any range formed by any two of the above values, e.g. a range selected from about 0.001:1 to 1:0.001, including a range of about 0.01:1 to 1:0.001, 0.1:1 to 1:0.001, 0.2:1 to 1:0.001, 0.3:1 to 1:0.001, 0.4:1 to 1:0.001, 0.5:1 to 1:0.001, 0.6:1 to 1:0.001, 0.7:1 to 1:0.001, 0.8:1 to 1:0.001, 0.9:1 to 1:0.001, 1:1 to 1:0.001, 1:0.9 to 1:0.001, 1:0.8 to 1:0.001, 1:0.7 to 1:0.001, 1:0.6 to 1:0.001, 1:0.5 to 1:0.001, 1:0.4 to 1:0.001, 1:0.3 to 1:0.001, 1:0.2 to 1:0.001, 1:0.1 to 1:0.001, 1:0.01 to 1:0.001, or a range of about 0.01:1 to 1:0.01, 0.1:1 to 1:0.01, 0.2:1 to 1:0.01, 0.3:1 to 1:0.01, 0.4:1 to 1:0.01, 0.5:1 to 1:0.01, 0.6:1 to 1:0.01, 0.7:1 to 1:0.01, 0.8:1 to 1:0.01, 0.9:1 to 1:0.01, 1:1 to 1:0.01, 1:0.9 to 1:0.01, 1:0.8 to 1:0.01, 1:0.7 to 1:0.01, 1:0.6 to 1:0.01, 1:0.5 to 1:0.01, 1:0.4 to 1:0.01, 1:0.3 to 1:0.01, 1:0.2 to 1:0.01, 1:0.1 to 1:0.01, 1:0.01 to 1:0.01, or including a range of about 0.001:1 to 1:0.01, 0.001:1 to 1:0.1, 0.001:1 to 1:0.2, 0.001:1 to 1:0.3, 0.001:1 to 1:0.4, 0.001:1 to 1:0.5, 0.001:1 to 1:0.6, 0.001:1 to 1:0.7, 0.001:1 to 1:0.8, 0.001:1 to 1:0.9, 0.001:1 to 1:1, 0.001 to 0.9:1, 0.001 to 0.8:1, 0.001 to 0.7:1, 0.001 to 0.6:1, 0.001 to 0.5:1, 0.001 to 0.4:1, 0.001 to 0.3:1, 0.001 to 0.2:1, 0.001 to 0.1:1, or a range of about 0.01:1 to 1:0.01, 0.01:1 to 1:0.1, 0.01:1 to 1:0.2, 0.01:1 to 1:0.3, 0.01:1 to 1:0.4, 0.01:1 to 1:0.5, 0.01:1 to 1:0.6, 0.01:1 to 1:0.7, 0.01:1 to 1:0.8, 0.01:1 to 1:0.9, 0.01:1 to 1:1, 0.001 to 0.9:1, 0.001 to 0.8:1, 0.001 to 0.7:1, 0.001 to 0.6:1, 0.001 to 0.5:1, 0.001 to 0.4:1, 0.001 to 0.3:1, 0.001 to 0.2:1, 0.001 to 0.1:1, etc.

Even more preferably, the molar ratio of the DNA, proteins, and preferably mRNA of the adjuvant component to the free mRNA of the second component may be selected e.g., from a range of about 0.01:1 to 1:0.01. Most preferably, the molar ratio of the mRNA of the adjuvant component to the free mRNA of the second component may be selected e.g. from a molar ratio of about 1:1. Any of the above definitions with regard to (w/w) and/or N/P ratio may also apply.

Suitable nucleic acid adjuvants may be incorporated herein via WO002008014979 and WO2009095226.

Accordingly, the vaccine according to the invention is based on the same components as the (pharmaceutical) composition described herein. Insofar, it may be referred to the description of the (pharmaceutical) composition as provided herein. Preferably, the vaccine according to the invention comprises at least one mRNA, and preferably a COVID-19 mRNA vaccine having a stabilized Spike protein, comprising at least one mRNA sequence as defined herein and a pharmaceutically acceptable carrier. In embodiments, where the vaccine comprises more than one mRNA sequence (such as a plurality of RNA sequences according to the invention, wherein each preferably encodes a distinct antigenic peptide or protein), the vaccine may be provided in physically separate form and may be administered by separate administration steps. The vaccine according to the invention may correspond to the (pharmaceutical) composition as described herein, especially where the mRNA sequences are provided by one single composition. However, the inventive vaccine may also be provided physically separated. For instance, in embodiments, wherein the vaccine comprises more than one mRNA sequences/species, these RNA species may be provided such that, for example, two, three, four, five or six separate compositions, which may contain at least one mRNA species/sequence each (e.g. three distinct mRNA species/sequences), each encoding distinct antigenic peptides or proteins, are provided, which may or may not be combined. Also, the inventive vaccine may be a combination of at least two distinct compositions, each composition comprising at least one mRNA encoding at least one of the antigenic peptides or proteins defined herein. Alternatively, the vaccine may be provided as a combination of at least one mRNA, preferably at least two, three, four, five, six or more mRNAs, each encoding one of the antigenic peptides or proteins defined herein. The vaccine may be combined to provide one single composition prior to its use, or it may be used such that more than one administration is required to administer the distinct mRNA sequences/species encoding any of the antigenic peptides or proteins as defined herein. If the vaccine contains at least one mRNA sequence, typically at least two mRNA sequences, encoding the antigen combinations defined herein, it may e.g. be administered by one single administration (combining all mRNA species/sequences), by at least two separate administrations. Accordingly; any combination of mono-, bi- or multicistronic mRNAs encoding the at least one antigenic peptide or protein or any combination of antigens as defined herein (and optionally further antigens), provided as separate entities (containing one mRNA species) or as combined entity (containing more than one mRNA species), is understood as a vaccine according to the present invention. According to a particularly preferred embodiment of the inventive vaccine, the at least one antigen, preferably a combination as defined herein of at least two, three, four, five, six or more antigens encoded by the inventive composition as a whole, is provided as an individual (monocistronic) mRNA, which is administered separately.

As with the (pharmaceutical) composition according to the present invention, the entities of the vaccine may be provided in liquid and or in dry (e.g. lyophilized) form. They may contain further components, in particular further components allowing for its pharmaceutical use. The vaccine or the (pharmaceutical) composition may, e.g., additionally contain a pharmaceutically acceptable carrier and/or further auxiliary substances and additives and/or adjuvants. The vaccine or (pharmaceutical) composition typically comprises a safe and effective amount of the mRNA according to the invention as defined herein, encoding an antigenic peptide or protein as defined herein or a fragment or variant thereof or a combination of antigens, preferably as defined herein. As used herein, "therapeutically effective amount" means an amount of the stabilized Spike protein vaccine that is sufficient to significantly induce a positive immune response, that preferable prevent infection of COVID-19 coronavirus. At the same time, however, a "therapeutically effective amount" is small enough to avoid serious side-effects, that is to say to permit a sensible relationship between advantage and risk. The determination of these limits typically lies within the scope of sensible medical judgment. In relation to the vaccine or (pharmaceutical) composition of the present invention, the expression "therapeutically effective amount" preferably means an amount of the a COVID-19 mRNA vaccine having a stabilized Spike protein (and thus of the encoded antigen) that is suitable for stimulating the adaptive immune system in such a manner that no excessive or damaging immune reactions are achieved but, preferably, also no such immune reactions below a measurable level. Such a "therapeutically effective amount" of the mRNA of the (pharmaceutical) composition or vaccine as defined herein may furthermore be selected in dependence of the type of mRNA, e.g. monocistronic, bi- or even multicistronic mRNA, since a bi- or even multicistronic mRNA may lead to a significantly higher expression of the encoded antigen(s) than the use of an equal amount of a monocistronic mRNA. A "therapeutically effective amount" of the a COVID-19 mRNA vaccine having a stabilized Spike protein of the (pharmaceutical) composition or vaccine as defined above will furthermore vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The vaccine or composition according to the invention can be used according to the invention for human and also for veterinary medical purposes, as a pharmaceutical composition or as a vaccine.

In a preferred embodiment, the mRNA of the (pharmaceutical) composition, and preferably a COVID-19 mRNA vaccine having a stabilized Spike protein or kit of parts according to the invention is provided in lyophilized form. Preferably, the lyophilized mRNA is reconstituted in a suitable buffer, advantageously based on an aqueous carrier, prior to administration, e.g. Ringer-Lactate solution, which is preferred, Ringer solution, a phosphate buffer solution. In a preferred embodiment, the (pharmaceutical) composition, the vaccine or the kit of parts according to the invention contains at least one, two, three, four, five, six or more mRNAs, preferably mRNAs which are provided separately in lyophilized form (optionally together with at least one further additive) and which are preferably reconstituted separately in a suitable buffer (such as Ringer-Lactate solution) prior to their use so as to allow individual administration of each of the (monocistronic) mRNAs. The vaccine or (pharmaceutical) composition according to the invention may typically contain a pharmaceutically acceptable carrier. The expression "pharmaceutically acceptable carrier" as used herein preferably includes the liquid or non-liquid basis of the inventive vaccine. If the inventive vaccine is provided in liquid form, the carrier will be water, typically pyrogen-free water; isotonic saline or buffered (aqueous) solutions, e.g phosphate, citrate etc. buffered solutions. Particularly for injection of the inventive vaccine, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCI, Nal, NaBr, a2C(¼), NaHCCh, a2S0₄, examples of the optional potassium salts include e.g. KCI, KI, KBr, K2CO3, KHCO3, K2SO4, and examples of calcium salts include e.g. CaCb, Cal2, CaBr2, CaCC>3, CaSC, Ca (OH)$_2$. Furthermore, organic anions of the aforementioned cations may be contained in the buffer. According to a more preferred embodiment, the buffer suitable for injection purposes as defined above, may contain salts selected from sodium chloride (NaCI), calcium chloride (CaCb) and optionally potassium chloride (KCI), wherein further anions may be present additional to the chlorides. CaCb can also be replaced by another salt like KCI. Typically, the salts in the injection buffer are present in a concentration of at least 50 mM sodium chloride (NaCI), at least 3 mM potassium chloride (KCI) and at least 0.01 mM calcium chloride (CaCb). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well, which are suitable for administration to a person. The term "compatible" as used herein means that the constituents of the inventive vaccine are capable of being mixed with the mRNA according to the invention as defined herein, in such a manner that no interaction occurs, which would substantially reduce the pharmaceutical effectiveness of the inventive vaccine under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose, trehalose and sucrose; starches, such as, for example, corn starch or potato starch; dextrose; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The choice of a pharmaceutically acceptable carrier is determined, in principle, by the manner, in which the pharmaceutical composition or vaccine according to the invention is administered. The composition or vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, composition or vaccines according to the present invention may be administered by an intradermal, subcutaneous, or intramuscular route, preferably by injection, which may be needle-free and/or needle injection. Compositions/vaccines are therefore preferably formulated in liquid or solid form. The suitable amount of the vaccine or composition according to the invention to be administered can be determined by routine experiments, e.g. by using animal models. Such models include, without implying any limitation, rabbit, sheep, mouse, rat, dog, and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels, and the like. If the inventive composition or vaccine is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs, and storability, which are not critical for the purposes of the present invention, and can be made without difficulty by a person skilled in the art.

According to one aspect of the present invention, the mRNA, a COVID-19 mRNA vaccine having a stabilized Spike protein, the (pharmaceutical) composition or the vaccine may be used according to the invention (for the preparation of a medicament) for the treatment or prophylaxis of COVID-19 coronavirus infections or disorders related thereto. In this context, also included in the present invention are methods of treating or preventing COVID-19 coronavirus infections or disorders related thereto, preferably as defined herein, by administering to a subject in need thereof a therapeutically effective amount of the mRNA, and preferably a COVID-19 mRNA vaccine having a stabilized Spike protein, the (pharmaceutical) composition or the vaccine according to the invention. Such a method typically comprises an optional first step of preparing the mRNA, the composition or the vaccine of the present invention, and a second step, comprising administering (a therapeutically effective amount of) said composition or vaccine to a patient/subject in need thereof. A subject in need thereof will typically be a mammal. In the context of the present invention, the mammal is preferably selected from the group comprising, without being limited thereto, e.g. goat, cattle, swine, dog, cat, donkey, monkey, ape, a rodent such as a mouse, hamster, rabbit and, particularly a human.

The invention also relates to the use of the mRNA sequence, and preferably a COVID-19 mRNA vaccine having a stabilized Spike protein, the composition or the vaccine according to the invention, preferably for eliciting an immune response in a mammal, preferably for the treatment or prophylaxis of COVID-19 coronavirus infections or a related condition as defined herein. The present invention furthermore comprises the use of the mRNA sequence(s), the (pharmaceutical) composition or the vaccine according to the invention as defined herein for modulating, preferably for inducing or enhancing, an immune response in a mammal as defined herein, more preferably for preventing and/or treating COVID-19 coronavirus infections, or of diseases or disorders related thereto. In this context, the treatment or prophylaxis of COVID-19 coronavirus infections according to the invention may comprise a combination of the inventive (pharmaceutical) composition or vaccine with a conventional COVID-19 coronavirus therapy method. In some embodiments, the treatment or prophylaxis comprises administration of an antiviral drug.

Accordingly, any use of the mRNA sequence, the (pharmaceutical) composition or the vaccine according to the invention in co-therapy with any other approach, preferably one or more of the above therapeutic approaches, in particular in combination with antivirals is within the scope of the present invention. For administration, preferably any of the administration routes may be used as defined herein. In particular, an administration route is used, which is suitable for treating or preventing a COVID-19 coronavirus infection as defined herein or diseases or disorders related thereto, by inducing or enhancing an adaptive immune response on the basis of an antigen encoded by the mRNA sequence according to the invention. Administration of the composition and/or the vaccine according to the invention may then occur prior, concurrent and/or subsequent to administering another composition and/or vaccine as defined herein, which may—in addition—contain another mRNA sequence or combination of mRNA sequences encoding a different antigen or combination of antigens, wherein each antigen encoded by the mRNA sequence according to the invention is preferably suitable for the treatment or prophylaxis of COVID-19 coronavirus infections and diseases or disorders related thereto. In this context, a treatment as defined herein may also comprise the modulation of a disease associated to COVID-19 coronavirus infection and of diseases or disorders related thereto.

According to a preferred embodiment of this aspect of the invention, the (pharmaceutical) composition or the vaccine according to the invention is administered by injection. Any suitable injection technique known in the art may be employed. Preferably, the inventive composition is administered by injection, preferably by needle-less injection, for example by jet-injection. In one embodiment, the inventive composition comprises at least one, two, three, four, five, six, seven, eight, nine, ten, eleven, twelve or more mRNAs as defined herein, each of which is preferably injected separately, preferably by needle-less injection. Alternatively, the inventive composition comprises at least one, two, three, four, five, six, seven, eight, nine, ten, eleven, twelve or more mRNAs, wherein the at least one, two, three, four, five, six, seven, eight, nine, ten, eleven, twelve or more mRNAs are administered, preferably by injection as defined herein, as a mixture. The immunization protocol for the immunization of a subject against an antigen or a combination of at least two, three, four, five, six, seven, eight, nine, ten, eleven, twelve or more antigens as defined herein typically comprises a series of single doses or dosages of the (pharmaceutical) composition or the vaccine according to the invention. A single dosage, as used herein, refers to the initial/first dose, a second dose or any further doses, respectively, which are preferably administered in order to "boost" the immune reaction. In this context, each single dosage preferably comprises the administration of the same antigen or the same combination of antigens as defined herein, wherein the interval between the administration of two single dosages can vary from at least one day, preferably 2, 3, 4, 5, 6 or 7 days, to at least one week, preferably 2, 3, 4, 5, 6, 7 or 8 weeks. The intervals between single dosages may be constant or vary over the course of the immunization protocol, e.g. the intervals may be shorter in the beginning and longer towards the end of the protocol. Depending on the total number of single dosages and the interval between single dosages, the immunization protocol may extend over a period of time, which preferably lasts at least one week, more preferably several weeks (e.g. 2, 3, 4, 5, 6, 7, 8, 9, 10, 11 or 12 weeks), even more preferably several months (e.g. 3, 4, 5, 6, 7, 8, 10, 11, 12, 18 or 24 months). Each single dosage preferably encompasses the administration of an antigen, preferably of a combination of at least two, three, four, five, six, seven, eight, nine, ten, eleven, twelve or more antigens as defined herein and may therefore involve at least one, preferably 1, 2, 3, 4, 5, 6, 7, 8, 9, 10, 11 or 12 injections.

According to another aspect of the present invention, the present invention also provides a kit, in particular a kit of parts, comprising the DNA, peptide, and preferably mRNA sequences for a stabilized Spike peptide as defined herein, the (pharmaceutical) composition, and/or the vaccine according to the invention, optionally a liquid vehicle for solubilizing and optionally technical instructions with information on the administration and dosage of the mRNA sequence, and preferably a COVID-19 mRNA vaccine having a stabilized Spike protein, the composition and/or the vaccine. The technical instructions may contain information about administration and dosage of the mRNA sequence, and preferably a COVID-19 mRNA vaccine having a stabilized Spike protein, the composition, and/or the DNA or protein vaccine. Such kits, preferably kits of parts, may be applied e.g. for any of the above mentioned applications or uses, preferably for the use of the mRNA sequence and preferably a COVID-19 mRNA vaccine having a stabilized Spike protein, according to the invention (for the preparation of an inventive medicament, preferably a vaccine) for the treatment or prophylaxis of COVID-19 coronavirus infections or diseases or disorders related thereto. The kits may also be applied for the use of the mRNA sequence, and preferably a COVID-19 mRNA vaccine having a stabilized Spike protein, the composition or the vaccine as defined herein (for the preparation of an inventive vaccine) for the treatment or prophylaxis of COVID-19 coronavirus infections or diseases or disorders related thereto, wherein the mRNA sequence, and preferably a COVID-19 mRNA vaccine having a stabilized Spike protein, the composition and/or the vaccine may be capable of inducing or enhancing an immune response in a mammal as defined above. Such kits may further be applied for the use of the mRNA sequence, and preferably a COVID-19 mRNA vaccine having a stabilized Spike protein, the composition or the vaccine as defined herein (for the preparation of an inventive vaccine) for modulating, preferably for eliciting, e.g. to induce or enhance, an immune response in a mammal as defined above, and preferably for supporting treatment or prophylaxis of COVID-19 coronavirus infections or diseases or disorders related thereto. Kits of parts, as a special form of kits, may contain one or more identical or different compositions and/or one or more identical or different vaccines as described herein in different parts of the kit. Kits of parts may also contain an (e.g. one) composition, an (e.g. one) vaccine and/or the mRNA sequence according to the invention in different parts of the kit, e.g. each part of the kit containing an mRNA sequence as defined herein, preferably encoding a distinct antigen. Preferably, the kit or the kit of parts contains as a part a vehicle for solubilizing the mRNA according to the invention, the vehicle preferably being Ringer-lactate solution. Any of the above kits may be used in a treatment or prophylaxis as defined above. In another embodiment of this aspect, the kit according to the present invention may additionally contain at least one adjuvant. In a further embodiment, the kit according to the present invention may additionally contain at least one further pharmaceutically active component, preferably a therapeutic compound suitable for treatment and/or prophylaxis of COVID-19 infection or a related disorder. Moreover, in another embodiment, the kit may additionally contain parts and/or devices necessary or suitable for the administration of the composition or the vaccine according to the invention, including needles, applicators, patches, injection-devices.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Generation of Spike Protein Gene and Plasmid Constructs

A COVID-19 spike protein ectodomain (GenBank MN908947;) residues 13-1198 (SEQ ID NO: 1) was codon optimized for expression in *S. cerevisiae* and was split into three gene blocks A, B, and C. (See Table 3) Each gene block was cloned into a pUC19 plasmid (Addgene: #500005) using standard restriction enzyme cloning with SalI-HF and KpnI-HF (IDT, NEB). Residue substitutions according to SEQ ID NO: 55 were made at the furin cleavage site (682-685) and proline substitutions were made at residues 986 and 987. The third gene block included a C-terminal trimerization domain. Each gene block also encoded BsaI type IIS restriction sites in order to seamlessly construct the full S ectodomain. BsaI overhangs were further designed into the constructs. (See Table 4) Regions of homology to pETconNK were further included to allow the insertion of the Spike protein in a yeast surface display plasmid C-terminally fused to the Aga2p protein. In order to also test display with the spike protein N-terminally fused to the Aga2p protein, a gene block containing a multiple cloning site between the Aga2p signal peptide and the Aga2p protein was ordered from IDT and cloned into pETconNK to construct NTerm_Aga2p_pETconNK. Because of the different orientations of the protein fused to the Aga2p protein, the regions of homology with pETconNK and NTerm_Aga2p_pETconNK differ and thus additional NTerm_A and NTerm_C gene blocks were designed and ordered. NTerm_A and NTerm_C containing different BsaI sites and the same Spike protein residues as the C-Terminal plasmids were cloned into pUC19 following standard restriction enzyme cloning. PCR was used to amplify the kanamycin resistance gene from pETconNK (Addgene: #81169) as well as used to amplify the A_pUC19 plasmid and NTerm_A_pUC19 plasmid without the ampicillin resistance gene. (See Table 5 for primer sequences) NEB's HiFi DNA Assembly protocol was then performed to insert the kanamycin resistance gene and construct A_pUC19 KanR and NTerm_A_pUC19_KanR.

Example 2: Preparation of Mutagenic Libraries

Mutagenic libraries were constructed using nicking saturation mutagenesis with a 20:1 ratio of plasmids to mutagenic primers in order to minimize the number of plasmids with multiple mutations. A_pUC19_KanR, B_pUC19, C_pUC19, NTerm_A_pUC19_KanR, and NTerm_C_pUC19 NSM libraries were digested with BsaIHFv2 (NEB) for 1 hour at 37 C, then run on a 1% agarose gel at 100V for 75 min and fragments encoding portions of the Spike protein were extracted and isolated using the Monarch DNA Gel Extraction Kit (NEB). A_pUC19_KanR and NTerm_A pUC19 KanR served as the destination plasmid with B_pUC19, C_pUC19, and NTerm_C_pUC19 as entry plasmids. For the C-terminal construct, 40 fmol of each Spike protein gene fragment corresponding to A, B, and C libraries were mixed together and ligated with T4 DNA Ligase at room temperature for 1 hour to construct S_Ecto_NSM_pUC19_KanR. For the N-terminal construct, 40 fmol of each fragment corresponding to NTerm_A, B, and NTerm_C libraries were mixed together and ligated with T4 DNA Ligase at room temperature for 1 hour to construct NTerm_S_Ecto_NSM_pUC19_KanR. After the ligation reaction was completed the DNA was cleaned and concentrated down to a final volume of 6 μL using Monarch PCR & DNA Cleanup Kit (NEB). The entire 6 μL was then transformed into chemically competent *E. coli* Mach1 cells producing a library of mutagenic spike protein with 3 mutations per plasmid on ratio of vector to insert with total DNA=80 fmol was employed. pETconNK plasmid was further modified to include 2 BsaI sites.

Example 3: Generation of a Yeast Surface Display System

In one preferred embodiment, the present inventors developed a yeast surface display (YSD) screening platform for SARS-CoV-2 spike. YSD is high-throughput, enables rapid turnaround, and has previously been used in screening for stabilizing mutations. Screening conditions were optimized by measuring the display and binding of wild-type spike ectodomain to hACE2-Fc and the SARS-CoV nAb CR3022, both of which only bind the 'up' conformation. As shown in FIG. 4, media composition, expression temperature, and orientation of the spike ectodomain on the yeast surface was optimized. As further shown in FIGS. 5-6, buffering the yeast induction medium at a higher pH than the traditional induction medium was important to achieve a signal-to-noise ratio high enough to sort yeast display libraries. Plasmid constructs S_Ecto_pUC19_KanR and pETconNK_BsaI were independently linearized via digest with restriction enzymes at 37° C. for 1 hour, subjected to agarose gel electrophoresis, and extracted by size using Monarch DNA Gel Extraction Kit (NEB). The linearized regions were co-transformed in a ratio of 1:3 insert to vector into chemically competent EBY100 following published protocols. EBY100 cells were recovered in nuclease free water for 5 minutes and then plated on three different yeast media agar plates: SDCAA, M37D, and M19D. Cells were incubated at 30° C. for 3 days. After initial growth, colonies from each plate were selected and grown up at 30° C. and 250 rpm overnight in the respective dextrose media: SDCAA, M37D, M19D. Cells were then induced in respective galactose media at an $OD_{600}$=1 at three different temperatures, 18° C., 22° C., and 30° C. for 20 hours resulting in 12 distinct test conditions for display for each orientation.

In order to determine the stabilizing spike mutations, three different binding partners were assessed. Specifically, recombinant human hACE2-Fc, CR3022, and 1A9 were selected having previously been shown to bind to COVID-19 Spike protein. The proteins were biotinylated in a 20:1 ratio of biotin to protein using EZ-Link NHS-Biotin from Thermo Scientific following the manufacturer's protocol. Induced EBY10x0 cells were washed with PBSF and resuspended in PBSF at an $OD_{600}$=10. The cells were then incubated with either 500M of the biotinylated hACE2-Fc, 500 nM of the biotinylated CR3022, or 250 nM biotinylated 1A9 for 1 hour at room temperature. The cells were then washed with PBSF and labeled with anti-c-myc fluorescein isothiocyanate (FITC) and streptavidin phycoerythrin (SAPE) and incubated on ice for 10 minutes. The levels of display and binding were assessed by fluorescence measurements for FITC and SAPE using the Sony SH800 cell sorter equipped with a 70 μm sorting chip and 488 nm laser.

Example 4: Methodology for Identification of Stabilizing Spike Protein Mutations In one embodiment, a Spike protein mutational library was constructed in a yeast surface display background. Upon induction, the library was sorted using fluorescence activated cell sorting using chemically biotinylated proteins: CR3022; which binds at the receptor binding domain; human ACE2, which also binds at the RBD; and the 1A9 antibody which recognizes the C-terminal stalk region of Spike. FACS gates were drawn to collect the top 2-3% of cells by fluorescence using fluorescence channels corresponding to biotinylated protein. A reference population was also collected—this reference population was the same for 1A9 and CR3022 and different for ACE2. In all, two rounds of sorting were performed. After the second sort, cells were lysed and plasmid DNA corresponding to the library was prepared for Illumina deep sequencing. Samples were sequenced on an Illumina MiSeq using 250 bp paired end reads, with raw sequencing data processed using custom scripts. For each non-synonymous mutation i: the number of times the sequence was observed in the reference and the biotinylated protein-specific ("selected") populations was selected. From this data a score was computed according to the following:

$$\text{Enrichment Ratio of } i = \log_2 \frac{\text{frequency of } i \text{ in selected population}}{\text{frequency of } i \text{ in reference population}} \quad (1)$$

$$\text{Score} = \text{Enrichment Ratio of } i - \text{Enrichment Ratio of } WT \quad (2)$$

Where WT is the wildtype or unmutated Spike sequence used in the experiment.

The measurement error in the score was calculated by two methods, with both providing substantially consistent results. As appreciated by those with knowledge of the art, the major source of error in such deep sequencing experiments are errors caused by inaccuracies in determining frequencies from the small number of times a given mutation is sequenced. These errors can be quantified as a standard deviation using Poisson statistics or by determining confidence intervals from a Fisher's exact test.

Example 5: Determination of Hits from Yeast Display Screen

For most yeast surface display measurements, the signal above background ranges from twenty to several hundred-fold. In such cases deep sequencing coupled to FACS can yield very fine and reproducible discrimination between variants in a library. However, in the present work the signal for wild-type is approximately 10% above background. Consider further that on average a mutation is destabilizing relative to WT and that the mutational library is constructed such that there are up to 3 expected mutations per gene. Together, these facts imply that the overwhelming majority of library members will have a signal at background levels. A corollary to this expectation is that the correlation between replicate experiments should be close to zero. Now consider the null hypothesis that all mutations are at background levels—that is, there are no true hits in the library. We would then expect no correlation between replicate experiments. However, some variants will show improvements in their frequency relative to the mean and some variants will show diminishment of their frequency. Estimating the probability distribution of the resultant enrichment ratios in this null scenario could be done using theoretical considerations, we have a natural experiment because we collected reference populations without selections for each of the ACE2-Fc and CR3022 experiments. These reference populations were passed passaged, sorted, and amplified identically to the sorted libraries except that no screen was employed. Thus, comparing reference populations enable us to estimate the ER distributions one would expect from the null hypothesis. Doing so for the two reference populations yields the following ER histogram well-fit by a logistic equation (x-axis is ER). (See FIG. 11-12).

Note that the ER histogram has a slightly narrower distribution as the average depth of coverage is increased for a given mutation. For example, the following distribution is seen for the ER values with an average depth of coverage of 500 or more:

FIGS. 11 and 12, imply that ER values with tighter confidence intervals—because of higher depth of coverage—should be weighted with a greater confidence. We use this original empirical distribution to map the probability distributions. Specifically, we ask the p-value for a given ER using the distribution using the full dataset. To determine the p-value when only one of the two datasets contains experimental values, we used "−20" in the code to show a p-value of 1. Identification of hits were determined as follows: since there were 1,756 mutations evaluated in the library the p-value for a FDR=1 is 5.7e-04 and FDR=20 is 1.1-02. Because the experiments were independent and thus uncorrelated, we determine an overall p-value of the null hypothesis as follows:

$$\text{p-value} = (\text{p-value})_{CR3022\ screen} \times (\text{p-value})_{hACE2\text{-}Fc\ screen}$$

Applying this naively yields 23 hits at an FDR=1 and 123 hits at an FDR=20. However, based on the above and other empirical findings (14), we can assign a higher confidence to ER with a higher depth of coverage. Conversely, we assign a lower confidence to ER with a lower depth of coverage. To become more stringent, we again filter the results using an artificial p-value determined from the 99.9% lower bound confidence interval on the ER. This analysis yields the 25 hits over 20 positions presented as Table 9 below.

Example 6: Analysis of Stabilizing Spike Protein Mutations

Figure 3A:
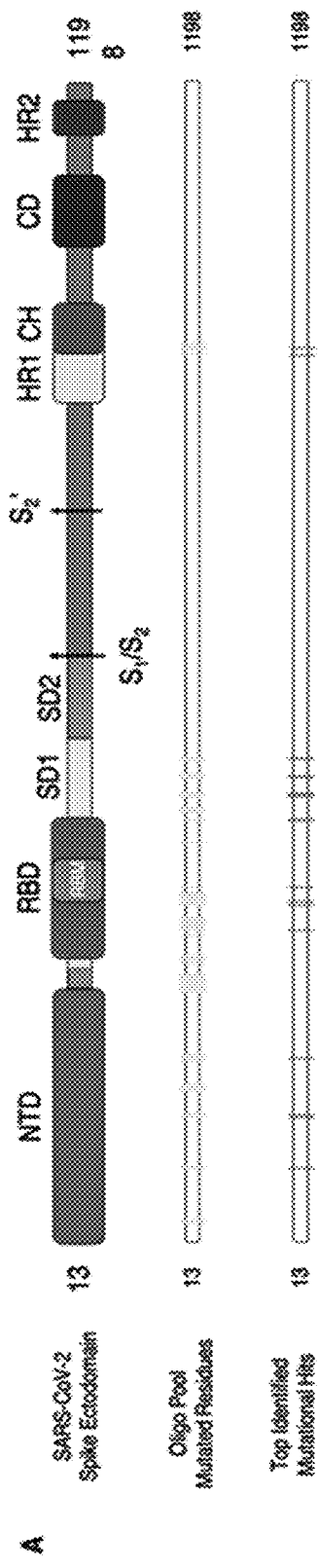
Figure 4:
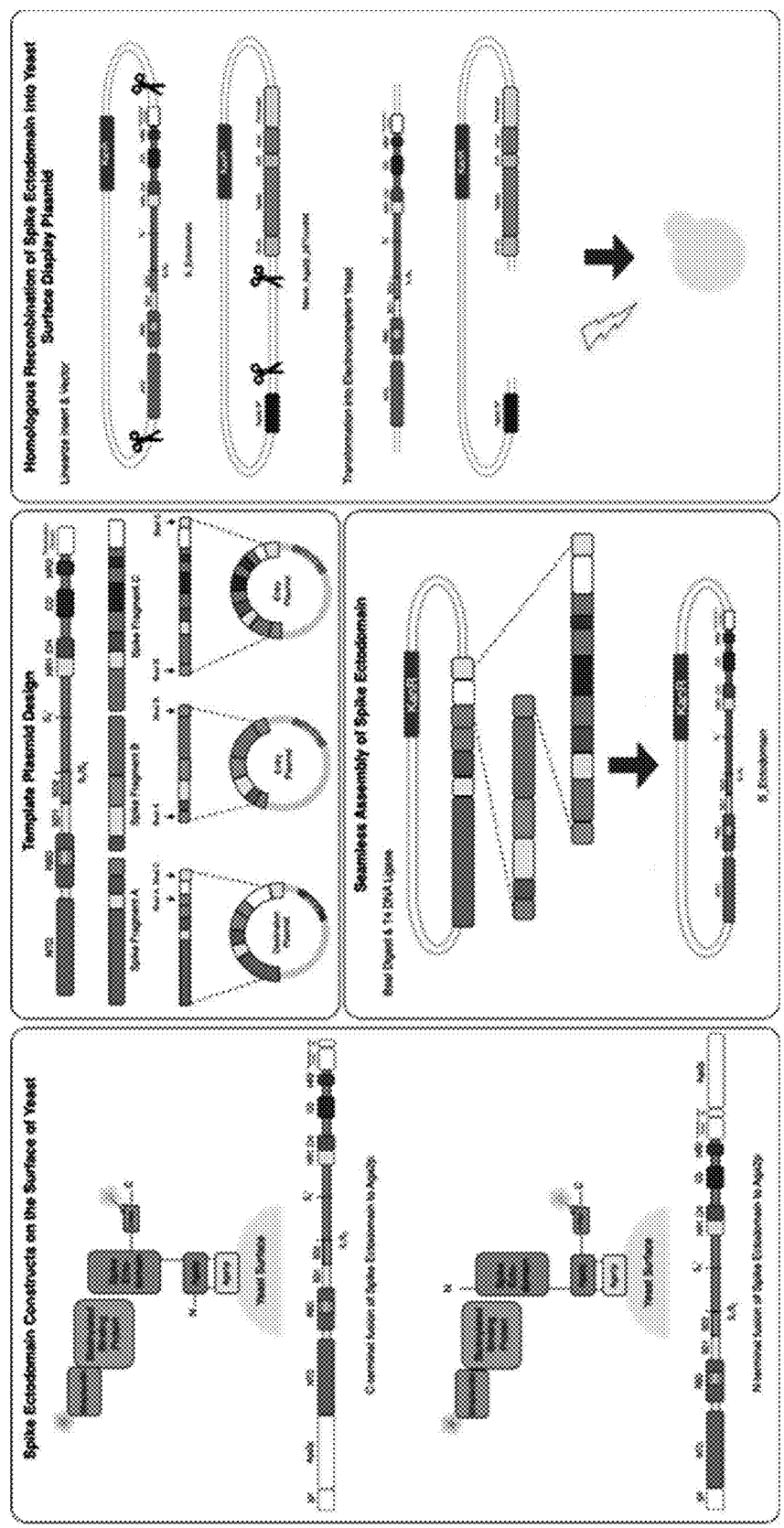
Figure 5:
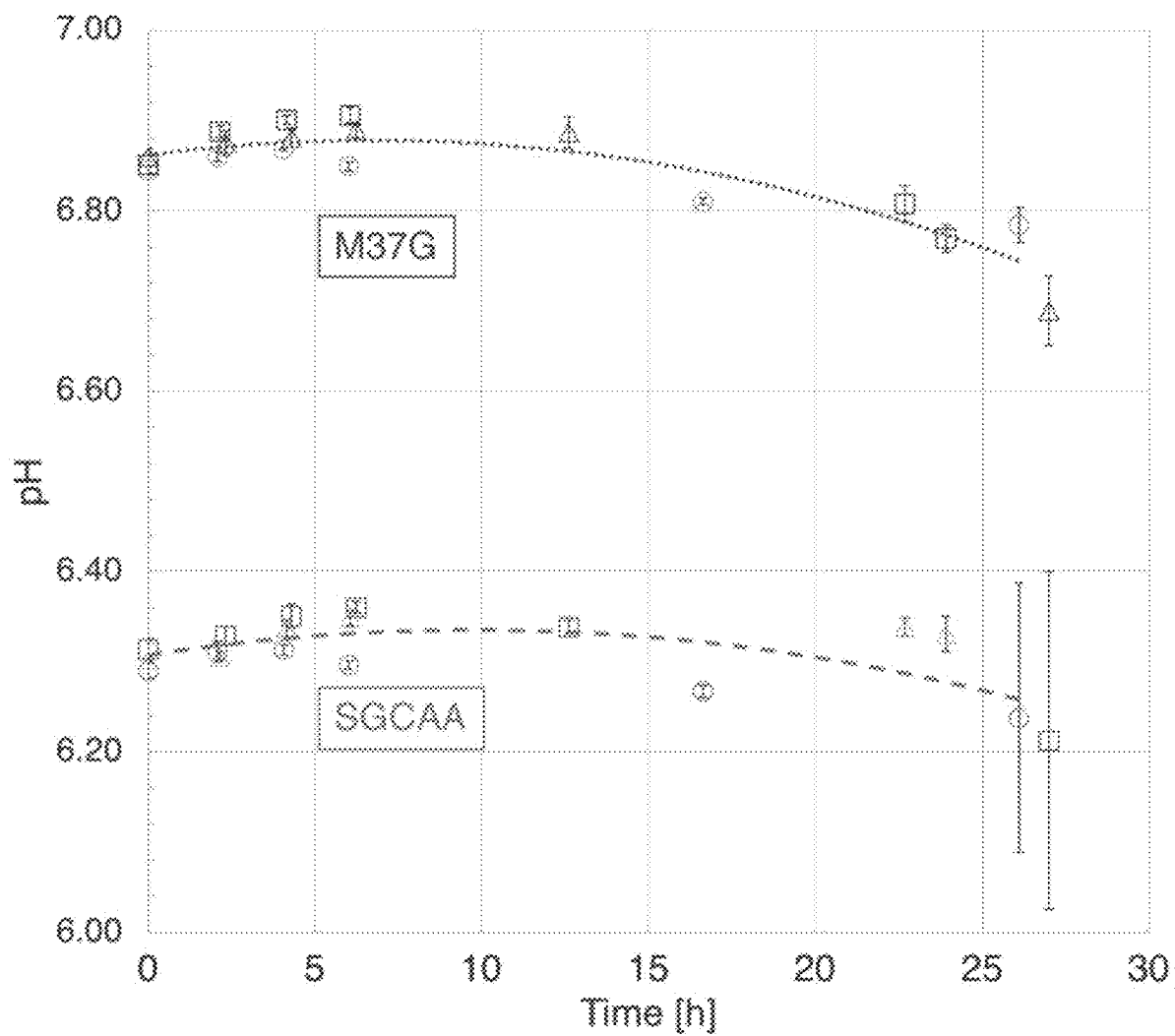
Figure 6:
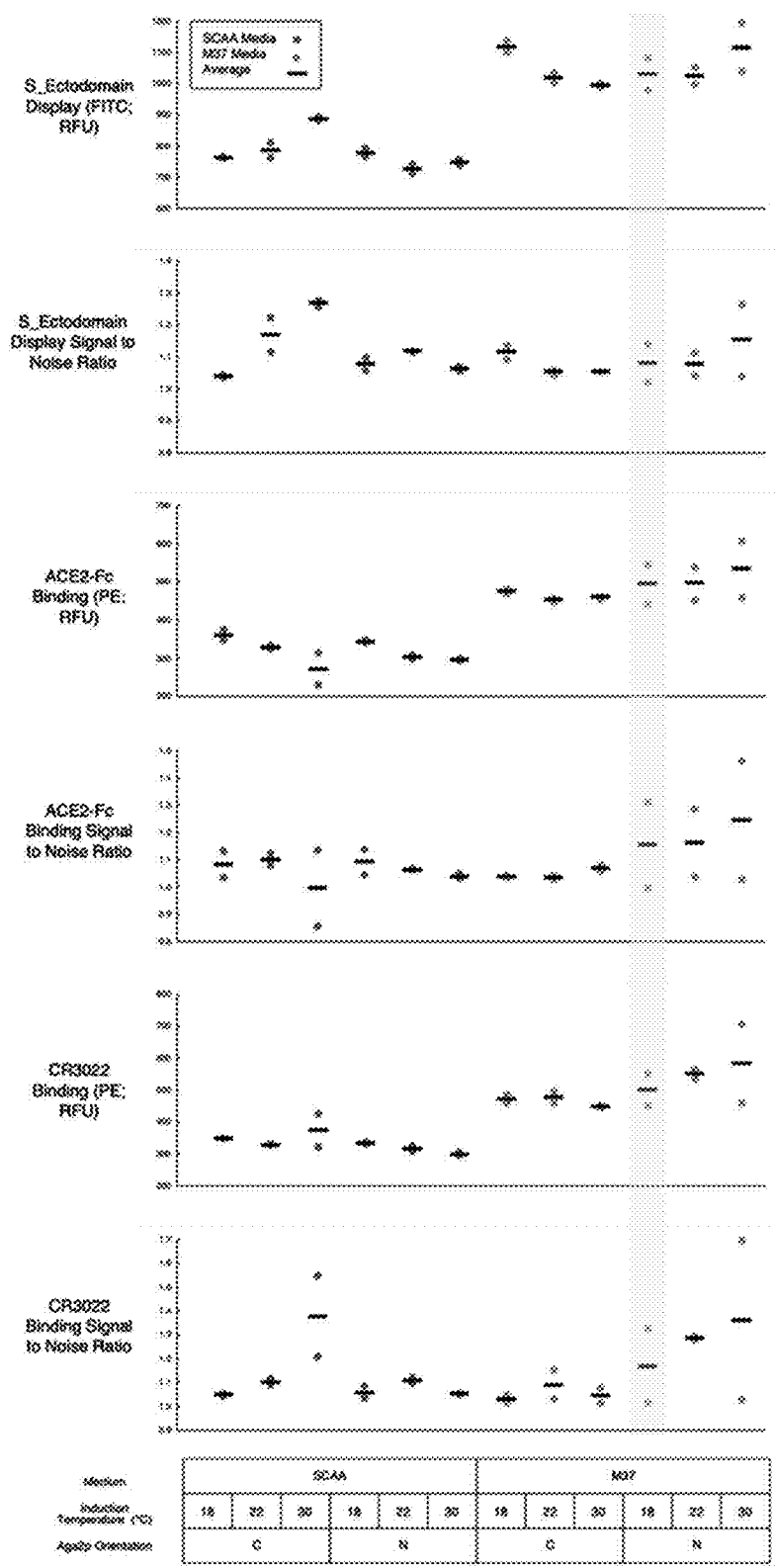
Figure 7:
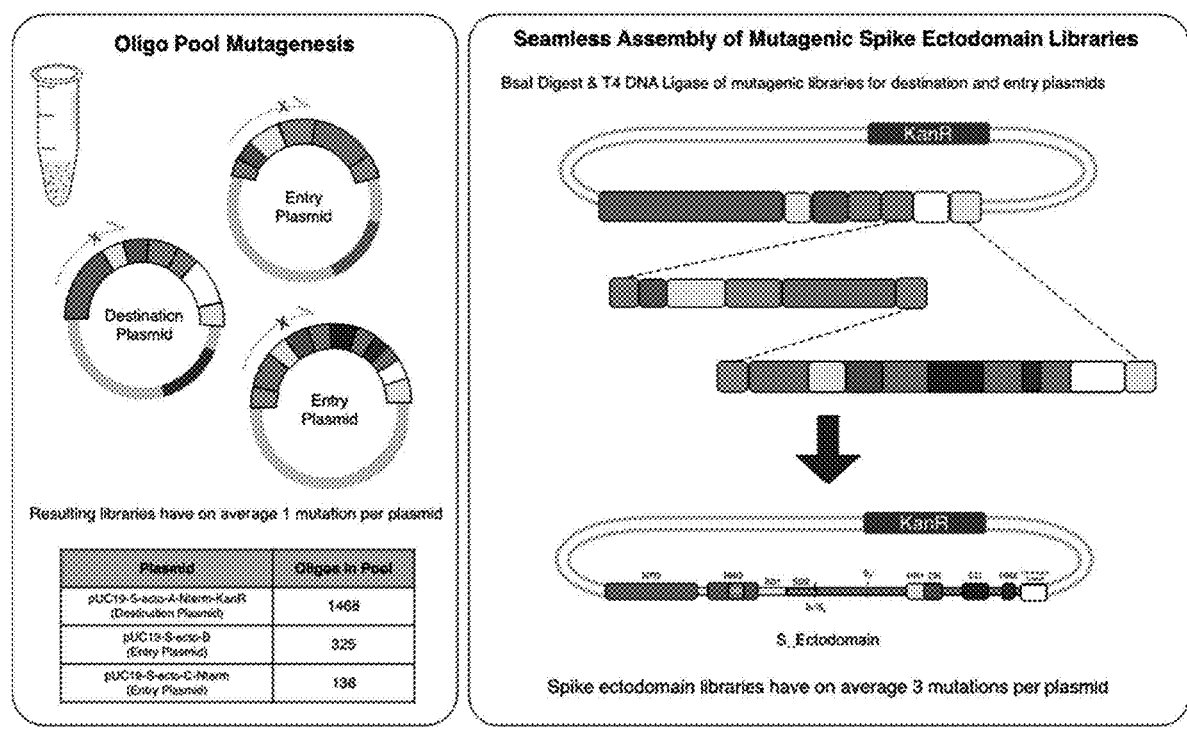
Figure 8:
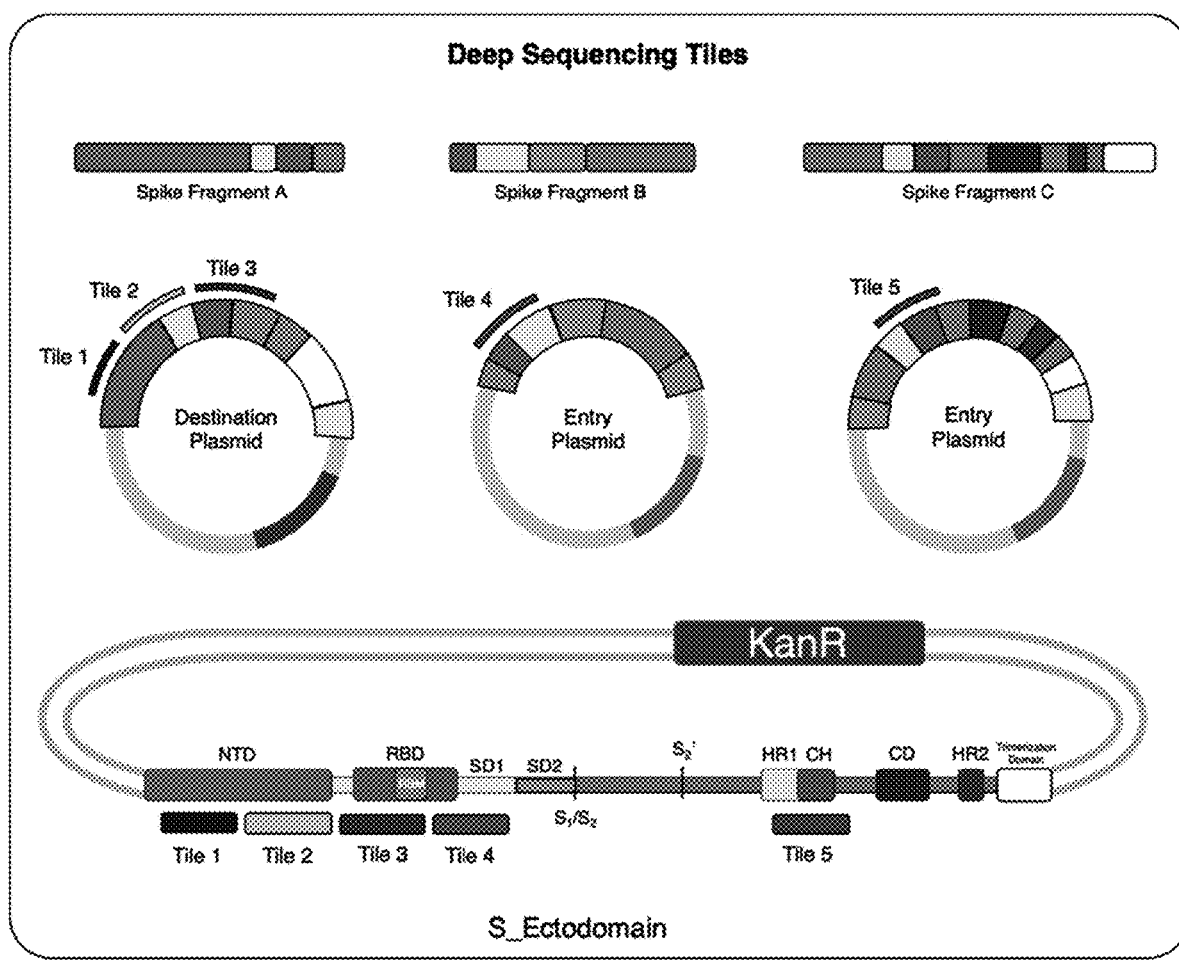

As shown in FIG. 3A, the present inventors computationally selected 1,909 mutations hypothesized to either destabilize the 'down' conformation, stabilize the 'up' conformation, or both. The majority of these mutations targeted $S_1$ (94%, 1793/1909) at the NTD, RBD, SD1, and SD2 domains, with the remainder mapping to the boundary between the HR1 and CH domains on $S_2$ (See FIG. 3A). As generally shown in FIG. 7, the present inventors incorporated mutations into the S ectodomain using oligo pool mutagenesis and constructed a spike ectodomain library in which each variant was expected to contain three mutations. As shown in FIG. 8, library members were labeled with fluorescently tagged hACE2-Fc or CR3022, $10^8$ cells were sorted using fluorescence activated cell sorting (FACS), and the top 1% of cells by fluorescence were collected. The two resulting sorted libraries were expanded and sorted in a second round, again screening $10^8$ cells, and collecting the top 1% by fluorescence intensity. As further shown in FIG. 7, the selected populations were amplified and purified based on tile, deep sequenced, and count data compared with a reference population. As demonstrated in Table 6 below, 92% of the designed mutations (1,759/1,909) were observed in the library. Mutations were evaluated by enrichment ratio (ER, the base-two logarithm of the ratio of a variant's frequency in a sorted library to its frequency in the original library) and p-value compared with an ER distribution empirically determined from the reference libraries. This analysis resulted in 5 hits at an FDR of 1 and many more at an FDR of 20. As shown in FIG. 3B-C, hits were further filtered based on lower bound ER confidence intervals as outline in Table 9 below. As further shown in FIG. 3E, most of the top 25 identified hits are located around the RBD and SD1 locations on the spike homotrimer. Although each spike ectodomain had on average 3 mutations per plasmid, the sequencing methods used evaluated mutations on an individual basis and not in the context of other mutations on the spike protein.

Hits may be enriched from the yeast display screen if they increase the overall amount of Spike displayed and/or if they alter the distribution of 'up' to 'down' protomer. Thus, mutations may globally improve the stability of prefusion spike, selectively destabilize the down state, or preferentially stabilize the up state. For example, as shown in FIG. 3F, mutations predicted to globally improve stability include N544I/L which removes a buried unsatisfied hydrogen bond in SD1. Mutation P579T may also stabilize Spike by complementing the N544 unsatisfied h-bond. F168D interacts with a basic patch on the RBD in both 'up' and 'down' protomers. However, most of the mutations likely function by selectively destabilizing the 'down' state. For example, as shown in FIG. 3G, the single largest hit in both CR3022 and hACE2-Fc screens is RBD surface mutation A372N, which directly abuts an adjacent RBD and disrupts electrostatic interactions with a helix dipole on R403 and K417 only when both protomers are in the 'down' position. Larger structural deformations were also selected for, including C166A on the NTD predicted that removes a disulfide bond predicted to structure a beta strand adjacent to the RBD in the down conformation and I973N which is predicted to add an N-linked glycan that sterically blocks RBD in the down conformation.

Example 7: Summary of Stabilizing Spike Protein Mutations

In all, 4605 mutants were observed in the deep sequencing data: 1932 single mutants were designed and screened, and additional 2,673 mutants corresponding to multiple mutations per gene and mutations not specifically designed in the initial library. The binding profiles against the different proteins give complementary data: both CR3022 and hACE2 are unable to bind when Spike is in the prefusion 'down' conformation given steric hindrance. Both CR3022 and hACE2 bind different conformational epitopes on the RBD. By contrast 1A9 binds an epitope in the stalk near the base of the spike trimer. The epitope is highly conserved among coronaviruses. 1A9 was discovered in mice immunized with a linear peptide of SARS Spike, and so the supposition is that the epitope is linear and does not depend on the quaternary structure of Spike. Mutations that improve the binding signal in the yeast display screens ('hits') were identified in the following manner: 1) For at least two binding proteins: a score >0.3 and a score/standard deviation >3.0; 2) For at least two binding proteins: a log 2 odds ratio of 99% confidence interval with a lower bound score >1.0; and 3) K41P, K41S, K41N, V126F, F168Q, P230F were included due to strong score and low error for hACE2-Fc and low abundance of these mutations in the reference populations for CR3022 and 1A9. In all, 119 exemplary mutations (See Table 1) at 63 positions (See Table 1A) met one or more of the filtering metrics above. These mutations are listed in Table 1 below. The numbered positions of these residue sites are listed are listed in Table 1A below.

Example 8: Materials and Methods

Plasmid constructs: All plasmids used for this work are listed in Table 7 and all primers in Table 8. All plasmids were sequence verified by Genewiz. Yeast display constructs for SARS-CoV-2 spike protein ectodomain (GenBank MN908947 with a substitution according to SEQ ID NO: 55 at the furin cleavage site (682-685) and proline substitutions at positions 986 and 987, and a C-terminal T4 fibritin trimerization domain), as shown in FIG. 4, were constructed as follows. Spike was codon optimized for *Saccharomyces cerevisiae* with Benchling software using default options, split into three gene blocks (hereafter labeled A, B, and C) each encoded with BsaI restriction sites with overhangs, synthesized as gBlocks (IDT), and cloned into pUC19 (Addgene: #50005) using SalI/KpnI restriction sites. This yielded the spike fragment entry plasmids pUC19-S-ecto-B, pUC19-S-ecto-C, and pUC19-S-ecto-C-Nterm. To construct pUC19-S-ecto-A-KanR and pUC19-S-ecto-A-Nterm-KanR (the spike fragment destination plasmids), PCR was used to amplify both the kanamycin resistance gene from pETconNK (Addgene: #81169) and the pUC19-S-ecto-A and pUC19-S-ecto-A-Nterm plasmids. NEBuilder HiFi DNA Assembly protocol (NEB) was used to insert the kanamycin resistance gene into the plasmids. pUC19-S-ecto and pUC19-S-ecto-Nterm were constructed by Golden Gate cloning using pUC19-S-ecto-A-KanR, pUC19-S-ecto-B, and pUC19-S-ecto-C for pUC19-S-ecto and pUC19-S-ecto-A-Nterm-KanR, pUC19-S-ecto-B, and pUC19-S-ecto-C-Nterm for pUC19-S-ecto-Nterm. To construct pJS697 (C-terminal fusion YSD backbone), pETCON-NK (Addgene: #81169) was amplified with primers PJS-P2192 and PJS-P2193 using KAPA HiFi HotStart Readymix (Kapa Biosystems). The reaction was fractionated by agarose gel electrophoresis and the 6084 bp band excised and purified using a Monarch DNA Gel Extraction kit (NEB). The fragment (40 ng) was circularized using the Q5® Site-Directed Mutagenesis Kit (NEB) in a 10 μl reaction and transformed into *E. coli* Mach1 chemically competent cells (Invitrogen). To construct pJS698 (N-terminal fusion YSD backbone), pETconNK-Nterm-Aga2p was first constructed by inserted a gene block with a multiple cloning site between the AGA2 signal peptide and the remained of the AGA2 coding sequence following standard restriction enzyme cloning practices. pETconNK-Nterm-Aga2p was amplified with primers PJS-P2194 and PJS-P2195 using KAPA HiFi HotStart Readymix (Kapa Biosystems). The reaction was fractionated by agarose gel electrophoresis and the 6062 bp band excised and purified using a Monarch DNA Gel Extraction kit (NEB). The fragment (40 ng) was circularized using the Q5® Site-Directed Mutagenesis Kit (NEB) in a 10 μl reaction and transformed into *E. coli* Mach1 chemically competent cells (Invitrogen). To construct pJS701 (human-optimized S with stabilizing mutations, a BbvCI site for nicking mutagenesis, and EcoRI/XhoI sites for subcloning into pCAGGS), pUC57-2019-nCoV-S(Human) (GenScript) was amplified in four reactions with the primer pairs PJS-P2206/PJS-P2207 (2082 bp product), PJS-P2208/PJS-P2209 (415 bp product), PJS-P2210/PJS-P2211 (536 bp product), and PJS-P2212/PJS-P2213 (702 bp product). The plasmid backbone from pYTK084 was amplified with primers PJS-P2214 and PJS-P2215 (1769 bp product). All reactions were performed with KAPA HiFi HotStart Readymix (Kapa Biosystems). The five reactions were fractionated by agarose gel electrophoresis and the bands corresponding to the desired products excised and purified using a Monarch DNA gel extraction kit (NEB). The dsDNA fragment PJS-G0017 was ordered as a gBlock (IDT). The five gel-purified PCR products and the gBlock were assembled in a 10 μl reaction using 2× NEBuilder HiFi Assembly Master Mix (NEB) (0.025 pmol each fragment). The reaction was purified using a Monarch PCR & DNA Cleanup Kit and eluted in 10 μl $H_2O$. The purified assembly product (1 μL) was electroporated into *E. coli* XL1-Blue electrocompetent cells (Agilent). To construct pJS713-pJS722 (Spike designs for subcloning), multisite nicking mutagenesis was performed as previously described. To construct pJS702-pJS712 (Spike designs for mammalian expression), pCAGGS-T7opt and the corresponding plasmid from pJS713-pJS722 were digested with EcoRI-HF and XhoI (NEB). The digestions were fractionated by agarose gel electrophoresis and the bands corresponding to the Spike design (3.8 kb) and pCAGGS backbone (4.7 kb) were excised and purified using a Monarch DNA gel extraction kit (NEB). The two fragments were ligated at room temperature by T4 DNA Ligase (NEB) and either concentrated using a Monarch DNA Cleanup kit and electroporated into *E. coli* XL1-Blue electrocompetent cells (Agilent) or heat-inactivated for 10 minutes at 65° C. and transformed into *E. coli* Mach1 chemically competent cells (Invitrogen).

Recombinant protein production: The ACE2-Fc was produced and purified following Walls et al. 2020. CR3022 was expressed by transient transfection in Expi293F cells and purified by protein A affinity chromatography and SEC using a Superdex 200 10/300 GL. Specificity was verified by measuring binding to SARS-CoV-2 RBD and irrelevant antigen. The proteins were chemically biotinylated in a 20:1 molar ratio of biotin to protein using EZ-Link NHS-Biotin (Thermo Scientific).

Computational identification of up prefusion stabilizing mutations: Stabilizing mutations were identified in several ways, with the script for the most successful protocol given in github.com/WhiteheadGroup/SpikeStabilization. In all approaches, mutations selected did not change the accessible surface area of the up protomer according to the published cryo-EM Spike ectodomain structures available at the time. One approach identified favorable antiparallel beta sheet structures for $S_1$ and $S_2$ as well as install disulfide linkages at the locations where they make their closest approaches to each other in the up protomer. Another approach located residues with side chains that face into the pocket vacated by the up protomer and sampled larger/charged/altered hydrophobic packing residues. A similar approach identified mutable positions around the RBD hinge of the up protomer to introduce attractive/repulsive forces to stabilize the up or to destabilize the down conformation. The approach that identified the majority of the hits was as follows. All positions contacting RBD in the up conformation by the rest of the protein were identified. Mutations were identified at these positions that either increased the size, changed the polarity, swapped the charge (i.e. polar->charged/non-polar, "little hydrophobic" AVIL to anything excluding cysteine). In total, 1,909 mutations were identified. The corresponding mutagenic oligonucleotides were designed using published scripts and ordered as a single oligo pool printed in duplicate (Agilent).

Preparation of Mutagenic Libraries: Mutagenic libraries for both the C-terminal and N-terminal spike orientations were constructed following oligo pool mutagenesis exactly as described using pUC19-S-ecto-A-KanR, pUC19-S-ecto-A-Nterm-KanR, pUC19-S-ecto-B, pUC19-S-ecto-C, and pUC19-S-ecto-C-Nterm as templates. After mutagenesis, the mutational libraries were digested with BsaI-HFv2, fractionated by agarose gel electrophoresis, and gel excised and purified with Monarch Gel Extraction kit (NEB). 40 fmol of pUC19-S-ecto-A-NSM-Nterm-KanR, pUC19-S-ecto-B-NSM, and pUC19-S-ecto-C-NSM-Nterm and 40 fmol of pUC19-S-ecto-A-NSM-KanR, pUC19-S-ecto-B-

NSM, and pUC19-S-ecto-C-NSM were ligated together with T4 DNA Ligase (NEB), cleaned up and concentrated each to a final volume of 6 μl with Monarch PCR & DNA Cleanup kit (NEB), and transformed into chemically competent E. coli Mach1 cells (Invitrogen cat. #C862003). The resulting two libraries had on average 3 mutations per spike protein per plasmid. Library statistics were determined post sequencing (Table 6). To construct the surface display library in yeast, plasmid libraries were digested with NotI-HF (NEB) and the S coding region was gel purified. The YSD vector pJS698 was digested with BsaI-HFv2 and column purified. 1.3 μg of insert (S coding region) and 1.7 μg of vector were electroporated into 400 μl EBY100 using the method of Benatuil et al.as written, except that electroporation was performed at 2 kV rather than 2.5 kV. Immediately after electroporation, serial dilutions were plated on SDCAA Agar to calculate the complexity of the library (Table 6). After electroporation, the cells were immediately transferred to 50 ml SDCAA (20 g/L dextrose, 6.7 g/L Difco yeast nitrogen base, 5 g/L Bacto casamino acids, 5.4 g/L $Na_2HPO_4$, and 8.56 g/L $NaH_2PO_4 \cdot H_2O$) and grown at 30° C. for two days to saturation. The cultures were passaged twice in medium M37D (diluted to $OD_{600}$=0.05 in 120 ml, then to $OD_{600}$=0.4 in 50 ml) and stocks prepared at $OD_{600}$=1 as in. The final composition of M37 is 20 g L-1 dextrose or galactose (for M37D, M37G respectively), 5 g L-1 casamino acids, 6.7 g L-1 yeast nitrogen base with ammonium sulfate, 50 mM citric acid, 50 mM phosphoric acid, 80 mM MES acid, neutralized with 90% sodium hydroxide/10% potassium hydroxide to pH 7. Both media should be prepared by dissolving all reagents except yeast nitrogen base into MilliQ water, adjusting the pH to 7.0 with freshly prepared sodium hydroxide/potassium hydroxide mixture, and adjusting the volume to 9/10th of the final desired volume. Pass the solution through a 0.22 μm filter, both for sterility and to remove particulates that would nucleate struvite. Finish the media by addition of 1/10th volume of 10× filtered yeast nitrogen base.

Yeast Display Screening: S_Ecto_pUC19_KanR and pETconNK_BsaI were independently linearized via digest with restriction enzymes at 37° C. for 1 hour, and gel extracted based off size using Monarch DNA Gel Extraction Kit. The linearized regions were co-transformed in a molar ratio of 1:3 insert to vector into chemically competent EBY100 following published protocols. EBY100 cells were recovered in nuclease free water for 5 minutes and then plated on two different yeast media agar plates: SDCAA and M37D. Cells were incubated at 30° C. for 3 days. After initial growth, colonies from each plate were selected and grown up at 30° C. and 250 rpm overnight in the respective dextrose media: SDCAA, M37D. Cells were then induced in respective galactose media at an $OD_{600}$=1 at three different temperatures, 18° C., 22° C., and 30° C. for 20 hours. Induced EBY100 cells were washed with PBSF (8 g/L NaCl, 0.2 g/L KCl, 1.44 g/L $Na_2HPO_4$, 0.24 g/L $KH_2PO_4$, and 1 g/L bovine serum albumin, pH to 7.4 and filter sterilized) and resuspended in PBSF at an $OD_{600}$=10. The cells were then incubated with either 500 nM of the biotinylated ACE2-Fc or 500 nM of the biotinylated CR3022 for 1 hour at room temperature. The cells were then washed with PBSF and labeled with anti-cmyc fluorescein isothiocyanate (FITC) (Miltenyi Biotec) and streptavidin phycoerythrin (SAPE) (Invitrogen) and incubated on ice for 10 minutes. The levels of display and binding were assessed by fluorescence measurements for FITC and SAPE using the Sony SH800 cell sorter equipped with a 70 μm sorting chip and 488 nm laser. The Spike mutagenic library labeled with CR3022 and, separately, ACE2-Fc under the optimal conditions were screened. Approximately 1e8 cells were sorted in round 1 with the top 1% of cells collected using the sort gates shown in FIG. S6. For each sort round, a reference population of yeast was collected without gating. Replicate sorts for both binding proteins was performed, again collecting the reference population and the top 1% of cells.

Deep Sequencing Preparation: Libraries were prepared for deep sequencing following the "Method B" protocol from Kowalsky et al., except a Monarch PCR & DNA Cleanup kit was used following standard procedure. Primers used in library prep are given in Table 8. Correct size of amplicons was determined by agarose gel electrophoresis. The libraries were cleaned up with Agencourt Ampure XP beads (Beckman Coulter) and pooled and sequenced on an Illumina MiSeq using 2×250 bp paired-end reads at the BioFrontiers Sequencing Core (University of Colorado, Boulder).

Deep Sequencing Analysis: All deep sequencing data analysis was performed by scripts written in *Julia* and Python, available at GITHUB. Because all sequenced samples were PCR amplicons of known length, paired-end reads were merged by aligning at the known overlap. Mismatches in overlapping regions were resolved by selecting the base pair with the higher quality score and assigning it a quality score given by the absolute difference of the quality scores at the mismatch. Merged reads containing any quality score less than 15 were discarded, and the total number of retained reads counted to give $n_i$, the number of reads in sample i. For each sample, merged reads were compared to the wild-type sequence to identify mutations (including synonymous codon changes) and tabulated to give $k_{ij}$, the number of reads in sample i encoding variant j. Variants including multiple mutations or mutations not encoded in the mutagenic oligo pool were not analyzed further. The frequency of variant j in sample i was calculated as $f_{ij}=k_{ij}/n_i$. Each experiment consisted of two samples: a reference sample r and a selected sample s. For each experiment, the risk ratio of variant j was calculated as $p_j=f_{sj}/f_{rj}$ i.e. the ratio of the variant's frequency in the selected population to its frequency in the reference population. Confidence intervals [$\rho_j^l$, $\rho_j^h$] for the risk ratio were calculated using the binomMeld.test function from the exact2×2 package in R(12). Finally, enrichment ratios and associated confidence intervals were calculated as the binary logarithm of the risk ratio: $ER_j=\log_2 \rho_j$, CI=[$\log_2 \rho_j^l$, $\log_2 \rho_j^h$].

Definitions

For the sake of clarity and readability, the following scientific background information and definitions are provided. Any technical features disclosed thereby can be part of each and every embodiment of the invention. Additional definitions and explanations can be provided in the context of this disclosure.

Vaccine for a COVID-19 coronavirus infection or COVID-19 vaccine: A vaccine, or a portion of a vaccine directed against a COVID-19 coronavirus is referred to herein as a vaccine for COVID-19 coronavirus infection, a COVID-19 vaccine. In a preferred embodiment, a COVID-19 vaccine may incorporate a one or more nucleic acid or amino acid sequences encoding a stabilized Spike protein from a coronavirus, and preferably a SARS-CoV-2 coronavirus. A COVID-19 vaccine of the invention may be a single-valent vaccine directed to the Spike protein from a coronavirus, and preferably a SARS-CoV-2 coronavirus or a multi-valent COVID-19 vaccine, having multiple components and targets such as Spike protein from a coronavirus, and preferably a SARS-CoV-2 coronavirus. In this preferred embodiment, a COVID-19 vaccine may be a multi-valent vaccine incorporate a one or more nucleic acid or amino acid sequences encoding a stabilized Spike protein from a coronavirus as generally described herein. A vaccine may be DNA-based, RNA-based or protein-based. Any reference to one type, explicitly encompasses coding sequences for the other types.

A stabilized Spike protein as described herein means a Spike protein from a coronavirus, and preferably a SAR-CoV-2 coronavirus having one more mutations that stabilize the Spike protein in a configuration that binds to its cognate receptor. In one preferred embodiment, A stabilized Spike protein as described herein means a Spike protein from a SAR-CoV-2 coronavirus having one more mutations that the stabilize the "up" protomer of the trimeric Spike protein from SARS-Cov2.

Adjuvant/adjuvant component: An adjuvant or an adjuvant component in the broadest sense is typically a (e.g. pharmacological or immunological) agent or composition that may modify, e.g. enhance, the efficacy of other agents, such as a drug or vaccine. Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question.

In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immunopotentiators, antigenic delivery systems or even combinations thereof. In the context of the present invention, an adjuvant and an immunostimulatory RNA (isRNA), such as a mRNA COVID-19 vaccine as generally described herein, may be a pharmaceutical composition.

Vaccine: A vaccine is typically understood to be a prophylactic or therapeutic material providing at least one antigen or antigenic function. The antigen or antigenic function may stimulate the body's adaptive immune system to provide an adaptive immune response. An antigen-providing mRNA in the context of the invention may typically be an mRNA, having at least one open reading frame that can be translated by a cell or an organism provided with that mRNA. The product of this translation is a peptide or protein that may act as an antigen, preferably as an immunogen. The product may also be a fusion protein composed of more than one immunogen, e.g. a fusion protein that consist of two or more epitopes, peptides or proteins derived from the same or different virus-proteins, wherein the epitopes, peptides or proteins may be linked by linker sequences.

The term "expression," as used herein, or "expression of a coding sequence" (for example, a gene or a transgene) refer to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "nucleic acid" or "nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA), whether charged or discharged with a corresponding acetylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

The term "gene" or "sequence" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide. It should be noted that any reference to a SEQ ID, or sequence specifically encompasses that sequence, as well as all corresponding sequences that correspond to that first sequence. For example, for any amino acid sequence identified, the specific specifically includes all compatible nucleotide (DNA and RNA) sequences that give rise to that amino acid sequence or protein, and vice versa.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hair-pinned, circular, and padlocked conformations.

An "expression vector" or "vector" refers to a nucleic acid construct, which when introduced into a host cell, results in transcription and/or translation of an RNA or polypeptide, respectively. More specifically, the term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature, etc. There are various types of vectors including virus, plasmid, bacteriophages, cosmids, and bacteria. Again, more specifically, "expression vector" is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette." In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s). A polynucleotide sequence is operably linked to an expression control sequence(s) (e.g., a promoter and, optionally, an enhancer) when the expression control sequence controls and regulates the transcription and/or translation of that polynucleotide sequence.

The term "heterologous" refers to a nucleic acid fragment or protein that is foreign to its surroundings. In the context of a nucleic acid fragment, this is typically accomplished by introducing such fragment, derived from one source, into a different host. Heterologous nucleic acid fragments, such as coding sequences that have been inserted into a host organism, are not normally found in the genetic complement of the host organism. As used herein, the term "heterologous" also refers to a nucleic acid fragment derived from the same organism, but which is located in a different, e.g., non-native, location within the genome of this organism. Thus, the organism can have more than the usual number of copy (ies) of such fragment located in its (their) normal position within the genome and in addition, in the case of plant cells, within different genomes within a cell, for example in the nuclear genome and within a plastid or mitochondrial genome as well. A nucleic acid fragment that is heterologous with respect to an organism into which it has been inserted or transferred is sometimes referred to as a "transgene."

The term "sequence identity" or "identity," as used herein in the context of two nucleic acid or polypeptide sequences, refers to the residues in the two sequences that are the same when aligned for maximum correspondence over a specified comparison window. The terms "approximately" and "about" refer to a quantity, level, value, or amount that varies by as much as 30%, or in another embodiment by as much as 20%, and in a third embodiment by as much as 10% to a reference quantity, level, value or amount. As used herein, the singular form "a," "an," and "the" include plural references unless the context clearly dictates otherwise.

A polynucleotide sequence is operably linked to an expression control sequence(s) (e.g., a promoter and, optionally, an enhancer) when the expression control sequence controls and regulates the transcription and/or translation of that polynucleotide sequence.

"Nucleic acid construct" or "construct" refers to an isolated polynucleotide which can be introduced into a host cell, for example a plasmid. This construct may comprise any combination of deoxyribonucleotides, ribonucleotides, and/or modified nucleotides. This construct may comprise an expression cassette that can be introduced into and expressed in a host cell.

"Operably linked" refers to a functional arrangement of elements. A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. The control elements need not be contiguous with the coding sequence, so long as they function to direct the expression thereof. Thus, for example, intervening untranslated yet transcribed sequences can be present between a promoter and the coding sequence, and the promoter can still be considered "operably linked" to the coding sequence Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art and is understood as included in embodiments where it would be appropriate. Nucleotides may be referred to by their commonly accepted single-letter codes. Unless otherwise indicated, amino acid sequences are written left to right in amino to carboxyl orientation, respectively. Amino acids may be referred to herein by either their commonly known three letter symbols or by the one-letter symbols as generally understood by those skilled in the relevant art.

Regarding disclosed ranges, the endpoints of all ranges directed to the same component or property are inclusive and independently combinable (e.g., ranges of "about 25%, or, more, about 5% to about 20 wt. %," is inclusive of the endpoints and all intermediate values of the ranges of "about 5% to about 25%," etc.). Numeric ranges recited with the specification are inclusive of the numbers defining the range and include each integer within the defined range.

Notably, all peptides disclosed in specifically encompass peptides having conservative amino acid substitutions. As used herein, "conservative amino acid substitutions" means the manifestation that certain amino acids can be substituted for other amino acids in a protein structure without appreciable loss of biochemical or biological activity. Since it is the interactive capacity and nature of a protein that defines that protein's biological functional activity, certain amino acid sequence substitutions can be made in a protein sequence, and, of course, the underlying DNA coding sequence, and nevertheless obtain a protein with like properties. Thus, various changes can be made in the amino acid sequences disclosed herein, or in the corresponding DNA sequences that encode these amino acid sequences, without appreciable loss of their biological utility or activity.

Examples of amino acid groups defined in this manner include: a "charged polar group," consisting of glutamic acid (Glu), aspartic acid (Asp), asparagine (Asn), glutamine (Gln), lysine (Lys), arginine (Arg) and histidine (His); an "aromatic, or cyclic group," consisting of proline (Pro), phenylalanine (Phe), tyrosine (Tyr) and tryptophan (Trp); and an "aliphatic group" consisting of glycine (Gly), alanine (Ala), valine (Val), leucine (Leu), isoleucine (Ile), methionine (Met), serine (Ser), threonine (Thr) and cysteine (Cys).

Within each group, subgroups can also be identified, for example, the group of charged polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gin. The aromatic or cyclic group can be sub-divided into the sub-groups consisting of the "nitrogen ring sub-group," consisting of Pro, His and Trp; and the "phenyl sub-group" consisting of Phe and Tyr.

The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala. Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free —OH can be maintained; and Gin for Asn such that a free —NH2 can be maintained.

Proteins and peptides biologically functionally equivalent to the proteins and peptides disclosed herein include amino acid sequences containing conservative amino acid changes in the fundamental amino acid sequence. In such amino acid sequences, one or more amino acids in the fundamental sequence can be substituted, for example, with another amino acid(s), the charge and polarity of which is similar to that of the native amino acid, i.e., a conservative amino acid substitution, resulting in a silent change. It should be noted that there are a number of different classification systems in the art that have been developed to describe the interchangeability of amino acids for one another within peptides, polypeptides, and proteins. The following discussion is merely illustrative of some of these systems, and the present disclosure encompasses any of the "conservative" amino acid changes that would be apparent to one of ordinary skill in the art of peptide, polypeptide, and protein chemistry from any of these different systems. Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. Table 13, infra, contains information about which nucleic acid codons encode which amino acids.

All amino acids may be reference by either their single letter of three letter code:

| Amino Acids and their Abbreviations | | |
| --- | --- | --- |
| Amino Acid | 1-Letter Symbol | 3-Letter Symbol |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Pyroglutamic acid | pQ | pGlu |
| Glycine | G | Gly |
| Histidine | H | His |
| Hydroxylysine | | Hyl |
| Hydroxyproline, 4(R)-L- | O | Hyp |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Unknown | X | |

Notably, reference to a DNA sequence, explicitly includes it transcribed RNA sequence and translated amino acid sequence. Reference to an RNA sequence, explicitly includes the DNA sequence it transcribed from, as well as the translated amino acid sequence. Finally, reference to an amino acid sequence specifically includes the RNA sequence it was translated from, and the DNA sequence that gave rise to the RNA.

Artificial mRNA (sequence): An artificial mRNA (sequence) may typically be understood to be an mRNA molecule, that does not occur naturally. In other words, an artificial mRNA molecule may be understood as a non-natural mRNA molecule. Such mRNA molecule may be non-natural due to its individual sequence (which does not occur naturally) and/or due to other modifications, e.g. structural modifications of nucleotides which do not occur naturally. Typically, artificial mRNA molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide.

The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot. In a preferred embodiment, the COVID-19 mRNA vaccine of the invention comprises an Artificial mRNA sequence.

5'-cap structure: A 5'-cap is typically a modified nucleotide (cap analogue), particularly a guanine nucleotide, added to the 5'-end of an mRNA molecule. Preferably, the 5'-cap is added using a 5'-5'-triphosphate linkage (also named m7GpppN). Further examples of 5'-cap structures include glyceryl, inverted deoxy abasic residue (moiety), ',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-cap structures may be used in the context of the present invention to modify the mRNA sequence of the inventive composition. Further modified 5'-cap structures which may be used in the context of the present invention are CAP1 (additional methylation of the ribose of the adjacent nucleotide of m7GpppN), CAP2 (additional methylation of the ribose of the 2nd nucleotide downstream of the m7GpppN), cap3 (additional methylation of the ribose of the 3rd nucleotide downstream of the m7GpppN), cap4 (additional methylation of the ribose of the 4th nucleotide downstream of the m7GpppN), ARCA (anti-reverse CAP analogue), modified ARCA (e.g. phosphothioate modified ARCA), inosine, Nl-methyl-guanosine, 2'-fluoro-guanosine, 7-deaza-guanosine, 8-oxo-guanosine, 2-amino-guanosine, LNA-guanosine, and 2-azido-guanosine. In a preferred embodiment, the 5'-cap may be provided to the COVID-19 mRNA vaccine by the 5' UTR from Xenopus β globin.

In the context of the present invention, a 5'-cap structure may also be formed in chemical RNA synthesis or RNA in vitro transcription (co-transcriptional capping) using cap analogues, or a cap structure may be formed in vitro using capping enzymes (e.g., commercially available capping kits).

Cap analogue: A cap analogue refers to a non-polymerizable di-nucleotide that has cap functionality in that it facilitates translation or localization, and/or prevents degradation of the RNA molecule when incorporated at the 5'-end of the RNA molecule. Non-polymerizable means that the cap analogue will be incorporated only at the 5' terminus because it does not have a 5' triphosphate and therefore cannot be extended in the 3 direction by a template-dependent RNA polymerase.

Cap analogues include, but are not limited to, a chemical structure selected from the group consisting of m7GpppG, m7GpppA, m7GpppC; unmethylated cap analogues (e.g., GpppG); dimethylated cap analogue (e.g., m2,7GpppG), trimethylated cap analogue (e.g., m2,2,7GpppG), dimethylated symmetrical cap analogues (e.g., m7Gpppm7G), or anti reverse cap analogues (e.g., ARCA; m7,2 OmeGpppG, m7,2 'dGpppG, m7,3 'OmeGpppG, m7,3 'dGpppG and their tetraphosphate derivatives).

Poly (C) sequence; A poly-(C)-sequence is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid. Pol v-A-tail/ sequence: A poly-A-tail also called "3'-poly(A) tail or poly (A) sequence" is typically a long sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3' end of an RNA. Moreover, poly(A) sequences, or poly(A) tails may be generated in vitro by enzymatic polyadenylation of the RNA, e.g. using Poly(A) polymerases derived from E. coli or yeast.

Poly (A) sequence; A poly-A-tail also called "3'-poly(A) tail or poly(A) sequence" is typically a long sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3'end of a RNA. Moreover, poly(A) sequences, or poly(A) tails may be generated in vitro by enzymatic polyadenylation of the RNA, e.g. using. Poly(A) polymerases derived from E. coli or yeast.

Polyadenylation: Polyadenylation is typically understood to be the addition of a poly(A) sequence to a nucleic acid molecule, such as an RNA molecule, e.g. to a premature mRNA. Polyadenylation may be induced by a so called polyadenylation signal. This signal is preferably located within a stretch of nucleotides at the 3'-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called premature-mRNA). Typically, RNA maturation (from pre-mRNA to mature mRNA) comprises the step of polyadenylation.

3'-untranslated region G'-UTR): A 3'-UTR is typically the part of an mRNA which is located between the protein coding region (i.e. the open reading frame) and the poly(A) sequence of the mRNA. A 3'-UTR of the mRNA is not translated into an amino acid sequence. The 3'-UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'-capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'-UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'-UTR sequence may be an RNA sequence, such as in the mRNA sequence used for defining the 3'-UTR sequence, or a DNA sequence which corresponds to such RNA sequence. In the context of the present invention, the term "a 3'-UTR of a gene", such as "a 3'-UTR of an albumin gene", is the sequence which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence of the 3'-UTR.

5'-untranslated region (5'-UTR): A 5'-UTR is typically understood to be a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'-UTR may be post-transcriptionally modified, for example by addition of a 5'-cap. In the context of the present invention, a 5'-UTR corresponds to the sequence of a mature mRNA which is located between the 5'-cap and the start codon. Preferably, the 5'-UTR corresponds to the sequence which extends from a nucleotide located 3' to the 5'-cap, preferably from the nucleotide located immediately 3' to the 5'-cap, to a nucleotide located 5' to the start codon of the protein coding region, preferably to the nucleotide located immediately 5' to the start codon of the protein coding region. The nucleotide located immediately 3' to the 5'-cap of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence which corresponds to such RNA sequence. In the context of the present invention, the term "a 5'-UTR of a gene", such as "a 5'-UTR of a TOP gene", is the sequence which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR.

The term "full-length protein" as used herein typically refers to a protein that substantially comprises the entire amino acid sequence of the naturally occurring protein. Nevertheless, substitutions of amino acids e.g. due to mutation in the protein are also encompassed in the term full-length protein.

Fragments of proteins: "Fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. In this context a fragment of a protein may typically comprise an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with an amino acid sequence of the respective naturally occurring full-length protein. Fragments of proteins or peptides in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore, also domains of a protein, like the extracellular domain, the intracellular domain or the transmembrane domain and shortened or truncated versions of a protein may be understood to comprise a fragment of a protein.

Variants of proteins: "Variants" of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term "variants" as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger eta/, (ed.), Elsevier, Amsterdam).

In one specific embodiment, a variant of a Spike protein, and preferably a stabilized Spike protein may include stabilizing mutation variants wherein a mutated residue, for example as identified in Table 1, is replaced with an acceptable or compatible amino acid residue, wherein said acceptable or compatible amino acid residue also stabilizes the Spike protein in the prefusion 'up' configuration.

A "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide. Furthermore, variants of proteins or peptides as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

Identity of a sequence: In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

Peptide: A peptide is a polymer of amino acid monomers. Usually, the monomers are linked by peptide bonds. The term "peptide" does not limit the length of the polymer chain of amino acids. In some embodiments of the present invention a peptide may for example contain less than 50 monomer units. Longer peptides are also called polypeptides, typically having 50 to 600 monomeric units, more specifically 50 to 300 monomeric units.

Therapeutically effective amount: A Therapeutically effective amount in the context of the invention is typically understood to be an amount that is sufficient to induce an immune response.

A "pharmaceutical composition" may include a vaccine of the invention and an agent, e.g. a carrier, that may typically be used within a pharmaceutical composition or vaccine for facilitating administering of the components of the pharmaceutical composition or vaccine to an individual.

Fragment of a nucleic acid sequence: A fragment of a nucleic acid sequence consists of a continuous stretch of nucleotides corresponding to a continuous stretch of nucleotides in the full-length nucleic acid sequence which is the basis for the nucleic acid sequence of the fragment, which represents at least 20%, preferably at least 30%, more preferably at least 40%, more preferably at least 50%, even more preferably at least 60%, even more preferably at least 70%, even more preferably at least 80%, and most preferably at least 90% of the full-length nucleic acid sequence. A 'fragment of a nucleic acid sequence'e.g. a fragment of the inventive mRNA is preferably a nucleic acid sequence encoding a fragment of a protein or of a variant thereof as described herein. More preferably, the expression 'fragment of a nucleic acid sequence' refers to a nucleic acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with a respective full-length nucleic acid sequence. Such a fragment, in the sense of the present invention, is preferably a functional fragment of the full-length nucleic acid sequence.

Variant of a nucleic acid sequence, particularly an mRNA: A variant of a nucleic acid sequence refers to a variant of nucleic acid sequences which forms the basis of a nucleic acid sequence. For example, a variant nucleic acid sequence may exhibit one or more nucleotide deletions, insertions, additions and/or substitutions compared to the nucleic acid sequence from which the variant is derived. Preferably, a variant of a nucleic acid sequence is at least 40%, preferably at least 50%, more preferably at least 60%, more preferably at least 70%, even more preferably at least 80%, even more preferably at least 90%, most preferably at least 95% identical to the nucleic acid sequence the variant is derived from. Preferably, the variant is a functional variant. A "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence. A variant of a nucleic acid sequence as used herein preferably encodes a protein or a fragment thereof as defined herein. The expression 'variant of a nucleic acid sequence' in the context of a nucleic acid sequence encoding a protein or a fragment thereof, typically refers to a nucleic acid sequence, which differs by at least one nucleic acid residue from the respective naturally occurring nucleic acid sequence encoding a protein or a fragment thereof. More preferably, the expression 'variant of a nucleic acid sequence' refers to a nucleic acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with a nucleic acid sequence, from which it is derived.

Moreover, the terms "enhance", "enhanced", "increase", "increased" or "improved" generally refer to a statistically significant increase, for example in a trait, phenotype, or catalytic rate, or production amount, such as a virus protein titer. For the avoidance of doubt, these terms generally refer to about a 5% increase in a given parameter or value, about a 10% increase, about a 15% increase, about a 20% increase, about a 25% increase, about a 30% increase, about a 35% increase, about a 40% increase, about a 45% increase, about a 50% increase, about a 55% increase, about a 60% increase, about a 65% increase, about 70% increase, about a 75% increase, about an 80% increase, about an 85% increase, about a 90% increase, about a 95% increase, about a 100% increase, or more over the control value. These terms also encompass ranges consisting of any lower indicated value to any higher indicated value, for example "from about 5% to about 50%", etc.

TABLES

TABLE 1

Summary of Spike Protein Stabilizing Mutations
Spike Protein Mutation

K41N
K41P
K41S
R44K
K113F
T114D
Q115I
Q115H
L118F
N122Y
V126F
Q134K
N165D
C166A
T167S
T167F
F168Q
E169G
T302N
Q314Y
N360H
Y369R
N370S
N370Y
N370W
A372N
S375H
V382A
V407M
V407R
Q409N
Q409C
I410G
A411I
A411F
A411L
K417V
D428Y
F429D
N487T
N487E
L518S
L518E
H519L
A520G
A520R
A520M
A522T
G526I
P527F
K528F
K528W
K528I
K528L
K529Y
S530I
S530W
T531I
N542C
F543H
F543M
N544I
N544L
N544D
N544F
G545C

TABLE 1-continued

Summary of Spike Protein Stabilizing Mutations
Spike Protein Mutation

G545P
L546F
L546G
L546N
L546M
P561N
P561F
P561Y
P561M
P561V
F562R
F562E
F562D
F562C
Q563M
Q563A
Q563S
Q563L
Q563V
Q564H
F565A
F565D
F565N
T573I
P579T
P579Y
P579D
P579K
Q580F
Q580K
Q580V
Q580I
Q580E
Q580G
Q580K
T581K
T581C
T581Q
L582H
I973N
I973L
I980T
S982M
S982I
R983A
R983V
L984R
L984F
D985S
D985V
E988M

TABLE 1A

Spike Protein Stabilizing Mutations
Spike Protein Mutation Position 41
44
113
114
115
118
122
126
134
165
166
167
168
169
302
314
360

TABLE 1A-continued

Spike Protein Stabilizing Mutations
Spike Protein Mutation Position 369
370
372
375
382
407
409
410
411
417
428
429
487
518
519
520
522
526
527
528
529
530
531
542
543
544
544
545
546
561
562
563
564
565
573
579
580
581
582
973
980
982
983
984
985
988

TABLE 2

Exemplary SARS-CoV-2 Spike glycoproteins

| SEQ ID NO. | Spike Protein Mutation |
|---|---|
| SEQ ID NO. 1 | With GSAS mutation at cleavage site (SEQ ID NO. 55); PP mutation at residues 986-987 |
| SEQ ID NO. 2 | wt |
| SEQ ID NO. 3 | wt |

TABLE 3

Spike Protein (SEQ ID NO: 1) gene blocks.

| Gene Block | Residue | Region |
|---|---|---|
| A | 13-500 | S1 subunit, RBM, most of RBD |
| B | 501-814 | Portions of S1 and S2 subunits, (GSAS) furin cleavage site |
| C | 815-1198 | S2' region including HR1 and HR2, Trimerization |

TABLE 4

BsaI overhang construction

| BsaI Overhangs C-Terminal: | BsaI Overhangs N-Terminal: |
|---|---|
| ACTA (A to B) | ACTA (A to B) |
| GAGC (B to C) | GAGC (B to C) |
| AAAA (C to A backbone) | GCAA (C to A backbone) |

TABLE 5

PCT Primer Sets

Primers to Amplify KanR: (IDT)

| | |
|---|---|
| CAATAATATTGAAAAAGGAAGAGT | SEQ ID NO: 3 |
| ATGAGTAAACTTGGTCTGACAGTT | SEQ ID NO: 4 |

Primers to Amplify A_pUC19 and Nterm_A_pUC19: (IDT)

| | |
|---|---|
| AACTGTCAGACCAAGTTTACTCAT | SEQ ID NO: 5 |
| ACTCTTCCTTTTTCAATATTATTG | SEQ ID NO: 6 |

TABLE 6

Summary of Statistics for N-Term Spike ectodomain Library.
Library statistics were determined from NGS of the libraries harbored in E. coli.

| Orientation | N_Term_SEcto | | | | |
|---|---|---|---|---|---|
| Spike Fragment | A | | | B | C |
| Tile Number | Tile 1 | Tile 2 | Tile 3 | Tile 4 | Tile 5 |
| Positions | 31-177 | 189-341 | 355-494 | 510-589 | 936-1020 |
| Number of Designed Mutations | 229 | 582 | 639 | 324 | 135 |
| Transformants Obtained from Nicking Saturation Mutagenesis | | 2.00E+06 | | 1.00E+06 | 1.00E+04 |
| Transformants Obtained from Assembly of Spike Ectodomain | | | 4.00E+05 | | |
| Transformants Obtained from | | | 1.75E+06 | | |

TABLE 6-continued

Summary of Statistics for N-Term Spike ectodomain Library.
Library statistics were determined from NGS of the libraries harbored in E. coli.

| Homologous Recombination Percentage of reads with: | | | | | |
|---|---|---|---|---|---|
| No nonsynonymous mutations | 76.8% | 64.7% | 64.7% | 65.4% | 78.3% |
| One nonsynonymous mutation | 17.9% | 26.2% | 27.0% | 30.6% | 19.8% |
| Multiple nonsynonymous mutations | 5.3% | 9.1% | 8.3% | 4.0% | 1.9% |
| Oligo Pool Library Coverage Per Tile | 88% (201/229) | 90% (523/582) | 90% (577/639) | 100% (324/324) | 99% (134/135) |
| Oligo Pool Total Library Coverage | 92% (1759/1909) | | | | |

TABLE 7

List of plasmids used in the present invention.

| Name | Description | E. coli Marker | Yeast marker | Source |
|---|---|---|---|---|
| pUC19-S-ecto-B | S ectodomain fragment positions 501-814 with BsaI sites for assembly and BbvCI site | Amp | | This study |
| pUC19-S-ecto-C | S ectodomain fragment positions 815-1198 with a C-terminal T4 fibritin trimerization domain with BsaI sites for assembly and BbvCI site | Amp | | This study |
| pUC19-S-ecto-C-Nterm | S ectodomain fragment positions 815-1198 with a C-terminal T4 fibritin trimerization domain with BsaI sites for assembly and BbvCI site | Amp | | This study |
| pUC19-S-ecto-A-KanR | S ectodomain fragment positions 13-500 with BsaI sites for assembly and BbvCI site | Kan | | This study |
| pUC19-S-ecto-A-Nterm-KanR | S ectodomain fragment positions 13-500 with BsaI sites for assembly and BbvCI site | Kan | | This study |
| pUC19-S-ecto | S ectodomain for C-terminal YSD | Kan | | This study |
| pUC19-S-ecto-Nterm | S ectodomain for N-terminal YSD | Kan | | This study |
| pJS697 | YSD vector backbone (C-terminal fusion) for in vivo HR | Kan | TRP1 | This study |
| pJS698 | YSD vector backbone (N-terminal fusion) for in vivo HR | Kan | TRP1 | This study |
| pUC57-2019-nCoV-S(Human) | Human optimized S | | | GenScript Cat. #: MC_0101081 |
| pYTK084 | KanR-ColE1 vector | Kan | | AddGene #65191 (16) |
| pJS701 | Human optimized S with stabilizing mutations and BbvCI site | Kan | | This study |
| pJS713 | S(Human)-K41S-F168Q-K528F-N544I | Kan | | This study |
| pJS714 | S(Human)-Q115H-T167F-Q314Y-P579T | Kan | | This study |
| pJS715 | S(Human)-K41S-Q115H-V126F-Q314Y-F543M | Kan | | This study |
| pJS716 | S(Human)-T167F-Q314Y-V407M-F565A | Kan | | This study |
| pJS717 | S(Human)-K41P-P230F-Q580E-L984R | Kan | | This study |
| pJS718 | S(Human)-Q115H-V126F-A411I-A522T | Kan | | This study |
| pJS719 | S(Human)-K41P-C166A-Q314Y-A522T | Kan | | This study |
| pJS720 | S(Human)-F168Q-A411I-I973N | Kan | | This study |
| pJS721 | S(Human)-K41S-V126F-P579T | Kan | | This study |
| pJS722 | S(Human)-K41N-F168Q-F543M-I973N | Kan | | This study |
| pCAGGS-mCherry | Mammalian expression vector | Amp | | AddGene #41583 (17) |
| pJS702 | pCAGGS-S(Human) | Amp | | This study |
| pJS703 | pCAGGS-S(Human)-K41S-F168Q-K528F-N544I | Amp | | This study |
| pJS704 | pCAGGS-S(Human)-Q115H-T167F-Q314Y-P579T | Amp | | This study |
| pJS705 | pCAGGS-S(Human)-K41S-Q115H-V126F-Q314Y-F543M | Amp | | This study |
| pJS706 | pCAGGS-S(Human)-T167F-Q314Y-V407M-F565A | Amp | | This study |
| pJS707 | pCAGGS-S(Human)-K41P-P230F-Q580F-L984R | Amp | | This study |
| pJS708 | pCAGGS-S(Human)-Q115H-V126F-A411I-A522T | Amp | | This study |
| pJS709 | pCAGGS-S(Human)-K41P-C166A-Q314Y-A522T | Amp | | This study |
| pJS710 | pCAGGS-S(Human)-F168Q-A411I-I973N | Amp | | This study |
| pJS711 | pCAGGS-S(Human)-K41S-V126F-P579T | Amp | | This study |
| pJS712 | pCAGGS-S(Human)-K41N-F168Q-F543M-I973N | Amp | | This study |

TABLE 8

List of primers used in the present invention.

| Number | Description | Sequence |
|---|---|---|
| MBK-175 | KanR-fwd | CAATAATATTGAAA AAGGAAGAGT (SEQ ID NO: 5) |
| MBK-176 | KanR-rev | ATGAGTAAACTTGG TCTGACAGTT (SEQ ID NO: 6) |
| MBK-177 | A-pUC19-fwd | AACTGTCAGACCAA GTTTACTCAT (SEQ ID NO: 7) |
| MBK-178 | A-pUC19-rev | ACTCTTCCTTTTTC AATATTATTG (SEQ ID NO: 8) |
| MBK-180 | DS-tile1-fwd | GTTCAGAGTTCTAC AGTCCGACGATCAC ACGTGGTGTTTATT ACCCT (SEQ ID NO: 9) |
| MBK-181 | DS-tile1-rev | CCTTGGCACCCGAG AATTCCACATAAGA AAAGGCTGAGAGAC ATA (SEQ ID NO: 10) |
| MBK-301 | DS-tile2-fwd | GTTCAGAGTTCTAC AGTCCGACGATCCT TAGGGAATTTGTGT TTAAG (SEQ ID NO: 11) |
| MBK-302 | DS-tile2-rev | CCTTGGCACCCGAGA ATTCCAAACTTCACC AAAAGGGCACAA (SEQ ID NO: 12) |
| MBK-303 | DS-tile3-fwd | GTTCAGAGTTCTACA GTCCGACGATCAGGA AGAGAATCAGCAACT GT (SEQ ID NO: 13) |
| MBK-304 | DS-tile3-rev | CCTTGGCACCCGAGA ATTCCAATGATTGTA AAGGAAAGTAACA (SEQ ID NO: 14) |
| MBK-305 | DS-tile4-fwd | GTTCAGAGTTCTACA GTCCGACGATCAGTA GTAGTACTTTCTTTT GAACTT (SEQ ID NO: 15) |
| MBK-306 | DS-tile4-rev | CCTTGGCACCCGAGA ATTCCAGGTGTAATG TCAAGAATCTCAAG (SEQ ID NO: 16) |
| MBK-307 | DS-tile5-fwd | GTTCAGAGTTCTACA GTCCGACGATCGACT CACTTTCTTCCACAG CA (SEQ ID NO: 17) |
| MBK-308 | DS-tile5-rev | CCTTGGCACCCGAGA ATTCCAAGCTCTGAT TTCTGCAGCTCT (SEQ ID NO: 18) |
| PJS-P2192 | pETCON-NK-BsaI-C-term-fwd | TGTTATGGAGCGGGT CTCAGGGGCGGATCC GAA (SEQ ID NO: 19) |
| PJS-P2193 | pETCON-NK-BsaI-C-term-rev | ACGTTCAGTGATGG TCTCTACTAGCCTG CAGAGC (SEQ ID NO: 20) |
| PJS-P2194 | pETCON-KK-BsaI-N-term-fwd | TGTTATGGAGCGGG TCTCACAGGAACTG ACAACTATATGC (SEQ ID NO: 21) |
| PJS-P2195 | pETCON-NK-BsaI-N-term-rev | ACGTTCAGTGATGG TCTCTGAAAATATT GAAAAACAGCGAAG TAA (SEQ ID NO: 22) |
| PJS-P2206 | S-1-fwd | ACCGTCCTCAGCGA ATTCGCCACCATGT TCGTCT (SEQ ID NO: 23) |
| PJS-P2207 | S-1-rev | GCTAGAGGCTGACC CGGGAGAGTTTGTC TGGGT (SEQ ID NO: 24) |
| PJS-P2208 | S-2-fwd | CTCCCGGGTCAGCC TCTAGCGTGGCCTC CCAGT (SEQ ID NO: 25) |
| PJS-P2209 | S-2-rev | ATAAAGCTGCTCTT AGAAGGCTTGGATG GAT (SEQ ID NO: 26) |
| PJS-P2210 | S-3-fwd | GCCTTCTAAGAGCA GCTTTATCGAGGAC CTG (SEQ ID NO: 27) |
| PJS-P2211 | S-3-rev | CTGCCTCTGGAGGG TCCAGCCGGCTCA (SEQ ID NO: 28) |
| PJS-P2212 | S-4-fwd | GCTGGACCCTCCAG AGGCAGAGGTGCA (SEQ ID NO: 29) |
| PJS-P2213 | S-4-rev | AAGCGGCCGCTGGG CCACTTGATGTACT (SEQ ID NO: 30) |
| PJS-P2214 | vec-fwd | GTGTTACAACCAAT TAACCAATTC (SEQ ID NO: 31) |
| PJS-P2215 | vec-rev | GCGAATTCGCTGAG GACGGTTATCCACA GAATCA (SEQ ID NO: 32) |
| PJS-P2221 | S-K41N-AAC | CTTCACCAGAGGCG TGTACTATCCTGAC AACGTGTTTAGAAG CTCCGTGCTGCACT CTA (SEQ ID NO: 33) |

TABLE 8-continued

List of primers used in the present invention.

| Number | Description | Sequence |
|---|---|---|
| PJS-P2222 | S-K41P-CCC | CTTCACCAGAGGCGTGTACTATCCTGACCCCGTGTTTAGAAGCTCCGTGCTGCACTCTA (SEQ ID NO: 34) |
| PJS-P2223 | S-K41S-AGC | CTTCACCAGAGGCGTGTACTATCCTGACAGCGTGTTTAGAAGCTCCGTGCTGCACTCTA (SEQ ID NO: 35) |
| PJS-P2224 | S-Q115H-CAC | CTTTGGCACCACACTGGACTCCAAGACACACTCTCTGCTGATCGTGAACAATGCCACCA (SEQ ID NO: 36) |
| PJS-P2225 | S-Q115H-CAC-V126F-TTC | CTTTGGCACCACACTGGACTCCAAGACACACTCTCTGCTGATCGTGAACAATGCCACCAACTTCGTCATCAAGGTGTGCGAGTTCCAGTTTT (SEQ ID NO: 37) |
| PJS-P2226 | S-V126F-TTC | TCTGCTGATCGTGAACAATGCCACCAACTTCGTCATCAAGGTGTGCGAGTTCCAGTTTT (SEQ ID NO: 38) |
| PJS-P2227 | S-C166A-GCC | GTTTAGAGTGTATTCTAGCGCCAACAACGCCACATTTGAGTACGTGAGCCAGCCTTTCC (SEQ ID NO: 39) |
| PJS-P2228 | S-T167F-TTC | TAGAGTGTATTCTAGCGCCAACAACTGCTTCTTTGAGTACGTGAGCCAGCCTTTCCTGA (SEQ ID NO: 40) |
| PJS-P2229 | S-F168Q-CAG | AGTGTATTCTAGCGCCAACAACTGCACACAGGAGTACGTGAGCCAGCCTTTCCTGATGG (SEQ ID NO: 41) |
| PJS-P2230 | S-P230F-TTC | CAGCGCCCTGGAGCCCTGGTGGATCTGTTCATCGGCATCAACATCACCCGGTTTCAGA (SEQ ID NO: 42) |
| PJS-P2231 | S-Q314Y-TAC | GTCCTTTACCGTGGAGAAGGGCATCTATTACACATCCAATTTCAGGGTGCAGCCAACCG (SEQ ID NO: 43) |
| PJS-P2232 | S-V407M-ATG | CGATTCTTTCGTGATCAGGGGCGACGAGATGCGCCAGATCGCCCCCGGCCAGACAGGCA (SEQ ID NO: 44) |
| PJS-P2233 | S-A411I-ATC | GATCAGGGGCGACGAGGTGCGCCAGATCATCCCCGGCCAGACAGGCAAGATCGCAGACT (SEQ ID NO: 45) |
| PJS-P2234 | S-A522T-ACC | GCTGAGCTTTGAGCTGCTGCACGCCCCAACCACAGTGTGCGGCCCCAAGAAGTCCACCA (SEQ ID NO: 46) |
| PJS-P2235 | S-K528F-TTC | GCACGCCCCAGCAACAGTGTGCGGCCCCTTCAAGTCCACCAATCTGGTGAAGAAC (SEQ ID NO: 47) |
| PJS-P2236 | S-F543M-ATG | GGTGAAGAACAAGTGCGTGAACTTCAACATGAACGGCCTGACCGGCACAGGCGTGCTGA (SEQ ID NO: 48) |
| PJS-P2237 | S-N544I-ATC | AAGTGCGTGAACTTCAACTTCATCGGCCTGACCGGCACAGGCGTGCTGACCG (SEQ ID NO: 49) |
| PJS-P2238 | S-F565A-GCC | CAACAAGAAGTTCCTGCCATTTCAGCAGGCCGGCAGGGACATCGCAGATACCACAGACG (SEQ ID NO: 50) |
| PJS-P2239 | S-P579T-ACC | CGCAGATACCACAGACGCCGTGCGCGACACCCAGACCCTGGAGATCCTGGACATCACAC (SEQ ID NO: 51) |
| PJS-P2240 | S-Q580F-TTC | AGATACCACAGACGCCGTGCGCGACCCATTCACCCTGGAGATCCTGGACATCACACCCT (SEQ ID NO: 52) |
| PJS-P2241 | S-I973N-AAC | GAAGCAGCTGAGCAGCAACTTCGGCGCCAACTCTAGCGTGCTGAATGACATCCTGAGCC (SEQ ID NO: 53) |
| PJS-P2242 | S-L984R-AGA | TAGCGTGCTGAATGACATCCTGAGCCGGAGAGACCCTCCAGAGGCAGAGGTGCAGATCG (SEQ ID NO: 54) |

TABLE 9

Calculated ER Value Analysis.

| MUTATION | Position | ACE_ER | ACE_ER_999 | ACE_ER_9999 | CR_ER | CR_ER_999 | CR_ER_9999 | pval_ACE_999 | pval_CR_999 | pval_ACE_9999 | pval_CR_9999 | pval_product_999 | pval_product_9999 | pval_ACE | pval_CR | pval_product |
|---|---|---|---|---|---|---|---|---|---|---|---|---|---|---|---|---|
| K113I-ATT | 113 | 4.9 | 2.3 | 1.9 | 4.9 | 3.2 | 2.9 | 0.1 | 0.0 | 0.1 | 0.0 | 1.80E-03 | 0.00 | 3.7E-03 | 3.7E-03 | 1.37E-05 |
| C166A-GCT | 166 | 7.6 | 6.1 | 5.9 | 3.0 | 1.9 | 1.7 | 0.0 | 0.1 | 0.0 | 0.1 | 9.56E-05 | 0.00 | 1.7E-04 | 3.1E-02 | 5.34E-06 |
| F168D-GAT | 168 | 2.4 | 1.6 | 1.4 | 3.9 | 2.8 | 2.6 | 0.1 | 0.0 | 0.2 | 0.1 | 5.80E-03 | 0.01 | 6.1E-02 | 1.1E-02 | 6.96E-04 |
| F168Q-CAA | 168 | 6.7 | 6.0 | 5.9 | 0.5 | -0.6 | -0.9 | 0.0 | 0.7 | 0.0 | 0.7 | 6.87E-04 | 0.00 | 4.7E-04 | 3.6E-01 | 1.71E-04 |
| E169R-AGA | 169 | 5.3 | 4.0 | 3.8 | -0.3 | -1.2 | -1.4 | 0.0 | 0.8 | 0.0 | 0.8 | 8.04E-03 | 0.01 | 2.3E-03 | 5.8E-01 | 1.37E-03 |
| Y200V-GTT | 200 | 7.4 | 4.1 | 3.7 | 2.5 | 0.6 | 0.3 | 0.0 | 0.3 | 0.0 | 0.4 | 3.01E-05 | 0.01 | 2.1E-04 | 5.4E-02 | 1.16E-05 |
| A372N-AAT | 372 | 5.8 | 4.2 | 4.0 | 11.4 | 9.3 | 9.0 | 0.0 | 0.0 | 0.0 | 0.0 | 1.98E-07 | 0.00 | 1.3E-03 | 2.2E-06 | 2.93E-09 |
| V407P-CCA | 407 | 0.2 | -0.3 | -0.4 | 4.4 | 3.9 | 3.8 | 0.6 | 0.0 | 0.6 | 0.0 | 6.52E-03 | 0.01 | 4.4E-01 | 6.5E-03 | 2.89E-03 |
| V407E-GAA | 407 | 2.1 | 1.6 | 1.4 | 5.2 | 2.7 | 2.3 | 0.1 | 0.0 | 0.2 | 0.0 | 6.46E-03 | 0.01 | 8.3E-02 | 2.6E-03 | 2.19E-04 |
| V407M-ATG | 407 | 4.1 | 3.4 | 3.3 | 4.2 | 3.4 | 3.2 | 0.0 | 0.0 | 0.0 | 0.0 | 4.14E-04 | 0.00 | 9.2E-03 | 8.2E-03 | 7.50E-05 |
| A411I-ATT | 411 | 3.1 | 2.4 | 2.3 | 3.3 | 2.3 | 2.1 | 0.1 | 0.1 | 0.1 | 0.1 | 4.13E-03 | 0.01 | 2.8E-02 | 2.3E-02 | 6.35E-04 |
| T415M-ATG | 415 | 4.3 | 4.1 | 4.1 | -2.2 | -2.6 | -2.7 | 0.0 | 1.0 | 0.0 | 1.0 | 8.79E-03 | 0.01 | 7.3E-03 | 9.3E-01 | 6.76E-03 |
| F429E-GAA | 429 | 5.6 | 3.7 | 3.5 | 2.5 | 1.6 | 1.4 | 0.0 | 0.1 | 0.0 | 0.2 | 1.91E-03 | 0.00 | 1.7E-03 | 5.4E-02 | 9.06E-05 |
| N487M-ATG | 487 | 4.2 | 3.8 | 3.7 | 1.2 | 0.3 | 0.1 | 0.2 | 0.4 | 0.2 | 0.5 | 5.36E-03 | 0.01 | 8.2E-03 | 2.0E-01 | 1.66E-03 |
| H519W-TGG | 519 | 1.6 | 0.9 | 0.8 | 4.4 | 2.9 | 2.6 | 0.3 | 0.0 | 0.3 | 0.0 | 9.72E-03 | 0.01 | 1.4E-01 | 6.5E-03 | 9.04E-04 |
| H519L-TTG | 519 | 3.1 | 2.5 | 2.4 | 1.9 | 1.4 | 1.3 | 0.1 | 0.2 | 0.1 | 0.2 | 8.94E-03 | 0.01 | 2.8E-02 | 1.0E-01 | 2.89E-03 |
| A520G-GGT | 520 | 2.1 | 1.8 | 1.8 | 2.4 | 2.1 | 2.0 | 0.1 | 0.1 | 0.1 | 0.1 | 1.00E-02 | 0.01 | 8.3E-02 | 6.1E-02 | 5.05E-03 |
| N542C-TGT | 542 | 1.6 | 1.1 | 1.0 | 4.1 | 2.9 | 2.8 | 0.2 | 0.0 | 0.2 | 0.0 | 7.43E-03 | 0.01 | 1.4E-01 | 9.2E-03 | 1.27E-03 |
| F543M-ATG | 543 | 3.5 | 3.0 | 2.9 | 1.8 | 1.4 | 1.3 | 0.0 | 0.2 | 0.0 | 0.2 | 5.42E-03 | 0.01 | 1.8E-02 | 1.1E-01 | 2.05E-03 |
| N544L-TTG | 544 | 3.1 | 2.2 | 2.1 | 4.5 | 2.5 | 2.2 | 0.1 | 0.1 | 0.1 | 0.1 | 4.03E-03 | 0.01 | 2.8E-02 | 5.8E-03 | 1.64E-04 |
| Q564G-GGT | 564 | 0.3 | -0.3 | -0.5 | 4.8 | 4.3 | 4.2 | 0.6 | 0.0 | 0.6 | 0.0 | 4.44E-03 | 0.01 | 4.2E-01 | 4.1E-03 | 1.72E-03 |
| F565A-GCT | 565 | 4.5 | 4.2 | 4.2 | 3.4 | 3.1 | 3.1 | 0.0 | 0.0 | 0.0 | 0.0 | 2.21E-04 | 0.00 | 5.8E-03 | 2.0E-02 | 1.17E-04 |

TABLE 9-continued

Calculated ER Value Analysis.

| MUTATION | Position | ACE_ER | ACE_ER_999 | ACE_ER_9999 | CR_ER | CR_ER_999 | CR_ER_9999 | pval_ACE_999 | pval_CR_999 | pval_product_999 | pval_ACE_9999 | pval_CR_9999 | pval_product_9999 | pval_ACE | pval_CR | pval_product |
|---|---|---|---|---|---|---|---|---|---|---|---|---|---|---|---|---|
| S982M-ATG | 982 | 4.2 | 3.9 | 3.9 | 0.7 | 0.1 | 0.0 | 0.0 | 0.5 | 5.34E-03 | 0.0 | 0.5 | 0.01 | 8.2E-03 | 3.1E-01 | 2.54E-03 |
| L984R-AGA | 984 | 3.3 | 2.8 | 2.8 | 2.6 | 1.7 | 1.6 | 0.0 | 0.1 | 4.57E-03 | 0.0 | 0.1 | 0.01 | 2.3E-02 | 4.9E-02 | 1.10E-03 |

REFERENCES

1. Wang, Qihui, et al. "Structural and functional basis of SARS-CoV-2 entry by using human ACE2." *Cell* (2020).
2. Zheng, Zhiqiang, et al. "Monoclonal antibodies for the S2 subunit of spike of SARS-CoV cross-react with the newly-emerged SARS-CoV-2." *bioRxiv* (2020).
3. Klesmith, Justin R., et al. "Comprehensive sequence-flux mapping of a levoglucosan utilization pathway in *E. coli*." *ACS synthetic biology* 4.11 (2015): 1235-1243.
4. Medina-Cucurella, *Angelica* V., and Timothy A. Whitehead. "Characterizing protein-Protein interactions using deep sequencing coupled to yeast surface display." *Protein Complex Assembly*. Humana Press, New York, NY, 2018. 101-121.
5. R. Yan et al., Structural basis for the recognition of SARS-CoV-2 by full-length human ACE2. *Science* 367, 1444-1448 (2020).
6. Y. Yuan et al., Cryo-EM structures of MERS-CoV and SARS-CoV spike glycoproteins reveal the dynamic receptor binding domains. *Nature communications* 8, 15092. (2017).
7. D. Wrapp et al., Cryo-EM structure of the 2019-nCoV spike in the prefusion conformation. *Science* 367, 1260-1263 (2020).
8. A. C. Walls et al., Structure, function, and antigenicity of the SARS-CoV-2 spike glycoprotein. *Cell*, (2020).
9. B. S. Graham, M. S. Gilman, J. S. McLellan, Structure-Based vaccine antigen design. *Annual review of medicine* 70, 91-104 (2019).
10. M. C. Crank et al., A proof of concept for structure-based vaccine design targeting RSV in humans. *Science* 365, 505-509 (2019).
11. J. Pallesen et al., Immunogenicity and structures of a rationally designed prefusion MERS-CoV spike antigen. *Proceedings of the National Academy of Sciences* 114, E7348-E7357 (2017).
12. F. Amanat et al., A serological assay to detect SARS-CoV-2 seroconversion in humans. *Nature medicine*, 1-4 (2020).
13. C.-L. Hsieh et al., Structure-based Design of Prefusion-stabilized SARS-CoV-2 Spikes. *bioRxiv*, (2020).
14. D. Pinto et al., Cross-neutralization of SARS-CoV-2 by a human monoclonal SARS-CoV antibody. *Nature*, 1-10 (2020).
15. C. Wang et al., A human monoclonal antibody blocking SARS-CoV-2 infection. *Nature Communications* 11, 1-6 (2020).
16. S. J. Zost et al., Rapid isolation and profiling of a diverse panel of human monoclonal antibodies targeting the SARS-CoV-2 spike protein. *bioRxiv*, (2020).
17. P. Brouwer et al., Potent neutralizing antibodies from COVID-19 patients define multiple targets of vulnerability. *bioRxiv*, (2020).
18. Y. Wu et al., A noncompeting pair of human neutralizing antibodies block COVID-19 virus binding to its receptor ACE2. *Science*, (2020).
19. J. R. Klesmith, J.-P. Bacik, E. E. Wrenbeck, R. Michalczyk, T. A. Whitehead, Trade-offs between enzyme fitness and solubility illuminated by deep mutational scanning. *Proceedings of the National Academy of Sciences* 114, 2265-2270 (2017).
20. M. Yuan et al., A highly conserved cryptic epitope in the receptor binding domains of SARS-CoV-2 and SARS-CoV. *Science* 368, 630-633 (2020).
21. G. Chao et al., Isolating and engineering human antibodies using yeast surface display. *Nature protocols* 1, 755 (2006).
22. A. V. Medina-Cucurella et al., User-defined single pot mutagenesis using unamplified oligo pools. *Protein Engineering, Design and Selection*, (2019).
23. E. E. Wrenbeck et al., Plasmid-based one-pot saturation mutagenesis. *Nature methods* 13, 928 (2016).
24. M. S. Faber et al., Saturation mutagenesis genome engineering of infective ΦX174 bacteriophage via unamplified oligo pools and golden gate assembly. *ACS Synthetic Biology*, (2019).
25. M. P. Fay, M. A. Proschan, E. Brittain, Combining one-sample confidence procedures for inference in the two-sample case. *Biometrics* 71, 146-156 (2015).
26. V. Potapov et al., Comprehensive profiling of four base overhang ligation fidelity by T4 DNA ligase and application to DNA assembly. *ACS synthetic biology* 7, 2665-2674 (2018).
27. C. Engler, S. Marillonnet, in *DNA cloning and assembly methods*. (Springer, 2014), pp. 119-131.
28. E. E. Wrenbeck et al., An Automated Data-Driven Pipeline for Improving Heterologous Enzyme Expression. *Acs Synthetic Biology* 8, 474-481 (2019).
29. L. Benatuil, J. M. Perez, J. Belk, C.-M. Hsieh, An improved yeast transformation method for the generation of very large human antibody libraries. *Protein Engineering, Design and Selection* 23, 155-159 (2010).
30. T. A. Whitehead et al., Optimization of affinity, specificity and function of designed influenza inhibitors using deep sequencing. *Nature Biotechnology* 30, 543-+ (2012).
31. A. V. Medina-Cucurella, T. A. Whitehead, in *Protein Complex Assembly*. (Springer, 2018), pp. 101-121.
32. C. A. Kowalsky et al., High-Resolution Sequence-Function Mapping of Full-Length Proteins. *Plos One* 10, (2015).
33. M. P. Fay, M. A. Proschan, E. Brittain, Combining one-sample confidence procedures for inference in the two-sample case. *Biometrics* 71, 146-156 (2015).
34. A. V. Medina-Cucurella, Y. Q. Zhu, S. J. Bowen, L. M. Bergeron, T. A. Whitehead, Pro region engineering of nerve growth factor by deep mutational scanning enables a yeast platform for conformational epitope mapping of anti-NGF monoclonal antibodies. *Biotechnology and Bioengineering* 115, 1925-1937 (2018).
35. C. A. Kowalsky, T. A. Whitehead, Determination of binding affinity upon mutation for type I dockerin-cohesin complexes from *Clostridium thermocellum* and *Clostridium cellulolyticum* using deep sequencing. *Proteins* 84, 1914-1928 (2016).

What is claimed is:

1. An isolated spike protein, or a fragment thereof, from a SARS-CoV-2 coronavirus having one or more stabilizing mutations selected from: K41N, K41P, K41S, R44K, K113F, T114D, Q115I, or Q115H, wherein the position of the one or more mutations corresponds to the spike protein encoded by the amino acid sequence according to SEQ ID NO. 2.

2. The spike protein of claim 1, further comprising a mutation selected from:
a substitution mutation from a wild-type amino acid to a proline at residue 987 (987P);
a substitution mutation from a wild-type amino acid to a proline at residue 988 (988P);
a substitution mutation inserting an amino acid sequence according to SEQ ID NO. 55 at residues 682-685; and
wherein the position of the mutation corresponds to the spike protein encoded by the amino acid sequence according to SEQ ID NO. 2.

3. The spike protein of claim 1, further comprising a mutation selected from: L118F, N122Y, V126F, Q134K, N165D, C166A, T167S, T167F, F168Q, E169G, T302N, Q314Y, N360H, Y369R, N370S, N370Y, N370W, A372N, S375H, V382A, V407M, V407R, Q409N, Q409C, I410G, A411I, A411F, A411L, K417V, D428Y, F429D, N487T, N487E, L518S, L518E, H519L, A520G, A520R, A520M, A522T, G526I, P527F, K528F, K528W, K528I, K528L, K529Y, S530I, S530W, T531I, N542C, F543H, F543M, N544I, N544L, N544D, N544F, G545C, G545P, L546F, L546G, L546N, L546M, P561N, P561F, P561Y, P561M, P561V, F562R, F562E, F562D, F562C, Q563M, Q563A, Q563S, Q563L, Q563V, Q564H, F565A, F565D, F565N, T573I, P579T, P579Y, P579D, P579K, Q580F, Q580K, Q580V, Q580I, Q580E, Q580G, Q580K, T581K, T581C, T581Q, L582H, I973N, I973L, I980T, S982M, S982I, R983A, R983V, L984R, L984F, D985S, D985V, E988M, and wherein the position of the mutation corresponds to the spike protein encoded by the amino acid sequence according to SEQ ID NO. 2.

4. The spike protein of claim 1, wherein the spike protein is expressed in a recombinant cell.

5. The spike protein of claim 4, wherein the recombinant cell is a yeast cell.

6. The spike protein of claim 5, wherein the spike protein is displayed on the surface of the yeast cell.

7. A pharmaceutical compositions comprising the spike protein of claim 1, and a pharmaceutically acceptable carrier and optionally at least one adjuvant.

8. A spike protein, or a fragment thereof, from a SARS-CoV-2 coronavirus having one or more mutations selected from:
a substitution mutation from a wild-type amino acid to a proline at residue 988 (988P); and
wherein the position of the mutation corresponds to the spike protein encoded by the amino acid sequence according to SEQ ID NO. 2.

9. The spike protein of claim 8, further comprising a mutation selected from: K41N, K41P, K41S, R44K, K113F, T114D, Q115I, Q115H, L118F, N122Y, V126F, Q134K, N165D, C166A, T167S, T167F, F168Q, E169G, T302N, Q314Y, N360H, Y369R, N370S, N370Y, N370W, A372N, S375H, V382A, V407M, V407R, Q409N, Q409C, I410G, A411I, A411F, A411L, K417V, D428Y, F429D, N487T, N487E, L518S, L518E, H519L, A520G, A520R, A520M, A522T, G526I, P527F, K528F, K528W, K528I, K528L, K529Y, S530I, S530W, T531I, N542C, F543H, F543M, N544I, N544L, N544D, N544F, G545C, G545P, L546F, L546G, L546N, L546M, P561N, P561F, P561Y, P561M, P561V, F562R, F562E, F562D, F562C, Q563M, Q563A, Q563S, Q563L, Q563V, Q564H, F565A, F565D, F565N, T573I, P579T, P579Y, P579D, P579K, Q580F, Q580K, Q580V, Q580I, Q580E, Q580G, Q580K, T581K, T581C, T581Q, L582H, I973N, I973L, I980T, S982M, S982I, R983A, R983V, L984R, L984F, D985S, D985V, E988M, and wherein the position of the mutation corresponds to the spike protein encoded by the amino acid sequence according to SEQ ID NO. 2.

10. The spike protein of claim 8, wherein the spike protein is expressed in a recombinant cell.

11. The spike protein of claim 10, wherein the recombinant cell is a yeast cell.

12. The spike protein of claim 11, wherein the spike protein is displayed on the surface of the yeast cell.

13. A pharmaceutical compositions comprising the spike protein of claim 8, and a pharmaceutically acceptable carrier and optionally at least one adjuvant.

* * * * *